(12) United States Patent
Yung-Yu Hung et al.

(10) Patent No.: US 6,593,365 B1
(45) Date of Patent: Jul. 15, 2003

(54) DIFLUNISAL ESTERS AND RELATED COMPOUNDS

(75) Inventors: Daniel Yung-Yu Hung, Wakerley (AU); Michael Stephen Roberts, Westlake (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 09/402,794

(22) PCT Filed: Apr. 14, 1998

(86) PCT No.: PCT/AU98/00260
§ 371 (c)(1),
(2), (4) Date: Oct. 12, 1999

(87) PCT Pub. No.: WO98/46234
PCT Pub. Date: Oct. 22, 1998

(30) Foreign Application Priority Data

Apr. 11, 1997 (AU) .............................. PO 6123

(51) Int. Cl.$^7$ ................................................ A01N 37/10
(52) U.S. Cl. ........................ 514/533; 514/532; 514/543
(58) Field of Search ................................. 514/532, 533, 514/543

(56) References Cited

U.S. PATENT DOCUMENTS

| 3,681,445 A | * | 8/1972 | Ruyle et al. |
| 3,692,821 A | * | 9/1972 | Sarett et al. |
| 3,714,226 A | * | 1/1973 | Ruyle et al. |

* cited by examiner

Primary Examiner—Paul J. Killos
(74) Attorney, Agent, or Firm—Foley & Lardner

(57) ABSTRACT

O-medium alkyl esters of diflunisal and related compounds are disclosed having anti-platelet activity, hydroxy radical scavenging properties, enhanced hepatic clearance and low ulcerogenic potential. These compounds have general formula (I) wherein n equals 3–13.

4 Claims, 25 Drawing Sheets

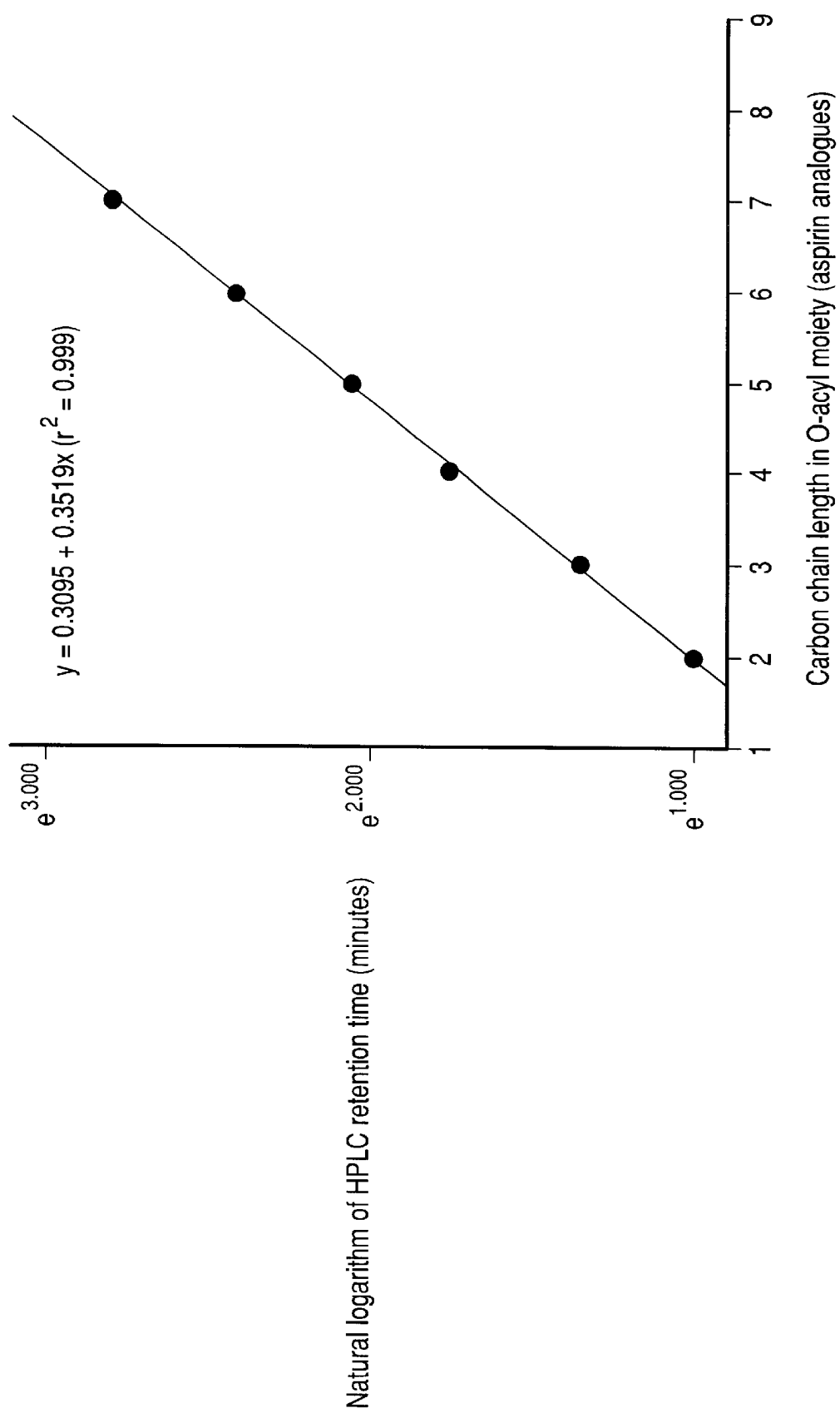

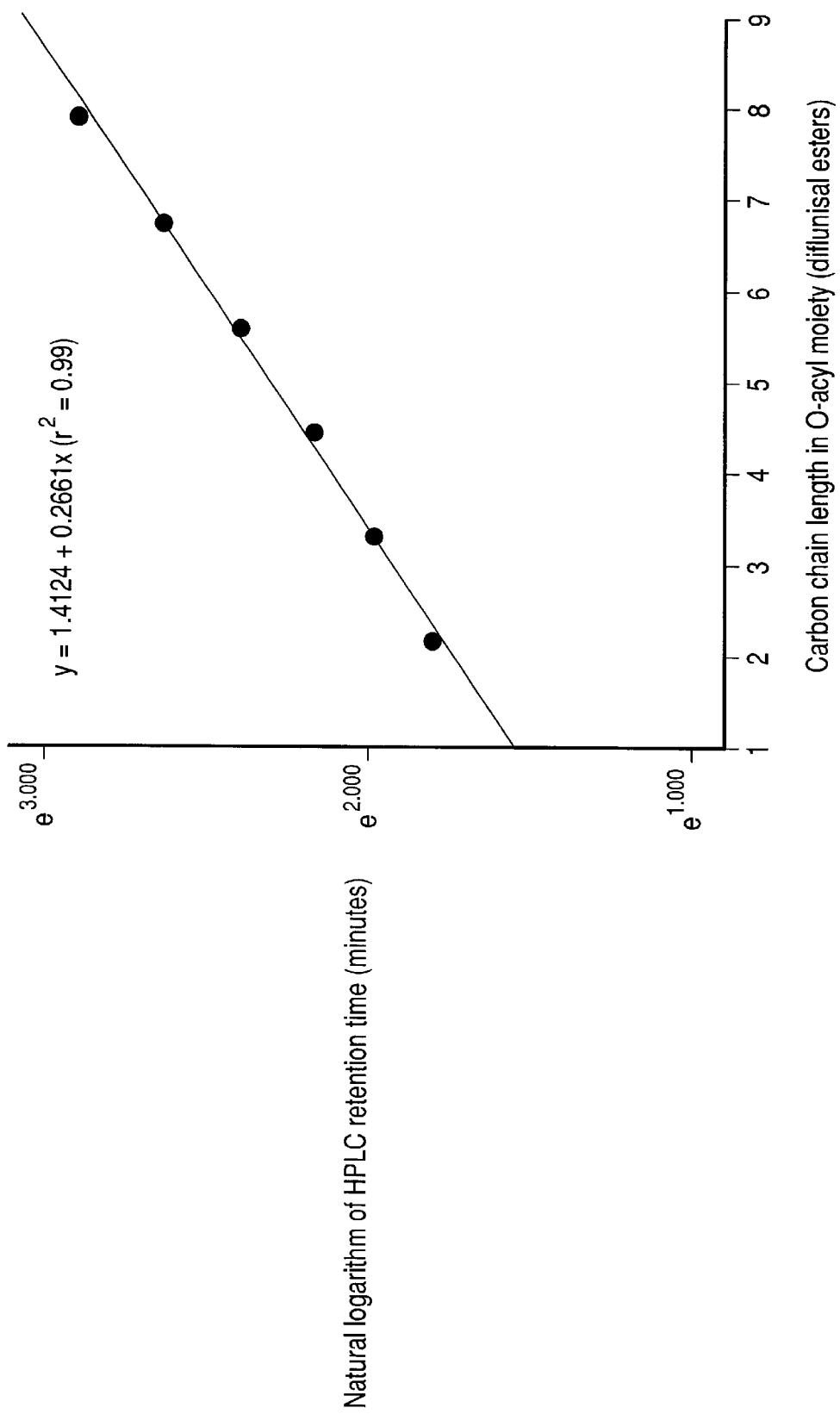

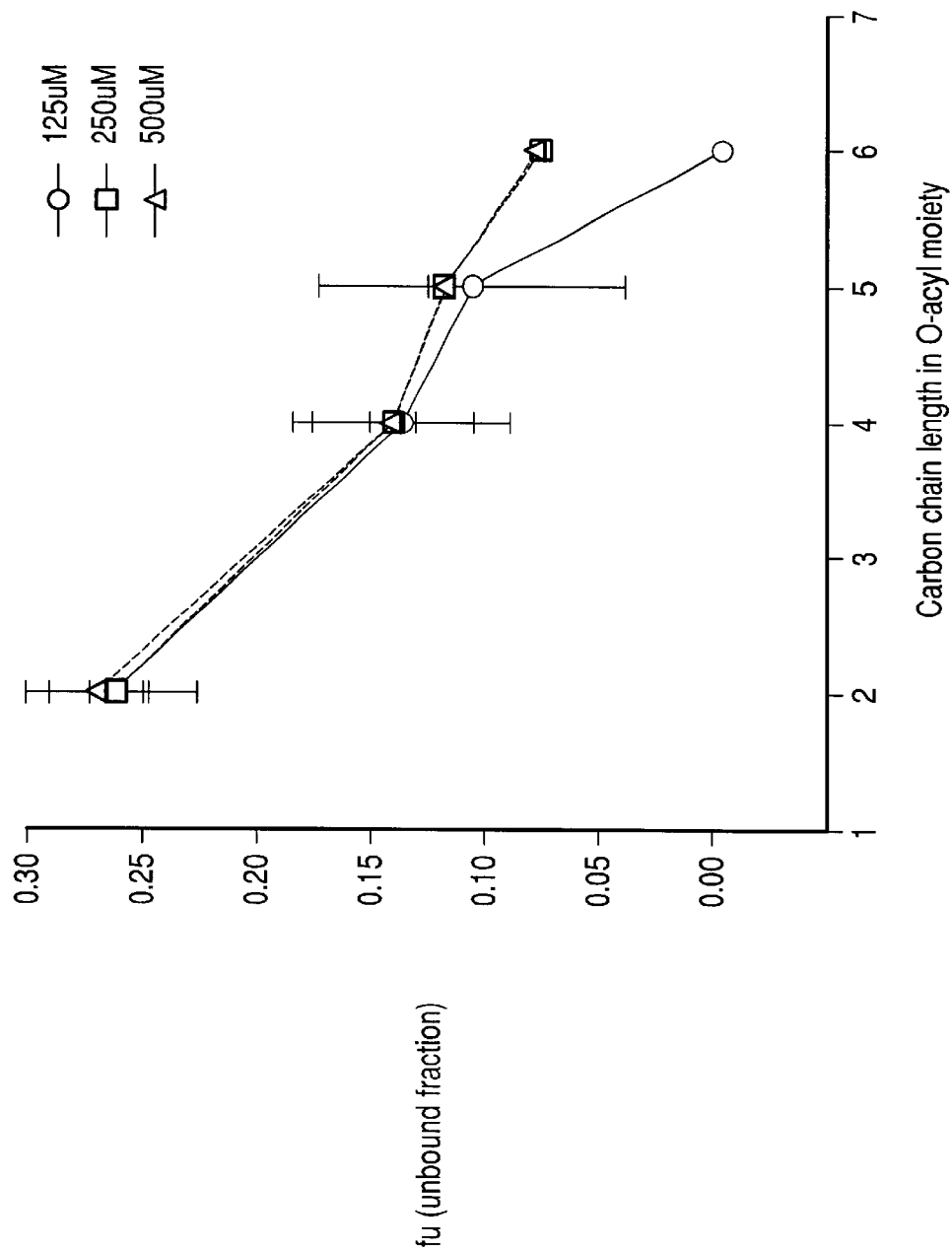

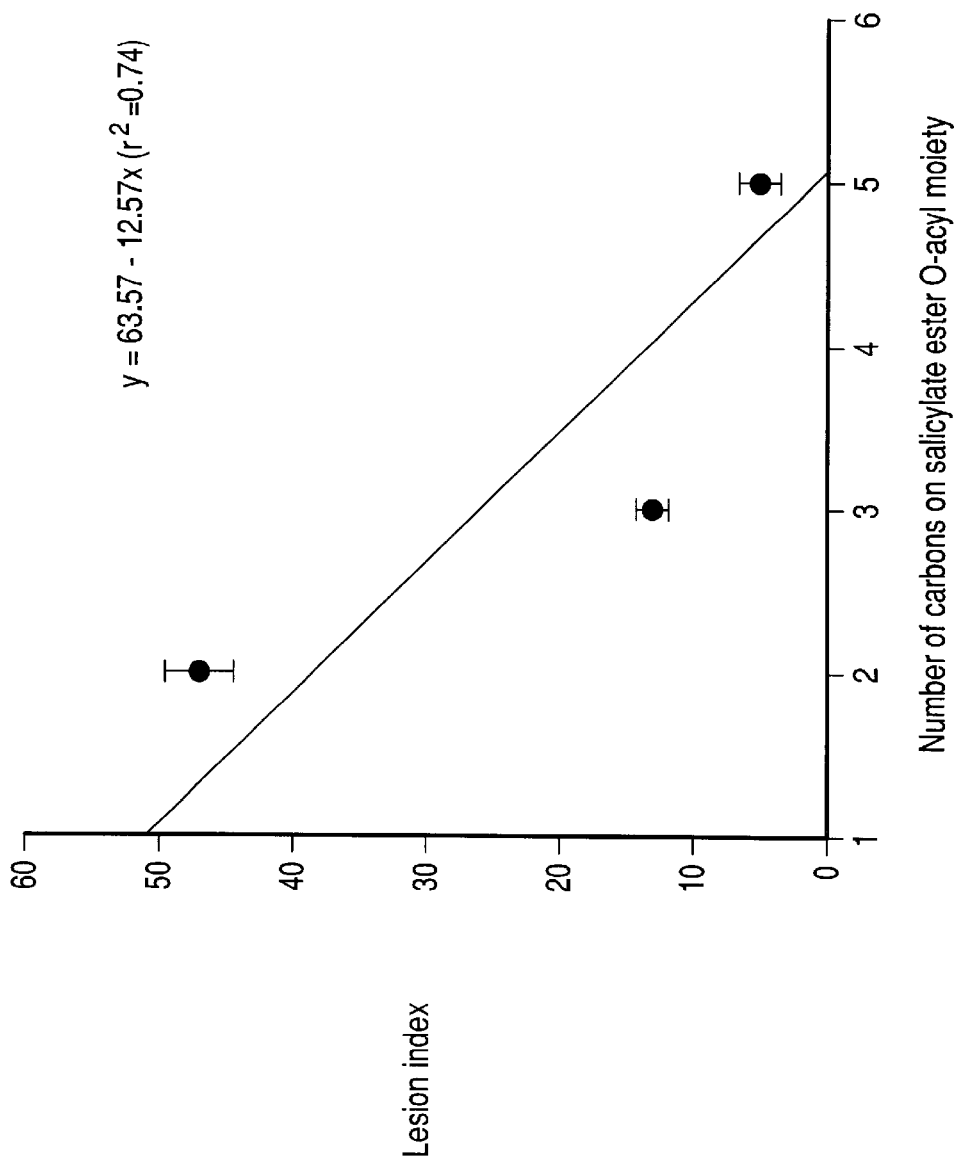

DIFLUNISAL ESTERS AND RELATED COMPOUNDS

FIELD OF THE INVENTION

THIS INVENTION relates to anti-platelet drugs. In particular, this invention relates to novel diflunisal esters and related compounds having anti-platelet activity, hydroxyl radical scavenging properties, enhanced hepatic clearance and low ulcerogenic potential.

BACKGROUND OF THE INVENTION

Aspirin (O-acetylsalicylic acid) is well known for treatment of inflammation, fever and pain and is also well established for secondary stroke prevention (The SALT Collaborative Group, 1991, Lancet 338 1345–1349). In regard to the latter, aspirin is known to inhibit the synthesis of thromboxane $A_2$ in platelets by irreversible acetylation of a serine residue close to the active site of cyclooxygenase, an enzyme which catalyses the formation of an unstable endoperoxide intermediate, $PGH_2$, from arachidonic acid (Lecomte et al, 1994, J. Biochem. 269 13207–13215). Thromboxane $A_2$ is a vasoconstrictor and platelet-aggregating agent and is thus potentially thrombotic.

Whilst such an anti-thromboxane $A_2$ effect may be desirable, aspirin also has a destructive effect on the vascular endothelium since it can inhibit synthesis of prostacyclin by a similar mechanism. Prostacyclin, in this regard, is a vasodilator that inhibits platelet aggregation and is thus potentially anti-thrombotic. In the stomach, prostacyclin is one of the important endogenous prostaglandins that provide local cytoprotection, induce gastric mucosal vasodilation, inhibit acid secretion and conserve gastric mucosal integrity (Gaskill et al, 1982, Surgery 92 220–225; Ligumsky et al, 1982, Am. J. Physiol. 242 G337–341; Walus et al, 1980, Proc. Soc. Exp. Biol. Med. 163 228–232). Aspirin therefore has paradoxical effects, being both a beneficial antiplatelet drug and a significant ulcerogen.

It has been proposed that an optimal antithrombotic effect can be achieved by restricting aspirin to the portal circulation where selective inhibition of platelet cyclooxygenase can occur as distinct from the inhibition of vessel wall cyclooxygenase. In other words, this may have the effect of reducing thromboxane $A_2$ production whilst preventing aspirin reaching the post-hepatic systemic circulation where it might also inhibit prostacyclin synthesis and concomitant promotion of thrombotic and/or ulcerogenic injury (Ali et al, 1980, Stroke 11 9–13; Siebert et al, 1983, Clin. Pharmacol. Ther. 33 367–374; Pedersen et al, 1984, N. Engl. J. Med. 311 1206–1211; Roberts et al,. 1986, Lancet 1 1153–1154; McLeod et al, 1988, Austr. NZ. J. Med. 148 207).

Confining the inhibition of cyclooxygenase activity to the portal circulation depends on extensive first pass hepatic de-acetylation of the aspirin, forming platelet-inactive salicylate. Previous studies, however, have demonstrated that the extraction of aspirin by the liver is incomplete: hepatic availabilities being reported to be between 0.6 and 0.8 for man (Harris et al, 1969, J. Pharm. Sci. 58 71–75), sheep (Cossum et al, 1986, J. Pharm. Sci. 75 731–737) and rat (Iwamoto et al, 1982, J. Pharm. Pharmacol. 34 176–180; Wientjes et al, 1988, J. Pharmacol. Exp. Ther. 245 809–815). Thus, substantial quantities of aspirin bypass the liver through an inefficient hepatic extraction and aspirin is not restricted to the portal circulation.

Various aspirin analogues/derivatives have been described in the prior art with improved efficacy in relation to treatment of pain and inflammation. In U.S. Pat. No 5,599,959 (Hosmane et al), there is disclosed analogues of aspirin having the structure:

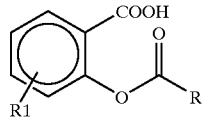

wherein R is defined as being selected from the group consisting of hydrogen, methyl, ethyl, n-propyl, l-propyl, n-butyl, l-butyl, pentyl, hexyl, heptyl, octyl, nonyl, decyl, undecyl, phenyl, naphthyl and cyclohexyl. R1 is defined as being selected from the group consisting of hydrogen, a C1—C12 alkyl group, F, Cl, Br, I, $CO_2H$, CONHR, $CONR_2$, CO2R, CHO, COR, $SO_3R$, $SO_2NHR$, $SC_2NR_2$, OH, OR, OCOR, SH, SR, OCONHR, $OCONR_2$, SCOR, SCONHR, $SCONR_2$ and $NH_2$, NHR, NHCOR and $NR_2$. The foregoing aspirin analogues were shown by Hosmane et al to adsorb into membranes of red blood cell and to decrease membrane viscoelasticity of such cells. According to Hosmane et al, a decrease in membrane stiffness would lead to a decrease in flow resistance experienced by red cells, and hence, a decrease in their mean capillary transit times (mean cell transit time). A positive correlation was also shown to exist between the amount of membrane adsorption and the lipophilicity of the aspirin analogue. Accordingly, Hosmane et al teach that such aspirin analogues may be advantageously used to treat diseases which have origin in poor blood supply or circulation such as heart disease, stroke, painful leg, and calf muscles, chest pain, atherosclerosis and dry gangrene. Hosmane et al, however, neither teach nor suggest compounds having anti-platelet activity with enhanced hepatic clearance and low ulcerogenic, potential.

Diflunisal (2',4'-difluoro-4-hydroxy-3-biphenylcarboxylic acid) is a salicylic acid derivative and is known to be analogous to aspirin insofar as treatment of inflammation, fever and pain and propensity for gastrointestinal injury. Various diflunisal derivatives have been described in the prior art having enhanced analgesic potency and anti-pyretic activity compared to the parent drug. Related diflunisal compounds are disclosed in U.S. Pat. No 4,044,049 (Ruyle et al). This patent is directed broadly to substituted 5-(phenyl) benzoic acid esters having the general formula:

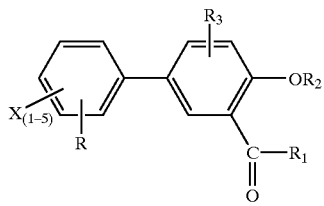

wherein $X_{(1-5)}$, R, $R_1$ and $R_3$ are as defined hereinafter. The term $R_2$ is defined in this specification as being selected from the group consisting of hydrogen, lower alkyl (such as methyl, ethyl, butyl pentyl, and the like), lower alkanoyl (where "lower" is referring to acetyl, propionyl, butyryl and the like having an upper limit of 4 carbon atoms), and lower alkenyl (such as allyl, butenyl, and the like). In this regard, it should be noted that the only lower alkanoyl ester of 5-(phenyl) benzoic acid exemplified in the specification is 2-acetoxy-5-(4'fluoropheny)-benzoic acid and no other. In particular, this patent is concerned with anti-inflammatory properties of these compounds. However, there is no explicit disclosure in Ruyle et al of O-medium and longer alkyl esters of diflunisal which are the subject of this application nor are there methods disclosed which can result in the production of such esters.

In light of the above, the prior art is deficient in the lack of effective compounds having anti-platelet activity, enhanced hepatic clearance and low ulcerogenic potential.

The current invention arises from the unexpected discovery that by increasing the carbon number in the ester O-acyl moiety of diflunisal and related compounds, a marked enhancement in hepatic extraction results with a simultaneous reduction in ulcerogenicity. This greater rate of hepatic elimination is considered to minimise exposure of these esters to the systemic circulation thereby minimising prostacyclin inhibition within the vessel endothelium. Surprisingly, it has also been found that these and other diflunisal esters have anti-platelet activity as well as hydroxyl radical scavenging properties which make them suitable for use as active agents for treatment and/or control of thrombosis and ischaemic/reperfusion injury of tissues such as liver.

OBJECT OF THE INVENTION

It is therefore an object of the present invention to provide novel diflunisal esters and related compounds having anti-platelet properties and reduced ulcerogenic potential compared to diflunisal and aspirin.

It is another object of the invention to provide pharmaceutical compositions comprising these diflunisal esters as well as methods of treating mammals therewith.

Other objects of the invention will become apparent from the following disclosure.

SUMMARY OF THE INVENTION

According to one aspect of the invention, there is provided O-medium alkyl esters of diflunisal and related compounds having the general formula:

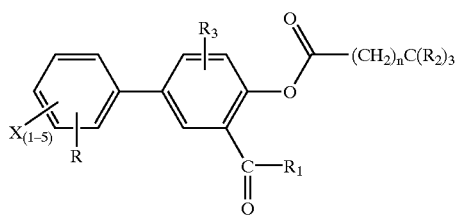

(I)

wherein:
n equals 3–13
X is a halogen (chloro, bromo, fluoro and iodo, especially chloro or fluoro), X being on one or more of the phenyl carbon atoms; R is selected from the group consisting of hydrogen, halogen (chloro, bromo, and fluoro), lower alkyl (such as methyl, ethyl, butyl, pentyl and the like), and lower alkoxy (such as methoxy, ethoxy, butoxy, and the like); $R_1$ is selected from the group consisting of hydroxy, amino, loweralkoxy (such as methoxy, ethoxy, butoxy, pentoxy, and the like), lower alkylamino (methylamino, propylamino, pentylamino, and the like), di(lower alkyl)amino (dimethylamino, dibutylamino, propylpentylamino, and the like), diloweralkylaminoloweralkylamino, diloweralkylaminoloweralkoxy, hydroxyloweralkoxy, (3-hydroxypropoxy, 2-hydroxypropoxy, 4-hydroxybutoxy and the like), polyhydroxyloweralkoxy (2,3-dihydroxypropoxy, 2,3,4,5,6-pentahydroxyhexyloxy and the like), loweralkoxyloweralkoxy (ethoxyethoxy), phenyl-loweralkoxy (benzyloxy, phenethoxy and the like), phenoxy, substituted phenoxy (such as loweralkanoylamino, benzyloxy-2-carboxy4-(4'-fluorophenyl), carboxy and carbloweralkoxy, loweralkanoylamino-loweralkoxy, hydrazino, (hydroxylamino), N-morpholino, N-(4-loweralkyl-piperidino) N-[4-(hydroxyloweralkyl)-piperidino], (hydroxyloweralkyl) amino and a naturally occurring amino acid radical with attachment at the N, such as glycine, phenylalanine, proline, methionine - and taurine;
$R_2$ is hydrogen or a halogen or combination thereof; and
$R_3$ is selected from the group consisting of hydrogen, 3-lower alkenyl, 3- and 4-lower alkyl, lower alkoxy, benzyl and halo;
or a pharmaceutically acceptable salt thereof.

Preferably, n=3–5.

Suitably, X is fluoro. In such a case, the fluoro group is preferably on two of said phenyl carbon atoms, more preferably, on the 2' and 4' phenyl carbon atoms.

R is preferably hydrogen, halo or lower alkyl.

Suitably, $R_1$ is hydroxy or amino but preferably is hydroxy.

Preferably, $R_2$ is hydrogen.

Preferred representative compounds of the invention include medium and long alkanoyl derivatives of diflunisal and more preferably pentanyl, hexanyl and heptanyl derivatives of diflunisal as well as pharmaceutically acceptable salts thereof.

The term "pharmaceutically acceptable salts" as used herein refers to salts which are toxicologically safe for systemic administration. The pharmaceutically acceptable salts of said benzoic acid may be selected from the group including the alkali (Na, K, Li) and alkali earth (Mg, Ca, Ba), ammonium, aluminium, iron, amine, glucosamine, choline, sulphate, bisulphate, nitrate, citrate, tartrate, bitartrate, phosphate, carbonate, bicarbonate, malate, maleate, napsylate, fumarate, succinate, acetate, terephthalate, pamoate, pectinate and S-methyl methionine salts, piperazine, and the like.

In another aspect, the invention resides in a pharmaceutical composition for treating and/or controlling in a mammal thrombosis, hydroxyl radical-related diseases, inflammation, fever or pain comprising an effective dosage of a compound of Formula I.

Dosage forms of the pharmaceutical composition include tablets, dispersions, suspensions, injections, solutions, syrups, troches, capsules, suppositories, aerosols and the like. These dosage forms may also include injecting or implanting slow releasing devices designed specifically for this purpose or other forms of implants modified to act additionally in this fashion. Slow or controlled release of a compound according to Formula I may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutically-acceptable carriers for systemic administration may also be incorporated into the compositions of this invention.

By "pharmaceutically-acceptable carrier" is meant a solid or liquid filler, diluent or encapsulating substance which may be safely used in systemic administration. Depending upon the particular route of administration, a variety of pharmaceutically-acceptable carriers, well known in the art may be used. These carriers may be selected from a group including sugars, starches, cellulose and its derivatives, malt, gelatine, talc, sterotix, pectin, cab-o-sil, acacia, calcium sulfate, stearic acid, magnesium stearate, terra alba, agar, vegetable oils, synthetic oils, polyols, alginic acid, phosphate buffered solutions, emulsifiers, isotonic saline, and pyrogen-free water.

Pharmaceutical compositions of the present invention suitable for oral or parenteral administration may be presented as discrete units such as capsules, sachets or tablets each containing a pre-determined amount of the compound according to Formula I, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the effective dosage of the compound of Formula I with the carrier which constitutes one or more necessary ingredients. In general, the compositions are prepared by uniformly and intimately admixing the compound of Formula I with liquid carriers or finely divided solid carriers or both, and then, if necessary, shaping the product into the desired presentation.

The pharmaceutical composition may be in the form of a sterile injectable preparation, for example as a sterile injectable aqueous or oleaginous suspension. This suspension may be formulated using suitable dispersing or wetting agents and suspending agents which are well known to those of skill in the art.

The active compounds of Formula I and of the compositions of this invention are present in an amount sufficient to treat and/or control thrombosis, hydroxyl radical related diseases such as ischaemic/reperfusion injury of tissue, inflammation, fever or pain. Suitable dosages of the compounds of Formula I and of the pharmaceutical compositions containing such compounds may be readily determined by those of skill in the art. In this regard, the amount of active compounds of Formula I that may be present in the dosage of a pharmaceutical composition according to the invention will vary depending on the host treated, the condition to be treated and/or controlled and the particular mode of administration hereinafter described. For example, a formulation intended for oral administration of humans in need of treatment and/or control of thrombosis may contain the active ingredient, namely, the compounds of Formula I in an amount from 0.2 mg to 5 mg per kg body weight per day (10 mg to 250 mg per patient per day (preferably from about 2 mg to 3 mg per kg body weight per day (100 mg to 150 mg per patient per day). In the case of treatment of inflammation, suitable formulations intended for oral administration of humans may contain the compounds of Formula I in an amount from 0.2 mg to 140 mg per kg body weight per day (10 mg to 7 g per patient per day (preferably from about 0.5 mg to 50 mg per kg body weight per day (25 mg to 3.5 g per patient per day).

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease or condition undergoing therapy.

According to another aspect of the invention there is provided a method for treating and/or controlling thrombosis, hydroxyl radical related diseases, inflammation, pain and fever comprising administering to a mammal in need of such treatment a composition comprising an effective dosage of a compound of Formula I.

Any suitable route of administration may be employed for providing a mammal the composition of the invention. For example, oral, rectal, parenteral, ocular, sublingual, inhalational, buccal, intrathecal, epidural, intravenous, intra-articular, intramuscular, intraperitoneal, sub-cutaneous, transdermal, intravenous, or intracerebroventricular and the like may be employed. It will be appreciated that the particular route of administration will vary, for example, upon the particular disease or condition under therapy.

In yet another aspect of the invention, there is provided a method of treating and/or controlling thrombosis comprising administering to a mammal in need of such treatment a composition comprising an effective dosage of a compound having the general formula:

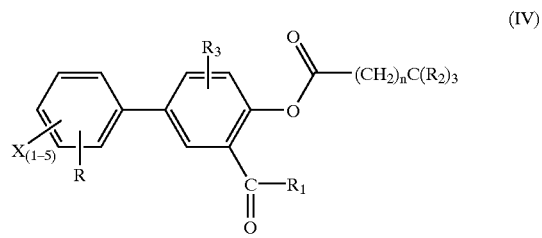

(IV)

wherein:
n equals 0–13
X is a halogen (chloro, bromo, fluoro and iodo, especially chloro or fluoro), X being on one or more of the phenyl carbon atoms;
R is selected from the group consisting of hydrogen, halogen (chloro, bromo, and fluoro), lower alkyl (such as methyl, ethyl, butyl, pentyl and the like), and lower alkoxy (such as methoxy, ethoxy, butoxy, and the like);
$R_1$ is selected from the group consisting of hydroxy, amino, loweralkoxy (such as methoxy, ethoxy, butoxy, pentoxy, and the like), lower alkylamino (methylamino, propylamino, pentylamino, and the like), di(lower alkyl) amino (dimethylamino, dibutylamino, propylpentylamino, and the like), diloweralkylaminoloweralkylamino, diloweralkylaminoloweralkoxy, hydroxyloweralkoxy, (3-hydroxypropoxy, 2-hydroxypropoxy, 4-hydroxybutoxy and the like), polyhydroxyloweralkoxy (2,3-dihydroxypropoxy, 2,3,4,5,6-pentahydroxyhexyloxy and the like), loweralkoxyloweralkoxy (ethoxyethoxy), phenyl-loweralkoxy (benzyloxy, phenethoxy and the like), phenoxy, substituted phenoxy (such as loweralkanoylamino, benzyloxy-2-carboxy-4-(4'-fluorophenyl), carboxy and carbloweralkoxy, loweralkanoylamino-loweralkoxy, hydrazino, (hydroxylamino), N-morpholino, N-(4-loweralkyl-piperidino) N-[4-(hydroxyloweralkyl)-piperidino], (hydroxyloweralkyl) amino and a naturally occurring amino acid radical with attachment at the N, such as glycine, phenylalanine, proline, methionine and taurine;
$R_2$ is hydrogen or a halogen or combination thereof; and
$R_3$ is selected from the group consisting of hydrogen, 3-lower alkenyl, 3- and 4-lower alkyl, lower alkoxy, benzyl and halo;
or a pharmaceutically acceptable salt thereof.
In such a case, n preferably equals 0–6.
Preferred representative compounds which can be used in accordance with the above method include alkanoyl derivatives of diflunisal, more preferably medium and long alkanoyl derivatives inclusive of acetyl, propionyl, butyryl, pentanoyl, hexanoyl and heptanoyl derivatives and pharmaceutically acceptable salts thereof.

In still yet another aspect of the invention, there is provided a method of treating and/or controlling a hydroxyl radical-related disease comprising administering to a mammal in need of such treatment a composition comprising an effective dosage of a compound according to Formula IV.

In such a case, n preferably equals 0–6.

Suitable compounds which can be utilised in the above method include diflunisal as well as alkanoyl derivatives of diflunisal, more preferably medium and, long alkanoyl derivatives inclusive of acetyl, propionyl, butyryl, pentanoyl, hexanoyl and heptanoyl derivatives and pharmaceutically acceptable salts thereof.

In another aspect, the invention resides in a process of preparation of compounds according to Formula I including the step of acylating a compound of general formula:

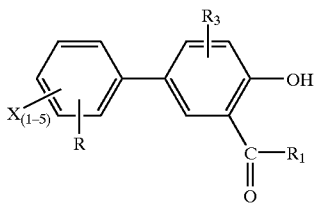

(II)

with an appropriate acylating agent.

An appropriate acylating agent according to the invention may include a medium alkanoic acid anhydride, particularly a C3—C13 anhydride such as propionic anhydride, butyric anhydride and the like.

According to a further aspect of the invention, there is provided a method of treating and/or controlling thrombosis comprising administering to a mammal in need of such treatment a composition comprising an effective dosage of a compound having the general formula:

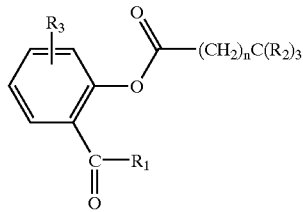

(III)

wherein:
n equals 1–13;
$R_1$ is selected from the group consisting of hydroxy, amino, loweralkoxy (such as methoxy, ethoxy, butoxy, pentoxy, and the like), lower alkylamino (methylamino, propylamino, pentylamino, and the like), di(lower alkyl) amino (dimethylamino, dibutylamino, propylpentylamino, and the like), diloweralkylaminoloweralkylamino, diloweralkylaminoloweralkoxy, hydroxyloweralkoxy, (3-hydroxypropoxy, 2-hydroxypropoxy, 4-hydroxybutoxy and the like), polyhydroxyloweralkoxy (2,3-dihydroxypropoxy, 2,3,4,5,6-pentahydroxyhexyloxy and the like), loweralkoxyloweralkoxy (ethoxyethoxy), phenyl-loweralkoxy (benzyloxy, phenethoxy and the like), phenoxy, substituted phenoxy (such as loweralkanoylamino, benzyloxy-2-carboxy4-(4'-fluorophenyl), carboxy and carbloweralkoxy, loweralkanoylamino-loweralkoxy, hydrazino, (hydroxylamino), N-morpholino, N-(4-loweralkyl-piperidino) N-[4-(hydroxyloweralkyl)-piperidino], (hydroxyloweralkyl) amino and a naturally occurring (amino acid radical with attachment at the N, such as glycine, phenylalanine, proline, methionine and taurine;
$R_2$ is hydrogen or a halogen or combination thereof; and $R_3$ is selected from the group consisting of hydrogen, 3-lower alkenyl, 3- and 4-lower alkyl, lower alkoxy, benzyl and halo;
or a pharmaceutically acceptable salt thereof.
Preferably, n=1–6
Suitably, $R_1$ is hydroxy or amino but preferably is hydroxy.
Preferably, $R_2$ is hydrogen.

Preferred representative compounds according to Formula III which may be employed advantageously in the above method include alkanoyl salicylic acids inclusive of propionyl, butyryl, pentanoyl, hexanoyl and heptanoyl derivatives as well as pharmaceutically acceptable salts thereof.

In a still further aspect, the invention resides in a method of treating and/or controlling a hydroxyl radical-related disease comprising administering to a mammal in need of such treatment a composition comprising an effective dosage of a compound having a general formula:

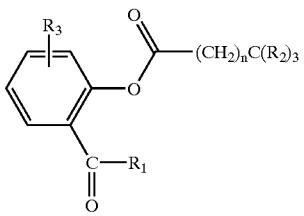

(V)

wherein:
n equals 0–13;
$R_1$ is selected from the group consisting of hydroxy, amino, loweralkoxy (such as methoxy, ethoxy, butoxy, pentoxy, and the like), lower alkylamino (methylamino, propylamino, pentylamino, and the like), di(lower alkyl) amino (dimethylamino, dibutylamino, propylpentylamino, and the like), diloweralkylaminoloweralkylamino , diloweralkylaminoloweralkoxy, hydroxyloweralkoxy, (3-hydroxypropoxy, 2-hydroxypropoxy, 4-hydroxybutoxy and the like), polyhydroxyloweralkoxy (2,3- dihydroxy propoxy, 2,3,4,5,6-pentahydroxyhexyloxy and the like), loweralkoxyloweralkoxy (ethoxyethoxy), phenyl-loweralkoxy (benzyloxy, phenethoxy and the like), phenoxy, substituted phenoxy (such as loweralkanoylamino, benzyloxy-2-carboxy-4-(4'-fluorophenyl), carboxy and carbloweralkoxy, loweralkanoylamino-loweralkoxy, hydrazino, (hydroxylamino), N-morpholino, N-(4-loweralkyl-piperidino) N-[4-(hydroxyloweralkyl)-piperidino], (hydroxyloweralkyl) amino and a naturally occurring amino acid radical with attachment at the N, such as glycine, phenylalanine, proline, methionine and taurine;
$R_2$ is hydrogen or a halogen or combination thereof; and
$R_3$ is selected from the group consisting of hydrogen, 3-lower alkenyl, 3- and 4-lower alkyl, lower alkoxy, benzyl and halo;
or a pharmaceutically acceptable salt thereof.
Preferably, n=1–6
Suitable representative compounds in accordance with Formula III which may be utilised in the above method include but are not limited to alkanoyl salicylic acids inclusive of acetyl, propionyl, butyryl, pentanyl, hexanyl and heptanyl derivatives as well as pharmaceutically acceptable salts thereof.

In order that the invention may be readily understood and put into practical effect, particular preferred embodiments will now be described by way of example with reference to the accompanying drawings in which:

FIGS. 1a & 1b shows the relationship between HPLC retention time and carbon chain length of the ester O-acyl moiety for (a) aspirin analogues, and (b) diflunisal esters;

FIGS. 5a & 5b shows the relationship between unbound fraction ($f_u$) of the aspirin analogues (a) and diflunisal esters (b) versus carbon chain length at various concentrations;

FIGS. 6a & 6b shows the relationship between lesion index and carbon chain length in the ester O-acyl moiety; (a): salicylic acid derivatives, (b): diflunisal esters;

EXAMPLE 1

Figure 2:
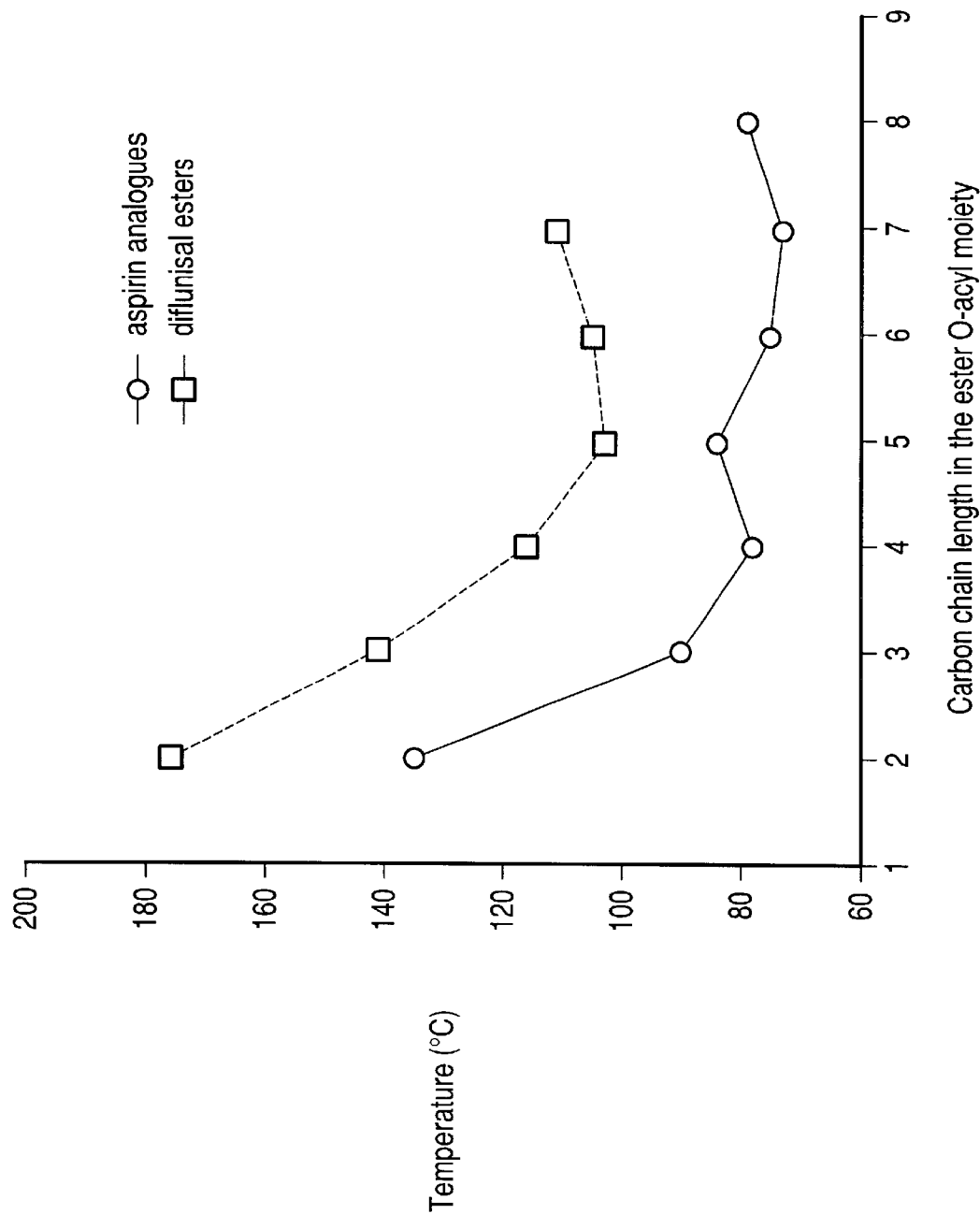
FIG. 2 shows the relationship between melting point and the carbon chain length of the ester O-acyl moiety.

Synthesis, Identification, Characterization Stability, Solubility and Protein Binding of Ester Derivatives of Salicylic Acid and Diflunisal Materials and Methods Apparatus Infrared (IR) spectra were recorded for solids in potassium bromide (Kbr) discs on a Perkin-Elmer 599 grating spectrophotometer. $^1$H-NMR spectral measurements were run on a Brucker X32 500 MHZ spectrometer, using deuterochloroform ($CDCl_3$) as a solvent and tetramethylsilane (T.M.S.) as the internal standard. Mass spectra were obtained with a Perkin-Elmer API III Biomolecular Mass analyser. Melting point ranges were determined in capillary tubes with an electrothermal melting point apparatus and are uncorrected. High-performance liquid chromatography (HPLC) was generally carried out using a system consisting of a double piston pump (Waters, Model 510), an autoinjector (Waters, Model 710b) with a variable wavelength UV detector (Waters, Model 480), an interface module (Millipore-Waters), an NEC personal computer and a 5 micron Brownlee $C_{18}$ reversed phase column (250×4.6 mm, Applied Biosystems).

Synthesis

Salicylic acid (2-hydroxybenzoic acid) and diflunisal [5-(2,4-difluorophenyl) salicylic acid] were obtained from Sigma Chemical Company (USA), and used without any further purification. Acetic anhydride, propionic anhydride, butyric anhydride, valeric anhydride (pentanoic anhydride), caproic anhydride (hexanoic anhydride), heptanoyl chloride, and octanoyl chloride were obtained from Aldrich Chemical Co., Ltd. (USA). Two methods were employed for the synthesis of ester derivatives of salicylic acid and diflunisal in this work. The short chain compounds (2 to 6 carbon atoms in the O-acyl moiety) were prepared from acyl anhydrides in the presence of sulfuric acid as a catalyst (Scheme I). The medium chain compounds (7 to 8 carbon atoms in the O-acyl moiety) were prepared from acyl chlorides in the presence of pyridine (Scheme II).

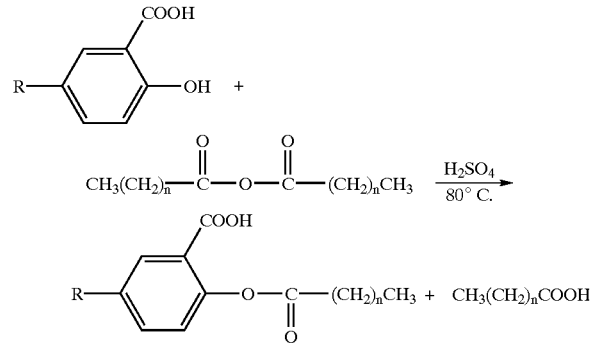

Scheme I (R=H or 2,4-difluorophenyl, n=0–4)

General procedure (Scheme I): Salicylic acid (2 g, 0.014 mole) or diflunisal (1 g, 0.004 mole) was placed in the reaction flask and excess of the appropriate acyl anhydride with 3 drops of sulfuric acid was added quickly. The mixture was heated on a water bath (80° C.) for 2 hours. The mixture was then cooled and diluted with ice water (25 mL) to destroy the excess anhydride. A white to dark brown milky suspension was formed. The suspension was put in a separating funnel and extracted 5 times with chloroform or methylene chloride. Sodium sulfate (anhydrous) was then added to the pooled extracts. The mixture was filtered and the filtrate was concentrated under reduced pressure. A crude compound was obtained as a yellowish-white to dark brown solid.

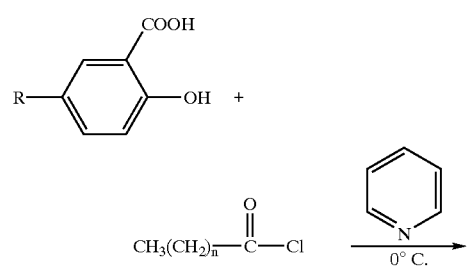

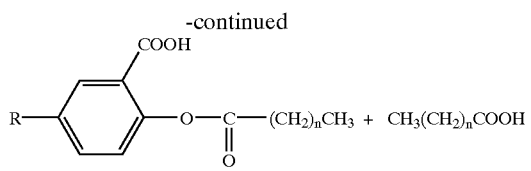

Scheme II (R=H or 2,4-difluorophenyl, n=5–6)

General procedure (Scheme II): Salicylic acid (2 g, 0.014 mole) or diflunisal (1 g, 0.004 mole) was placed in the reaction flask and 15 mL of pyridine was added. The flask was immersed in an ice bath and placed on a magnetic stirrer. An appropriate acyl chloride was added dropwise over 30 minutes from a pressure-equalizing dropping funnel to the well-stirred mixture. The mixture was stirred at 0° C. for another 60 minutes. Cold water (20 mL) was then added to dissolve the pyridinium salt. A greenish to orange milky suspension was formed. This was transferred to a round-bottomed flask by a Pasteur pipette, and then 50 mL of chloroform was added. After thorough mixing, the chloroform was evaporated under reduced pressure. this procedure was repeated several times until the odour of pyridine was removed. The flask was then cooled in ice and swirled continuously until a yellowish-white to light orange solid of crude compound was obtained.

(a) Synthesis of n-propionylsalicylic acid (C3SA).

0.036 mole (4.64 mL) of propionic anhydride was used in the acylation. Crude C3SA was obtained as a yellowish-white solid (2.47 g). It was recrystallised twice from ethanol-water (2:5) and twice from petroleum spirit as white needles (2.13 g, 75.8% overall yield), m.p. 90–92° C. IR $v_{Max}$ 2950 (C–H), 1740 (ester C=O), 1670 (acid C=O) cm$^{-1}$. $^1$H NMR (CDCl$_3$) δ 7.12–7.95 (m, 4H, Ar-$\underline{H}$),

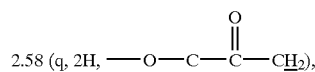

1.18 (t, 3H, C$\underline{H}_3$) ppm. M$^+$ 194; C$_{10}$H$_{10}$O$_4$ requires 194.

(b) Synthesis of n-butanoylsalicylic acid (C4SA).

0.033 mole (5.46 mL) of butyric anhydride was used in the acylation. Crude C4SA was obtained as a yellowish-white solid (1.15 gm). It was recrystallised once from ethanol-water (2:5) and three times from petroleum spirit as white crystals (0.85 gm, 28.2% overall yield), m.p. 78–79° C. IR $v_{Max}$ 2950 (C–H), 1740 (ester C=O), 1670 (acid C=O) cm$^{-1}$. $^1$H NMR (CDCl$_3$) δ 6.89–7.88 (m, 4H, Ar-$\underline{H}$),

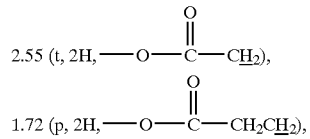

0.99 (t, 3H, C$\underline{H}_3$) ppm. M$^+$208; C$_{11}$H$_{12}$O$_4$ requires 208.

(c) Synthesis of n-pentanoylsalicylic acid (C5SA).

0.036 mole (7.15 mL) of valeric anhydride was used in the acylation. Since valeric acid is slightly soluble in water, it was difficult to separate it from C5SA by the chloroform extraction method (described in Scheme I). A modified procedure was designed to resolve this problem. After a brownish milky suspension was formed, it was transferred to a 25 mL conical flask by a Pasteur pipette and kept in a –20° C. freezer for 24 hours. C5SA was converted into a solid on freezing, but valeric acid remained as a liquid, due to its low melting point (–34.5° C.). Therefore, valeric acid could be removed by a Pasteur pipette. Since a trace of valeric acid was still combined with the solid, a small amount of cold petroleum spirit was added to dissolve it. This petroleum spirit solution was then pipetted out and the procedure was repeated several times to eliminate the valeric acid residue. Finally, crude C5SA was obtained as a pearly white solid (1.58 g). It was recrystallised once from ethanol-water (2:5) and three times from petroleum spirit as pearly white plates (1.03 g, 32% overall yield), m.p. 81–84° C. IR $v_{Max}$ 2950 (C–H), 1740 (ester C=O) 1690 (acid C=O) cm$^{-1}$. $^1$H NMR (CDCl$_3$) δ 7.09–8.09 (m, 4H, Ar-$\underline{H}$),

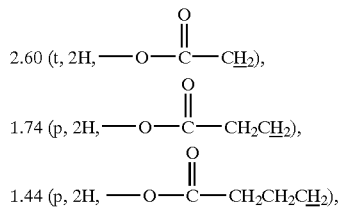

0.93 (t, 3H, C$\underline{H}_3$) ppm. M$^+$222; C$_{12}$H$_{14}$O$_4$ requires 222.

(d) Synthesis of n-hexanoylsalicylic acid (C6SA).

0.036 mole (8.38 mL) of caproic anhydride was used in the acylation. Crude C6SA was obtained as a white solid (2.01 gm). It was recrystallised once from ethanol-water (2:5) and three times from petroleum spirit as white crystals (1.22 gm, 35.7% overall yield), m.p. 73–75° C. IR $v_{Max}$ 2950 (C–H), 1750 (ester C=O), 1670 (acid C=O) cm$^{-1}$. $^1$H NMR (CDCl$_3$) δ 6.92–8.10 (m, 4H, Ar-$\underline{H}$),

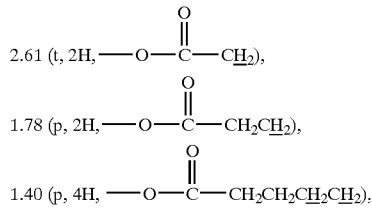

0.93 (t, 3H, C$\underline{H}_3$) ppm. M$^+$236; C$_{13}$H$_{16}$O$_4$ requires 236.

(e) Synthesis of n-heptanoylsalicylic acid (C7SA).

0.018 mole (2.70 mL) of heptanoyl chloride was used in the acylation. Crude C7SA was obtained as a yellowish-white solid (1.30 g). It was recrystallised once from acetone-petroleum spirit (1:4) and three times from petroleum spirit as white crystals (0.46 gm, 12.7% overall yield), m.p. 72–73° C. IR $v_{Max}$ 2940 (C–H), 1745 (ester C=O), 1700 (acid C=O) cm$^{-1}$. M$^+$250; C$_{14}$H$_{18}$O$_4$ requires 250.

(f) Synthesis of n-octanoylsalicylic acid (C8SA).

0.018 mole 5 (2.96 mL) of octanoyl chloride was used in the acylation. Crude C8SA was obtained as a yellowish-white solid (1.46 g). It was recrystallised once from acetone-petroleum spirit (1:4) and three times from petroleum spirit as white crystals (0.78 g, 20.4% overall yield), m.p. 77–79° C. IR $v_{Max}$ 2940 (C–H), 1750 (ester C=O), 1700 (acid C=O) cm$^{-1}$. $^1$H NMR (CDCl$_3$) δ 6.92–8.10 (m, 4H, Ar-$\underline{H}$),

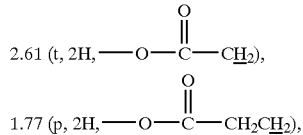

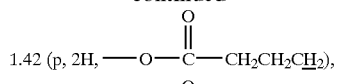1.42 (p, 2H, —O—C(=O)—CH$_2$CH$_2$C$\underline{H}_2$),

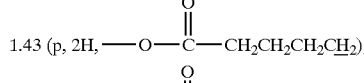1.43 (p, 2H, —O—C(=O)—CH$_2$CH$_2$CH$_2$C$\underline{H}_2$),

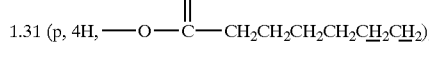1.31 (p, 4H, —O—C(=O)—CH$_2$CH$_2$CH$_2$CH$_2$C$\underline{H}_2$CH$_2$).

0.89 (t, 3H, C$\underline{H}_3$) ppm. M$^+$264; C$_{15}$H$_{20}$O$_4$ requires 264.

(g) Synthesis of acetyldiflunisal (C2D).

0.03 mole (2.85 mL) of acetic anhydride was used in the acylation. Crude C2D was obtained as a dark brown solid (1.43 g). It was recrystallised three times from acetone-petroleum spirit (1:4) and once from ethanol-water (2:5) as white crystals (0.61 gm, 52.1% overall yield), m.p. 174–176° C. IR $v_{Max}$ 3060 (C–H), 1760 (ester C=O), 1680 (acid C=O) cm$^{-1}$. $^1$H NMR (CDCl$_3$) δ 6.89–8.12 (m, 6H, Ar–$\underline{H}$),

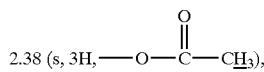2.38 (s, 3H, —O—C(=O)—C$\underline{H}_3$), ppm. M$^+$292; C$_{15}$F$_2$H$_{10}$O$_4$ requires 292.

(h) Synthesis of n-propionyldiflunisal (C3D). 0.024 mole (3.1 mL) of propionic anhydride was used in the acylation. Crude C3D was obtained as a yellow solid (1.38 g). It was recrystallised once from ethanol-water (2:5) and three times from acetone-petroleum spirit (1:4) as yellowish-white crystals (0.83 g, 67.5% overall yield), m.p. 140–142° C. IR $v_{Max}$ 3000 (C–H), 1750 (ester C=O), 1690 (acid C=O) cm$^{-1}$. $^1$H NMR (CDCl$_3$) δ 8.22–6.92 (m, 6H, Ar–$\underline{H}$),

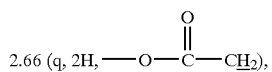2.66 (q, 2H, —O—C(=O)—C$\underline{H}_2$), 1.28 (t, 3H, C$\underline{H}_3$) ppm. M$^+$306; C$_{16}$F$_2$H$_{12}$O$_4$ requires 306.

(I) Synthesis of n-butanoyldiflunisal (C4D).

0.024 mole (3.9 mL) of butyric anhydride was used in the acylation. Crude C4D was 10obtained as a yellowish-white solid (0.95 g). It was recrystallised once from ethanol-water (2:5) and three times from acetone-petroleum spirit (1:4) as yellowish-white needles (0.57 g, 44.5% overall yield), m.p. 116–118° C. IR $v_{Max}$ 2980 (C–H), 1750 (ester C=O), 1680 (acid C=O) cm$^{-1}$. $^1$H NMR (CDCl$_3$) δ 8.21–6.92 (m, 6H, Ar–$\underline{H}$),

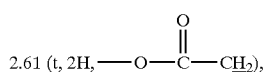2.61 (t, 2H, —O—C(=O)—C$\underline{H}_2$),

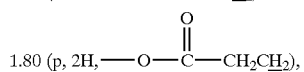1.80 (p, 2H, —O—C(=O)—CH$_2$C$\underline{H}_2$), 1.05 (t, 3H, C$\underline{H}_3$) ppm. M$^+$320; C$_{17}$F$_2$H$_{14}$O$_4$ requires 320.

(j) Synthesis of n-pentanoyldiflunisal (C5D).

0.02 mole (3.95 mL) of valeric anhydride was used in the acylation. Since valeric acid is slightly soluble in water, it was difficult to separate it from C5D by the methylene chloride extraction method (described in Scheme I). Therefore, a modified process was again designed. After reaction, the dark brown milky suspension was transferred to a 25 mL conical flask by a Pasteur pipette and cooled in ice and swirled continuously until a yellow solid of crude C5D (0.81 g) was obtained. It was recrystallised once from ethanol-water (2:5) and three times from acetone-petroleum spirit (1:4) as white plates (0.63 g, 47% overall yield), m.p. 101–103° C. IR $v_{Max}$ 2980 (C–H), 1725 (ester C=O), 1705 (acid C=O) cm$^{-1}$. $^1$H NMR (CDCl$_3$) δ 6.89–8.20 (m, 6H, Ar–$\underline{H}$),

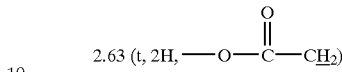2.63 (t, 2H, —O—C(=O)—C$\underline{H}_2$),

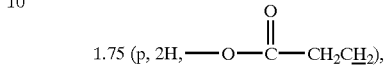1.75 (p, 2H, —O—C(=O)—CH$_2$C$\underline{H}_2$),

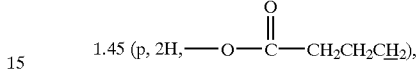1.45 (p, 2H, —O—C(=O)—CH$_2$CH$_2$C$\underline{H}_2$), 0.96 (t, 3H, C$\underline{H}_3$) ppm. M$^+$334; C$_{18}$F$_2$H$_{16}$O$_4$ requires 334.

(k) Synthesis of n-hexanoyldiflunisal (C6D).

0.02 mole (4.63 mL) of caproic anhydride was used in the acylation. Sice caproic acid is also slightly soluble in water, the method employed in C5D was utilized in this synthesis. Crude C6D was obtained after filtering and drying as a white pinkish solid (1.15 g). It was recrystallised once from ethanol-water (2:5) and three times from acetone-petroleum spirit (1:4) as white crystals (0.61 g, 43.9% overall yield), m.p. 105–106° C. IR $v_{Max}$ 2970 (C–H), 1725 (ester C=O), 1705 (acid C=O) cm$^{-1}$. $^1$H NMR (CDCl$_3$) δ 6.94–8.21 (m, 6H, Ar–$\underline{H}$),

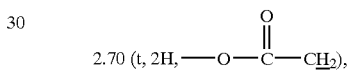2.70 (t, 2H, —O—C(=O)—C$\underline{H}_2$),

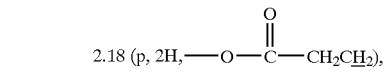2.18 (p, 2H, —O—C(=O)—CH$_2$C$\underline{H}_2$),

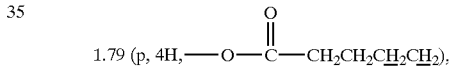1.79 (p, 4H, —O—C(=O)—CH$_2$CH$_2$C$\underline{H}_2$CH$_2$).

1.41 (t, 3H, C$\underline{H}_3$) ppm. M$^+$348; C$_{19}$F$_2$H$_{18}$O$_4$ requires 348.

(l) Synthesis of n-heptanoyldiflunisal (C7D).

0.005 mole (0.74 mL) of heptanoyl chloride was used in the acylation. Crude C7D was obtained as a light orange solid (0.61 gm). It was recrystallised three times from acetone-petroleum spirit (1:4) and once from ethanol-water (2:5) as white needles (0.35 g, 24.1% overall yield), m.p. 109–111° C. IR $v_{Max}$ 2940 (C–H), 1750 (ester C=O), 1680 (acid C–O) cm$^{-1}$. $^1$H NMR (CDCl$_3$) δ 6.94–8.37 (m, 6H, Ar–$\underline{H}$),

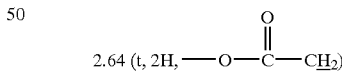2.64 (t, 2H, —O—C(=O)—C$\underline{H}_2$),

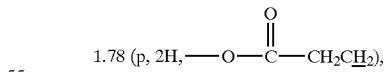1.78 (p, 2H, —O—C(=O)—CH$_2$C$\underline{H}_2$),

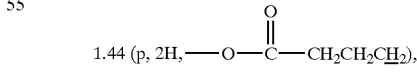1.44 (p, 2H, —O—C(=O)—CH$_2$CH$_2$C$\underline{H}_2$),

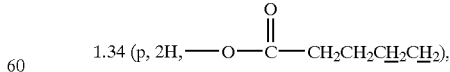1.34 (p, 2H, —O—C(=O)—CH$_2$CH$_2$C$\underline{H}_2$CH$_2$).

0.91 (t, 3H, C$\underline{H}_3$) ppm. M$^+$362; C$_{20}$F$_2$H$_{20}$O$_4$ requires 362.

Analytical

HPLC analytical method:

The HPLC method employed for the determination of the O-acyl salicylic acid and diflunisal derivatives was a modification of the methods of Mellick and Roberts 1996.

TABLE 1 shows the various constituents of the mobile phase, the internal standards, and flow rates used for detecting each particular compound in these series of derivatives. The eluent was monitored at 237 nm and sensitivity range 0.04 AUFs. In these solvent systems salicylic acid and diflunisal could also be assayed, with good separation from the other solute peaks.

HPLC Assay Validation:

Standard solutions of the derivatives were prepared both in Krebs-Henseleit buffer containing either no protein (for aspirin analogues) or 2% w/v BSA (for diflunisal esters) at pH 7.4. For C3SA to C5SA standard curves were prepared with concentrations ranging from 5–50 µg/mL. For C6SA–C8SA standard curves were prepared with concentrations ranging from 1–25 µg/mL. For C2D–C6D standard curves were prepared with concentrations ranging from 1–100 µg/mL. The standards and buffer samples (100 µL aliquots) were then prepared for HPLC analysis by addition of 20 µL of 35% perchloric acid and 200 µL of acetonitrile containing the internal standard. The solutions were thoroughly mixed (vortex mixer) and centrifuged (5 minutes at 9000 g), and then 20 µL of supernatant was injected onto the column. The peaks from the HPLC chromatogram were integrated and the peak area of the compound divided by the peak are of the internal standard to give the HPLC response. The within day coefficients of variation (CV) for the different derivatives were determined by establishing and running 3 separate standard curves on the same day. Identical unknown solute concentration by the mean of these concentrations. All samples and solutions were kept on ice prior to analysis to minimise hydrolysis.

Results:

FIGS. 1a and 1b show the relationship between HPLC retention time and carbon chain length in the O-acyl moiety. A linear relationship was found between the logarithm of the HPLC retention time and the number of carbon atoms in the ester side chain, reflecting the increase in lipophilicity as methylene groups are added to the side chain. For all compounds in this work HPLC standard curves were linear within the range of concentrations studied, with linear regression analysis yielding $r^2$ values>0.999. The within day coefficients of variation for all the compounds were within the range of 2.06 to 4.28% (n=3).

Solubility

This experiment was designed to investigate the intrinsic solubility of each compound at room temperature (25° C.). These studies were carried out in aqueous phosphoric acid (pH 1.5) and at 25±1° C. The pH conditions were chosen to ensure that the solubility of the unionised species was estimated. Given that the pKa of these esters will be similar to that of aspirin (pKa at 25° C.=3.5 (Foye, WO., 1989, In *Principles of Medicinal Chemistry* (3rd edition). Lea & Febiger/Philadelphia. London. p.863), a pH of 1.5 was chosen so that the compounds did not ionise appreciably.

Each derivative was added as an ethanol solution (100 µL) to a 15 mL siliconised screw-cap test tube (in duplicate). The solvent (9.9 mL) was then added to the test tube. The quantity of ester was chosen to be 4 times the predicted maximum solubility of the ester, based on aspirin solubility (0.0185 M at 25° C., The Merck Index 1983). For its analogues, the solubilities are expected to decrease by about 0.5 log unit/methylene group, (Yalkowsky, S H., 1981, In *Techniques of Solubilization of Drugs*, Marcel Dekker, New York Chapter 1). The test tube was sonicated for 15 minutes and centrifuged for 10 minutes (3000 g at 25° C.). An aliquot was filtered (Minisart 0.45 µm filter, Satorius) and diluted with HPLC mobile phase, then assayed. The tube was stored carefully in a 25° C. water bath after sampling and the remaining suspension was again sonicated and the process repeated 7 times at four hourly intervals. In these assays, standard curves were prepared by directly dissolving the esters in mobile phase. Concentrations for standard curves ranged from 1–50 µg/mL for all compounds. Furthermore, a manual injector (Waters Model U6K) was used (20 µL sample loop) which ensured that 20 µL was consistently injected onto the column and precluded the need for an internal standard.

In vitro non-enzymatic hydrolysis

These experiments were carried out both in Krebs-Henseleit buffer containing either no protein or 2% w/v BSA (bovine serum albumin, fraction V, Sigma) at pH 7.4 and 25±1° C. The results were used to investigate the hydrolysis of these derivatives in vitro and the influence of albumin on spontaneous hydrolysis.

Solutions of the derivatives in Krebs buffer (10 mL) was prepared in siliconised glass tubes. Each solution was sonicated for 5 minutes and centrifuged for 5 minutes (3000 g) at 25° C. to ensure maximum dissolution and to sediment any undissolved precipitate. About 7.5 mL of the supernatant was then transferred to a clean siliconised test tube and a 100 µL aliquot was removed and assayed. Samples were also removed from the solution at various times up to 46 hours (0.25, 2, 4, 19.5 and 46 hours) for C2SA and C3SA or 96 hours (0.25, 2.5, 5, 25,67 and 96 hours) in the case of C4SA to C8SA and the diflunisal esters. The rate of non-enzymatic hydrolysis (k) for each derivative was then estimated using the following equation:

$$C_t = C_0 exp(-kt) \quad (1)$$

where $C_1$ is the concentration of the ester at any time (t), and $C_0$ is the concentration of the ester at time zero. The half-life ($t_{1/2}$) was determined using the formula:

$$t_{1/2} = 0.693/k \quad (2)$$

Protein binding

These experiments were carried out in Krebs-Henseleit buffer containing 2% w/v BSA (pH 7.4) and incubated at 37° C. for 30 minutes.

A known concentration of the ethanolic (≤1%) aspirin analogue or diflunisal ester stock solution was added to the 2% BSA Krebs solution to make final concentrations of 125 µM, 250 µM and 500 µM.

The unbound fraction ($f_u$) of parent drug and its hydrolysis product were investigated using ultra-filtration: A 1.0 mL aliquot sample (in triplicate) was placed in a ultrafiltration tube (MPS-1, micro-partition system, Amicon) and centrifuged at 3000 g for 10 minutes. The ultra-filtrate was then assayed for parent drug and its hydrolysis product by HPLC.

To eliminate possible errors caused by hydrolysis, identical samples were placed in normal tubes and subjected to the same procedure. This control group (also in triplicate) was used to adjust for the percentage of hydrolysis in the ultra-filtrate under the experimental conditions.

The $f_u$ was determined as the ratio of the free concentration to total concentration of solutes. The binding constant (K) was determined from the slope of a Scatchard plot using following equation:

$$[Db]/[D] = -K[Db] + K[Pt] \quad (3)$$

where [Db] is the concentration of bound drug, [D] is the concentration of drug, [Pt] is the concentration of total protein, and v is the number of independent binding sites available. This equation is plotted as the ratio [Db]/[D]

versus [Db] and in this way the binding constant (K) is determined from the slope while vK[Pt] is determined from the intercept (Martin, 1983).

Results and Discussion

Synthesis

Overall yields:

Esters and aliphatic carboxylic acids are the two major components of the synthetic products. Because carboxylic acids are capable of forming hydrogen bonds with other molecules, they are good solvents for esters. Therefore, it was hard to recover solid esters from the reaction product mixtures after reactions. This situation became more difficult when the aliphatic moiety of carboxylic acid had more than four carbons. As a result, the ester could not be separated from the carboxylic acid by using an organic solvent to extract it from aqueous solution. Therefore, the longer the carbon chain length in the ester O-acyl moiety, the lower the overall yield.

Diflunisal esters had higher overall yields compared to their aspirin analogue counterparts. It is suggested that in comparison to aspirin analogues, the two benzene ring structure and larger molecular weight of diflunisal esters enabled them to crystallise more easily from the carboxylic acid.

Melting point:

The melting points of the aspirin analogues and diflunisal esters versus carbon chain length in the O-acyl moiety are presented in FIG. 2. The diflunisal esters followed the same trends as observed by Yalkowsky et al. (1972, *J. Pharm. Sci* 852–857) for the melting points of the alkyl p-aminobenzoates. This trend showed a fall in melting point as the side chain was increased from methyl to pentyl. The melting points then rose as the length of the side chain was increased from the pentyl to the decyl derivative (Yalkowsky et al., 1974, supra).

For the aspirin analogues, there are two minor exceptions to this trend (FIG. 2). The melting point of C5SA is higher than for C4SA and the melting point of C7SA is lower than for C6SA. C7SA has the lowest melting point (73° C.) for the aspirin analogues. Diflunisal esters have much higher melting points than those of aspirin analogues because of the increased molecular weight and aromatic stacking effects (Bailey and Bailey, 1981, *Organic Chemistry, Allyn and Bacon*, New York).

Spectroscopy:

All spectra showed C–H stretching bands near 3000 cm$^{-1}$, ester functional group bands near 1745 cm and carboxylic acid functional group bands near 1690 cm$^{-1}$. The spectra of aspirin analogues and diflunisal esters differ in the fingerprint regions. The IR spectra of the two starting materials, salicylic acid and diflunisal, reveal different stretching patterns from their ester derivatives. Their spectra show phenolic hydroxyl group stretching bands near 3290 cm$^{-1}$ but lack the carbonyl stretching frequency at 1745 cm$^{-1}$ characteristic of the ester functional group. NMR and mass spectra were consistent with the proposed structures.

Solubility

TABLE 2 lists the intrinsic solubilities for the aspirin analogues and diflunisal esters at 25±1° C. in water. Due to increased lipophilicity, the longer chain analogues have lower solubility than the shorter chain analogues. The measured solubilities of the shorter chain analogues (C3SA and C4SA) agree closely with the expected values which suggest that solubilities decrease by about 0.5 log unit/methylene group (Yalkowsky 1981, supra). However, the solubilities of the longer chain analogues are only about half of the expected value. The diflunisal esters are more lipophilic than aspirin analogues. Consequently, their solubilities in water were very low and, except for C2D and C3D. saturation concentrations were below the limit of detection for the HPLC method used.

Figure 3:
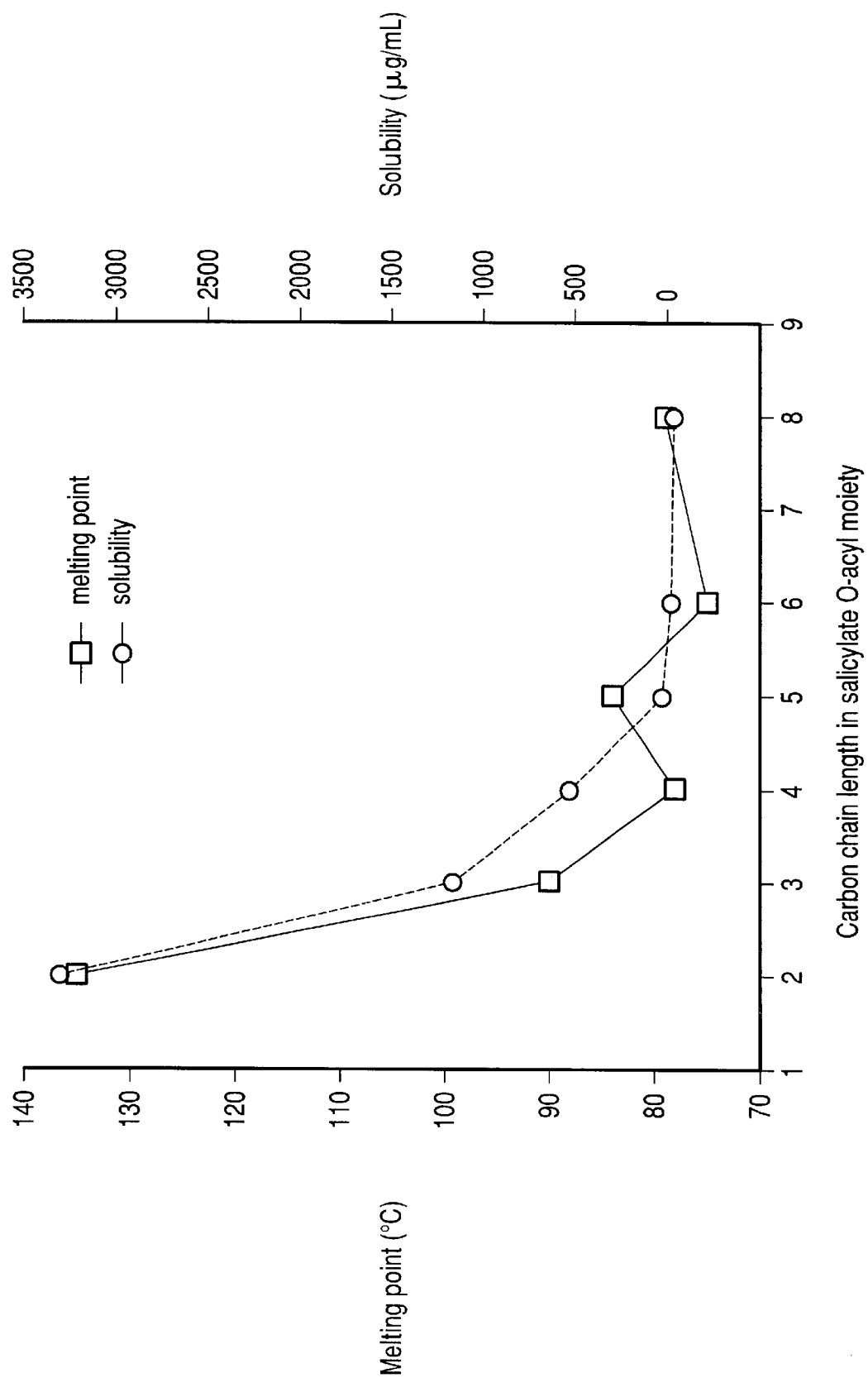
FIG. 3 illustrates the relationships between solubility, melting point and carbon chain length for the aspirin analogues.

Melting point data has previously been used to adequately predict drug solubilities for solutes belonging to the p-hydroxybenzoate homologous series (Forster et al., 1991, *Int. J. Pharm.*, 72 29–34). Therefore, the relationship between aqueous solubilities of the aspirin analogues and their melting points was investigated. FIG. 3 presents the relationships between solubility, melting point and carbon chain length for the aspirin analogues. We found the results to follow a similar trend.

The intrinsic solubility of diflunisal esters is extremely low (TABLE 2). The solubilities of these compounds in 2% BSA Krebs-Henseleit buffer (pH 7.4) at 25° C. are presented in TABLE 3. The more lipophilic the analogue, the higher the solubility of solute under these conditions.

In vitro non-enzymatic hydrolysis

Figure 4:
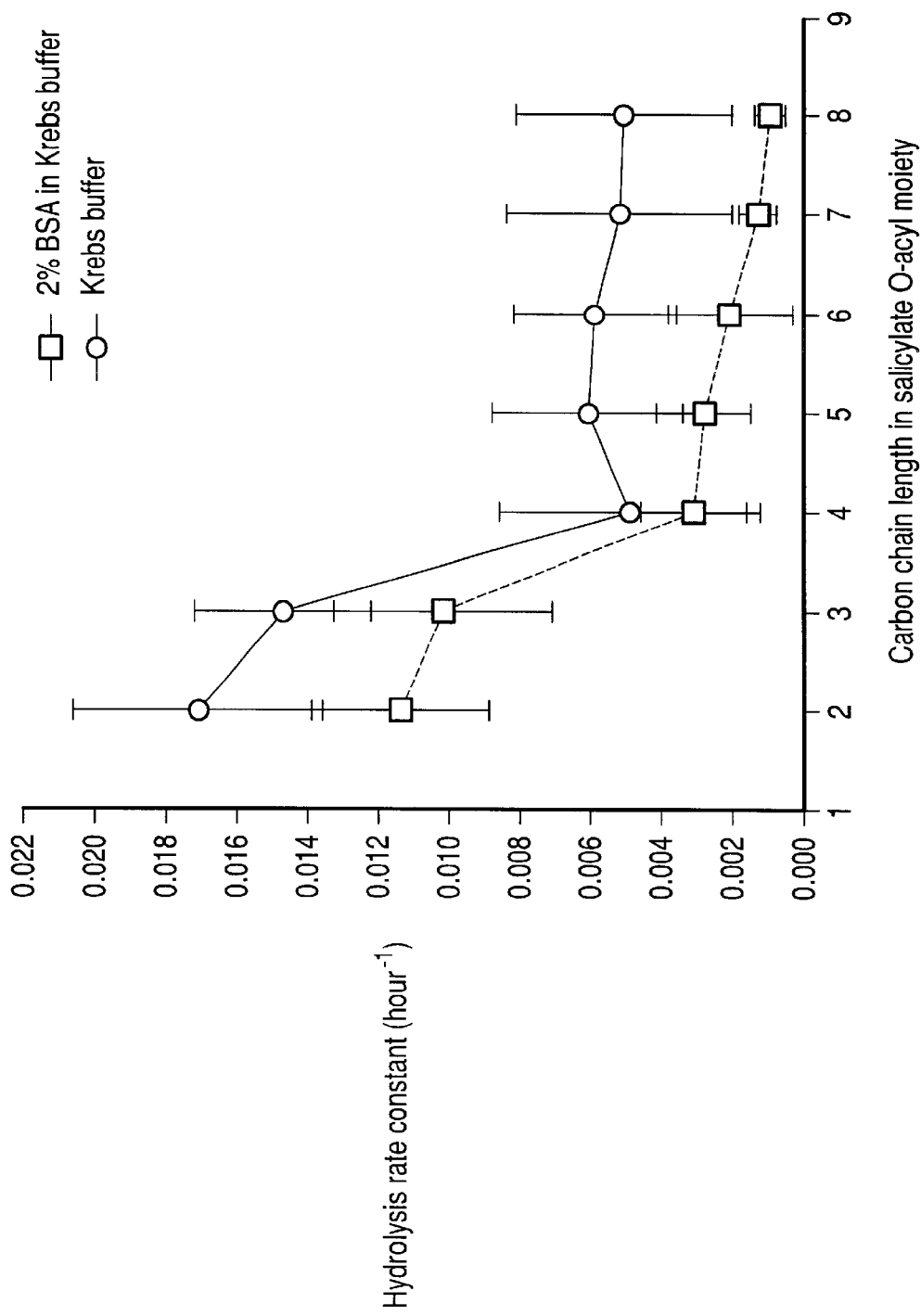
FIG. 4 shows the relationship between spontaneous hydrolysis rate constant and carbon chain length of the salicylate O-acyl moiety in Krebs buffer or 2% BSA Krebs buffer.

TABLE 4 shows the hydrolysis rate constants (k) and half lives ($t_{1/2}$) of the aspirin analogues and diflunisal esters in different solvents, while FIG. 4 presents the relationship between rate constant and carbon chain length of the salicylate O-acyl moiety. The greatly diminished hydrolysis rate constants for C4SA and C4D compared to their shorter chain counterparts suggests that some degree of steric hindrance exists when four or more carbon atoms are present in the side chain. Thus, hydrolysis is much slower for the longer chain esters. This is consistent with Newnan's empirical Rule of Six.

The diflunisal esters were found to be less stable than the aspirin analogues in Krebs-Henseleit buffer at 25° C. This can be explained by the 2.4-difluorophenyl moiety which is electron withdrawing group. This reduces electron density at the ester carbonyl group and increases the leaving group ability of the phenol, thus raising the susceptibility to hydrolysis. TABLE 4 shows that the diflunisal esters have shorter half-lives than their salicylate counterparts. As the half-lives of these solutes are lengthy (e.g. the half-life of C8SA in 2% BSA Krebs buffer is approximately 30 days), we have investigated only one half-life in this work.

In the presence of albumin, the hydrolysis rates for the aspirin analogues and diflunisal ester were decreased. Protein binding protected these compound against hydrolysis in vitro. In contrast, previous studies demonstrated that albumin enhanced the enzyme-catalysed hydrolysis of aspirin in whole blood by an activating effect of β-glucuronidase (Levy et al., 1966, In *Glucuronic Acid*. Academic Press, New York p. 301; Aarons et al., 1980, *J. Pharm. Pharmacol.*, 32 537–543). Hence, it is possible that in vivo, albumin may activate the enzyme-catalysed hydrolysis of these compounds.

Protein binding

Figure 5A:
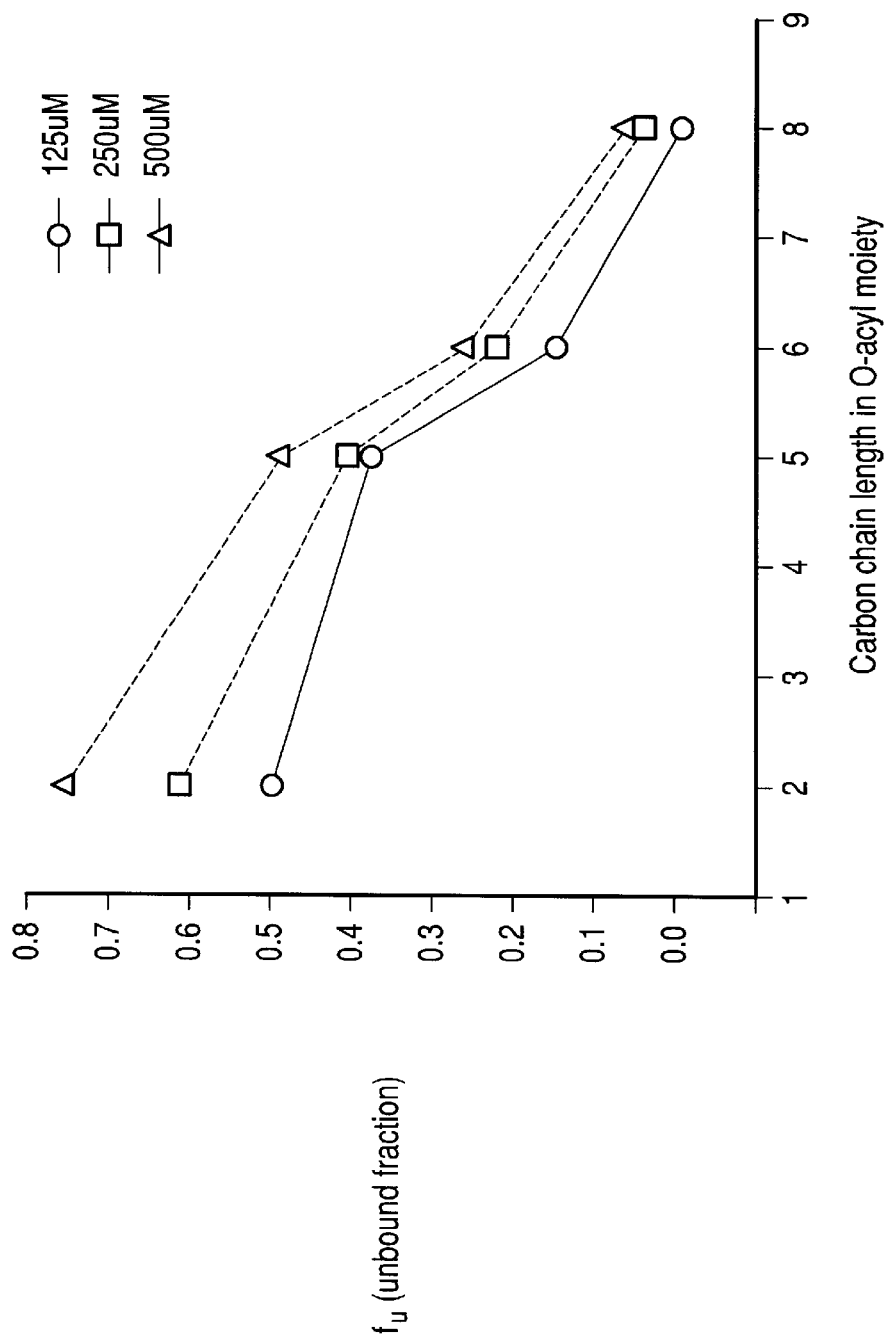

It is generally accepted that the unbound concentration of drugs has consequences for the disposition and pharmacological activity of the drug (Jusko et al., 1976, *Drug Metabolism Review* 5 43–140; Yacobi et al., 1977, *J. Pharm. Sci.* 66 567–572). Therefore, there is a need to study protein binding of these compounds (including their hydrolysis products, salicylic acid and diflunisal). FIGS. 5a and 5b show the unbound fraction ($f_u$) of the aspirin analogues and diflunisal esters versus carbon chain length at various concentrations. It is apparent that the most lipophilic compounds have the lowest f, values. Thus, the strength of protein binding increases in proportion to lipophilicity.

TABLE 5 presents the binding constant (K) of the aspirin analogues and diflunisal esters. According to this table, the strength of protein binding among the aspirin analogues is in the following order: C8SA>C6SA>C5SA>C2SA and the diflunisal esters is in the following order: C6D>C5D>C4D>C2D.

EXAMPLE 2

Reduced Ulcerogenic Potential and Higher First-Pass Detoxification of O-Acyl Derivatives of Salicylic Acid and Diflunisal compared to Aspirin Methods Synthesis:

O-acyl derivatives of salicylic acid and diflunisal were prepared as above. The respective structures relating thereto were confirmed by infra red, nuclear magnetic resonance and mass spectroscopy. Differential scanning calorimetry was employed to assess the purity of each compound (>98% for all esters).

Gastrotoxicity:

This was assessed in disease-stressed polyarthritic rats (Rainsford et al, 1992, *J. Pharm. Pharmacol.* 44 476–482) under a procedure approved by the Animal Ethics Committee at the University of Queensland (MED 504/94; 610/95).

Female Wistar rats (200±10 g) were given 0.5 mg/mL heat-killed and delipidated *Mycobacterium tuberculosis* (mixed human strains) suspended in 0.05 mL squalane (Sigma) by subcutaneous injection into the tailbase to elicit polyarthritis (Whitehouse et al, 1974, *Immunology* 27 311–330). The animals were used 14–18. days following induction of the disease at which stage the polyarthritis was optimally expressed. Exposure to such inflammatory insults and physical stress markedly sensitizes the gastric mucosa to the ulcerogenic effects of non-steroidal anti-inflammatory drugs.

Animals were placed in all-wire mesh cages in groups of 3 each, deprived of food but allowed free access to water, for 16 hours before experimentation. The compounds were administered orally as 2 mL fine aqueous suspensions prepared by homogenization immediately before use.

Two hours after the compounds were administered, the animal were killed by cervical dislocation, then stomachs excised and thoroughly rinsed and the gastric lesion indices determined as described below: The number (N) and severity (S, graded on a scale of 10 to 4+ based on increasing are of injury) of gastric lesions as well as the percentage of animals with gastric damage (% I) was recorded. the lesion index (LI) was computed as:

$$LI = N/n + S/n + I/10$$

where n=number of animals per group

Anti-platelet Effects.

Platelet aggregation studies were carried out using a single channel Lumiaggregometer (Chrono-Log Company, Haverton, Pa.) at 37° C. using human platelet-rich and platelet-poor plasma. Platelet-rich plasma (PRP) with a platelet concentration of 250,000 per mL (measured with a Coulter counter) was prepared by centrifuging 3.8% citrated plasma (1:9) at 1,500 rpm using a (Beckman) benchtop centrifuge at room temperature for 15 minutes. Platelet-poor plasma (PPP) was prepared by further centrifuging residual blood from platelet-rich plasma at 3,000 rpm for 30 minutes. Platelet-poor plasma was also confirmed b y Coulter counting for platelet content.

Platelet aggregation studies were preceded by pipetting 0.4 mL platelet-rich plasma into a stirred aggregometer tube and calibrate to 90% of recorder. Platelet-poor plasma was set to calibrate at 10% of recorder. Platelet aggregation was initiated by the addition of a arachidonic acid (Sigma) or ADP (Sigma).

10 mM solutions of each compound (TABLE 6) were prepared in 1 mL of normal saline solution (containing 4% BSA) before use. An aliquot (400 $\mu$L) of platelet-rich plasma was pipetted into a stirred aggregometer tube at 37° C. and 30 $\mu$L of test sample added simultaneously. This mixture was preincubated for varying period (3 to 45 minutes), then arachidonic acid (AA) was added (final conc.=200 $\mu$M) to initiate platelet aggregation. If no aggregation occurred, 20 $\mu$M ADP was added to confirm the vitality of the platelets (if the platelets are vital, ADP will induce this AA-test sample-plasma mixture to aggregate). This procedure is necessary to investigate whether the non-aggregation phenomenon is due to drug inhibition or simply due to inviable platelets (unable to respond to AA). The degree of aggregation was measure by calculating the area under the turbidimetric response curve (AUC). The AUC of platelet-free normal saline solution was assigned to be 0% aggregation and the AUC of platelet suspension (drug-free) to be 100% aggregation.

It is generally accepted that aspirin inhibits platelet cyclooxygenase through an irreversible acetylation process. In separate experiments, the platelet acylation by these O-acyl salicylates was investigated. It is hypothesised that if the acylation were reversible, then the O-acyl moieties might be removed by platelet washing. Consequently, the washed platelets would become susceptible to aggregation by arachidonic acid.

A platelet-washing technique, ADGS (albumin density gradient separation) similar to one used by Spriggs and Alexander (Spriggs, 1960, *Nature* 188 863), was employed for this purpose. The principle underlying ADGS is simply that of centrifuging platelets into a continuous density gradient produced by mixing the interface between platelet-rich plasma and 40–45% bovine serum albumin. Thereby the platelets are gently sedimented into a zone with a specific gravity equal to their own, and they are protected by the cushion of albumin from disruptive squashing on the hard surface of the centrifuge tube.

Flat-bottomed, polystyrene tubes of 10 mL capacity with stopper were used for platelet washing by ADGS. Pasteur pipettes were siliconised and used for transferring plasma and wash fluid. Stirring rods were made from Pasteur pipettes by heating the tips, forming a right-angle ben approximately 1 cm long and then siliconised. To make a 40–45% (w/v) aqueous solution, 5 gm of bovine serum albumin (Sigma) was layered over the top of 10 mL distilled water in an Ehrlenmeyer flask which is covered with parafilm and left standing without stirring at 4° C. for 48 hours. After the albumin was dissolved, the solution was brought to neutral pH with NaHCO$_3$. The solution was then pipetted in 1 mL aliquot into 10 mL plastic tubes and stored at −20° C. until use.

The solution used for washing platelets by ADGS was a modified form of calcium-free Tyrode's solution (NaCl, 8.0 gm/L; KCl, 0.2 g./L; NaH$_2$PO$_4$.2H$_2$O, 0.065 gm/L; MgCl$_2$.6H$_2$O 0.415 gm/L; NaHCO$_3$, 1.0 gm/L; dextrose, 1.0 gm/L), pH 7.3, prepared the same day it was used.

7.5 mL of platelet-rich plasma was pipetted into a plastic tube, then 0.525 mL (7.5 mL: 400 $\mu$L=X:30 $\mu$L, X=0.525 mL) of 10 mM C2S (aspirin) or C6S (O-hexanoylsalicylic acid) was added to the tube. Subsequently, this drug-plasma mixture was incubated at 37° C. with gently shaking for 3 minutes (10 minutes for C6S). Afterwards, aliquots (400 $\mu$L) of this mixture were pipetted into a stirred aggregometer tube at 37° C. and 200 µM of arachidonic acid was added to initiate platelet aggregation. The results confirmed that the platelets had been non-reversibly inhibited by prior exposure to C2SA or C6SA.

The rest of drug-plasma mixture (7.1 mL) was pipetted into a tube containing 1 mL frozen albumin. The interface between the albumin and the drug-plasma mixture was gently agitated with a siliconised rod (with vertical movements over a distance of approximately 1 cm) for approximately 30 seconds until a density gradient approximately 1 cm broad was produced. The tube was then stoppered and centrifuged at room temperature for 15 minutes at 3,000 rpm. The platelets were thereby sedimented into a band approximately 0.5 cm broad. The relatively platelet-poor plasma in the supernatant was then removed with a siliconised Pasteur pipette. The remaining platelets and albumin were resuspended in 7 mL calcium-free Tyrode's solution by gentle inversion of the stoppered tube. The washing procedure was repeated twice.

Aliquots (400 µL) of washed platelet-rich Tyrode's solution was pipetted into a stirred aggregometer tube at 37° C., then 200 µM arachidonic acid was added to initiate platelet aggregation and 20 µM ADP was added to check the vitality of the washed platelets.

In-situ Rat Liver Perfusions.

The hepatic availability ($F_{hepatic}$) for the O-acyl esters of the salicylic acid and diflunisal was determined using a once through in-situ perfused rat liver preparation (Mellick et al, Unpublished Results).

Protein-free Krebs-Henseleit buffer was perfused at 30 mL/min for aspiring analogues and 2% BSA in Krebs-Henseleit buffer for diflunisal esters (since the solubilities of these latter compounds in protein-free media were very low (Hung et al, supra), 2% BSA were used to increase their solubilities). Briefly, 50 µL aliquots of a saturated solution of the particular O-acyl salicylic acid or diflunisal in Krebs-Henseleit buffer (or with 2% BSA) was injected into the liver with perfusate outflow samples collected via a fraction collector over three minutes. Aliquots (100 µL) from the outflow samples were assayed by HPLC to determine the residual concentration of presented ester and the quantity of phenolic metabolite (salicylic acid or diflunisal) issuing from the perfused liver. The HPLC assay was a modification of the method used by Mellick & Roberts 1996 (Mellick et al, 1996, unpublished results). A Brownlee C18 column (250×4.6 mm) was employed with a mobile phase consisting of 18:80:1 (acetonitrile: 0.03% (v/v) phosphoric acid:triethylamine) at pH 2.0 for C2SA to C3SA or 49:50:1 for C4SA to C8SA or 64:35:1 for C2D to C7D (except for C3D or 34:65:1 for C3D.

The hepatic availability (F) was determined from the outflow concentration versus time profiles for the esters using equation 1, with the assistance of the Moments Calculator 2.2 program for Macintosh computer developed by Robert Purves.

$$F=Q.AUC/D \quad (1)$$

where Q is the perfusate flow rate and D is the dose of aspirin analogues or diflunisal esters administered. The area under the concentration-time curve (AUC) was estimated by the trapezoidal rule integration with appropriate modification for tail (Mellick et al, supra).

Results

Figure 6B:
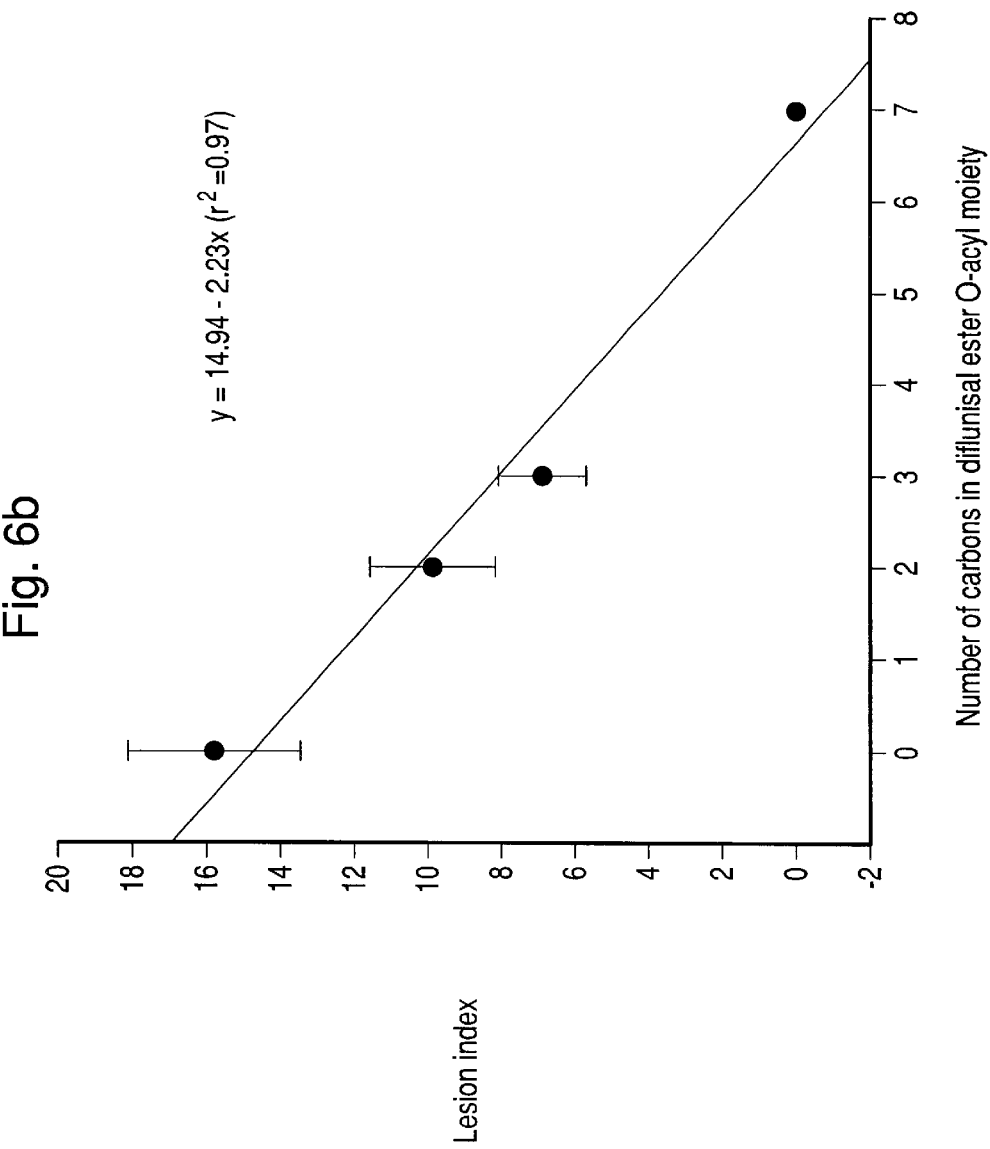

Gastrotoxicity: FIGS. 6a and 6b show that when orally administered, the more lipophilic (longer O-acyl carbon side chain) salicylic acid or diflunisal phenolic esters caused considerably less damage than their shorter chain analogues ($r^2$=0.74 for salicylic acid derivatives; $r^2$=0.97 for diflunisal derivatives) to the gastric mucous in this most sensitive ulcer model (employing diseased and fasting animals).

Figure 7:
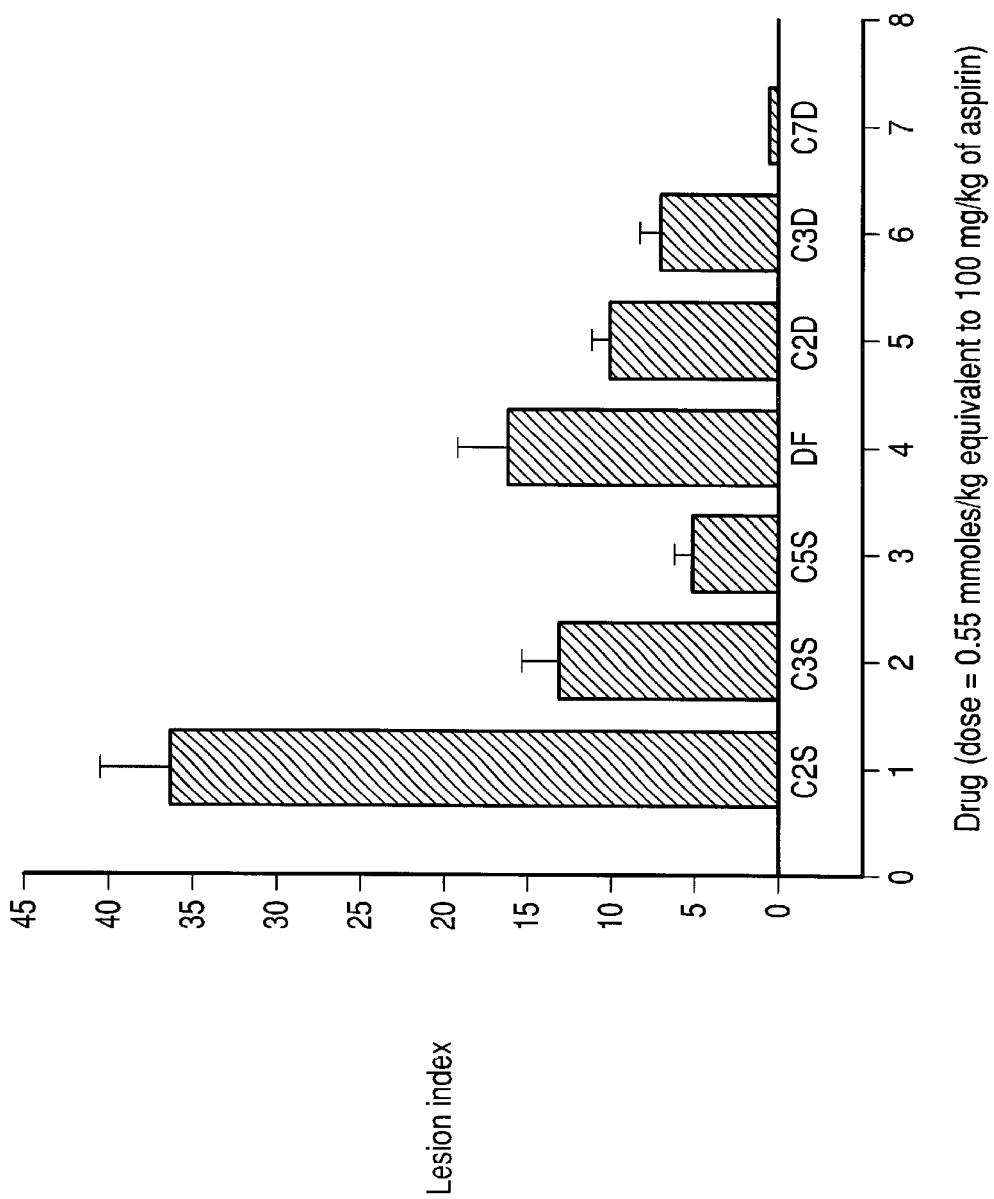
FIG. 7 illustrates a comparison of gastric lesion indices for various salicylates in disease-stressed rats.

FIG. 7 shows that when orally administered, aspirin caused far more gastric mucosal injury than any other compounds included in this study. Histological evaluation confirmed the almost total absence of lesions in stomachs taken from rats treated with 50 mg/Kg of C7D (the most lipophilic compound in this study) which is equivalent to 100 mg/Kg of aspirin.

Figure 8:
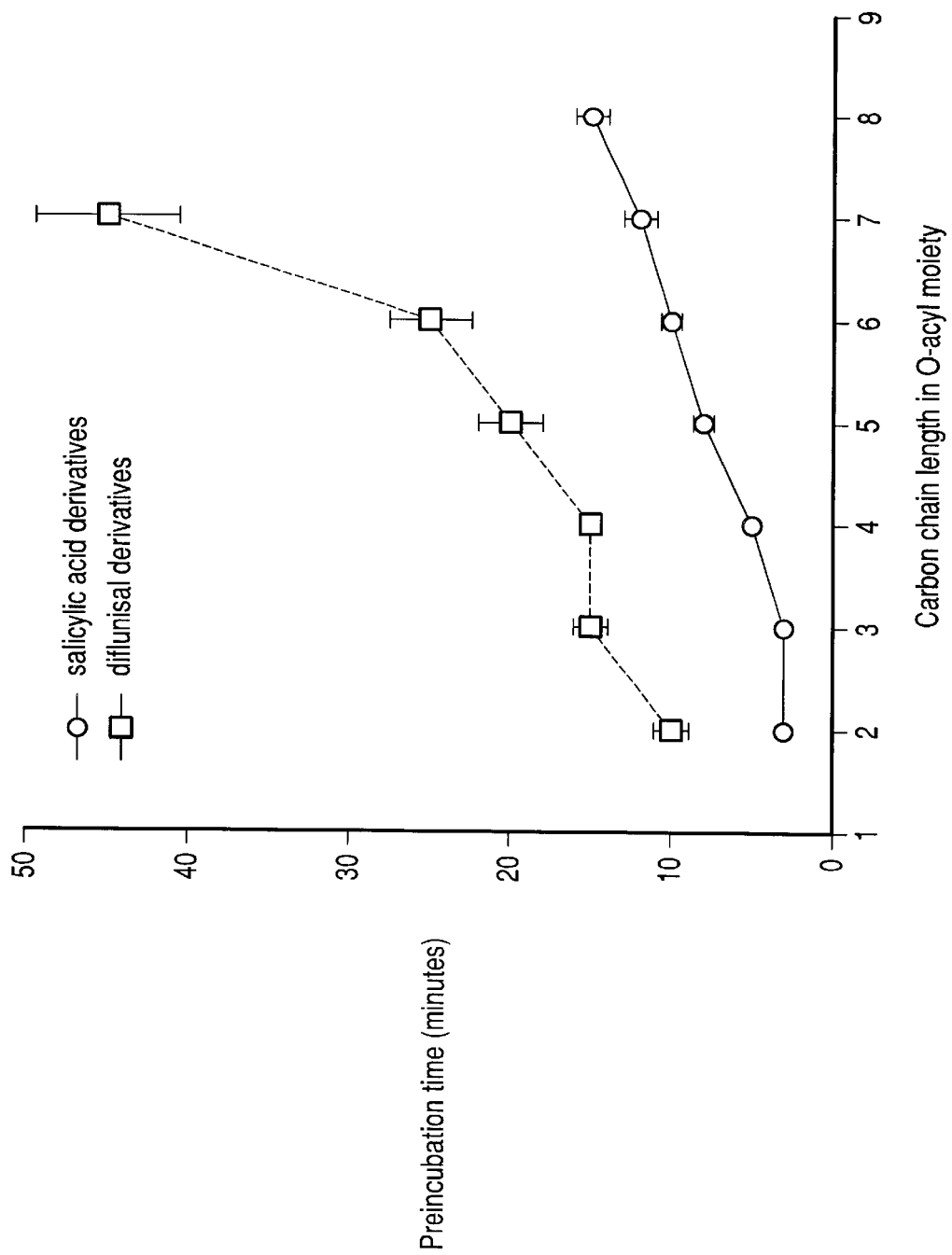
FIG. 8 shows the relationship between the length of the carbon chain in the O-acyl moiety and the preincubation time required for anti-aggregating activity.

Anti-platelet Effects:

The antiplatelet effects of aspirin analogues and diflunisal esters were studies on the aggregation of human platelet rich plasma induced by arachidonic acid (200 µM). TABLE 7 presents that all the compounds described here showed significant antiplatelet activity, equivalent to that shown by equal concentrations of aspirin, against arachidonate-induced aggregation. Subsequent exposure to ADP confirmed the vitality of platelets. FIG. 8 shows the relationship between the length of the carbon chain in the O-acyl moiety and the required preincubation time. The longer chain derivatives required longer preincubation time, consistent with increased lipophilicity.

The platelet washing study showed that platelets pretreated with C6SA (a representative lipophilic salicylate) or C2SA (aspirin) were still refractory to arachidonic acid, failing to aggregate after two-fold washing. Subsequent aggregation by ADP confirmed the washed platelets retained vitality.

In-situ Rat Liver Perfusions:

TABLE 8 lists the hepatic availability (F) results from this study. It shows that the residual availability (F), after hepatic extraction of salicylic acid derivatives, decreased with increasing carbon number in the O-acyl group. However, the relationship between hepatic availability and carbon number in the diflunisal esters in more complex, in contrast to the salicylic acid derivatives. A confounding factor arises from the need to include 2% BSA in the perfusate to ensure adequate solubility of these diflunisal esters. To circumvent this complication and compare these two homologous series, it is necessary to analyse the hepatic availability results more extensively.

Discussion

The use of aspirin as an anti-platelet drug is limited by its propensity to induce gastric injury and by its adverse effect on vascular prostacyclin formation. In this study we have tested the hypothesis that modification of two phenolic NSAIDS (salicylic acid and diflunisal) by esterification with a series of O-acyl moieties would reduce their gastrotoxicity, but had preserved anti-platelet activities as aspirin. The short-term ulcerogenic, anti-platelet properties and hepatic elimination of these phenolic esters have been investigated. The results show that the relative lack of ulcerogenic effects may have been attributable to a reduction in the topical irritant properties of these compounds relative to aspirin, as opposed to any systemic effects of the derivatives. The anti-platelet studies show that diflunisal esters need longer preincubation time than their salicylate analogues. This may reflect that they are more lipophilic than corresponding O-acyl salicylates. The results also indicate that structure-pharmacokinetic relationships existed among the aspirin analogues and diflunisal esters. The longer chain derivatives required longer preincubation time, consistent with increased lipophilicity. The platelet washing studies suggest that platelet cyclooxygenases are acylated irreversibly acylation being apparently independent of the carbon chain length in the O-acyl moiety.

We have determined the hepatic availability (F) for the salicylic acid and diflunisal derivatives under specific conditions (perusate flow rate (Q)=30 mL/min with 0 or 2% BSA in the perfusate). However, in vivo, the hepatic flow of the blood in the rat is around 10 mL/min (Richardson et al, 1981, *Gastroenterology* 81 356–375) and the albumin concentration is approximately 650 $\mu$M (Vander, 1986, Human Physiology (4th ed.)). The dispersion model can be used to predict the in vivo hepatic availability of these compounds.

According to the dispersion model of hepatic elimination (Roberts et al, 1990, *J. Pharmacokin. Biopharm.* 18 209–234) the hepatic availability (F) of an extracted solute is given by the equation (2):

$$F = \exp\left[\frac{1-a}{2D_N}\right] \quad (2)$$

where $a=\sqrt{1+4R_N D_N}$, $D_N$ is the dispersion number which describes the spread of solute residence times in the liver. $R_N$ is the efficiency number which characterises the elimination of solute by the liver and is defined by the equation:

$$R_N = \frac{f_{ub} PCL_{int}}{Q(P + CL_{int})} \quad (3)$$

where $f_{ub}$ is the unbound fraction of solute in the blood, P is the hepatocyte's permeability to the solute, $CL_{int}$ is the intrinsic clearance of the liver, and Q is the perfusate flow rate. Given that the protein-binding characteristics of these derivatives have been studied and a knowledge of $D_N$ for the rat liver under the conditions of this study have been reported elsewhere (Mellick et al, supra), we can use equations (2) & (3) to predict the in vivo hepatic extraction for the salicylic acid and diflunisal derivatives.

Figure 9:
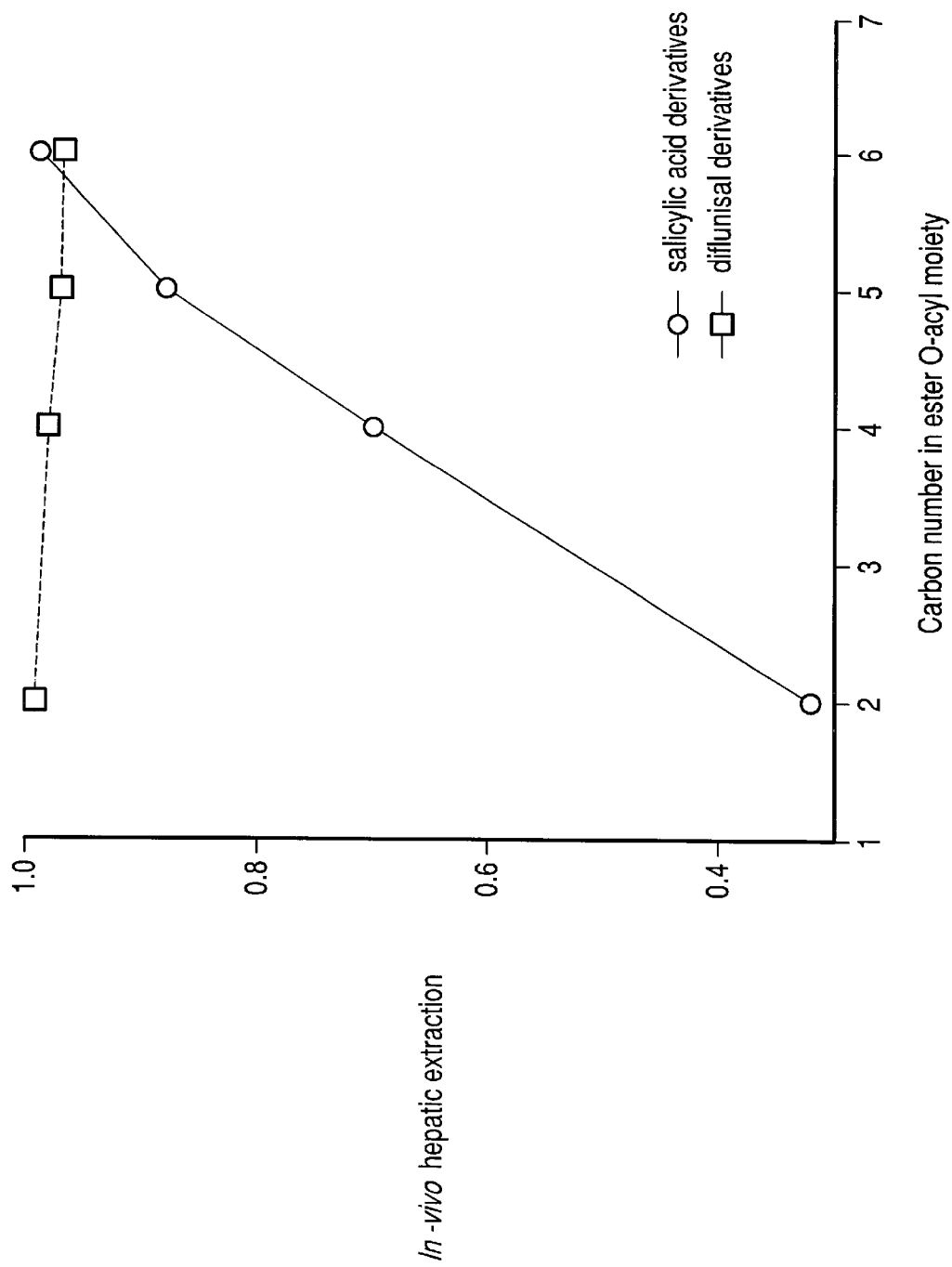
FIG. 9 shows a prediction of in-vivo hepatic extraction versus carbon chain length in the O-acyl moiety.

FIG. 9 shows that the systemic availability after first-pass clearance by the liver of these O-acyl derivatives are significantly less than aspirin. Hence, the greater rate of hepatic elimination may minimise the exposure of the systemic circulation to these orally administered esters; thereby (I) minimising prostacyclin inhibition within the vessel endothelium; and (ii) restricting anti-platelet action to pre-hepatic clearance (ie. within the portal vein).

Figure 10:
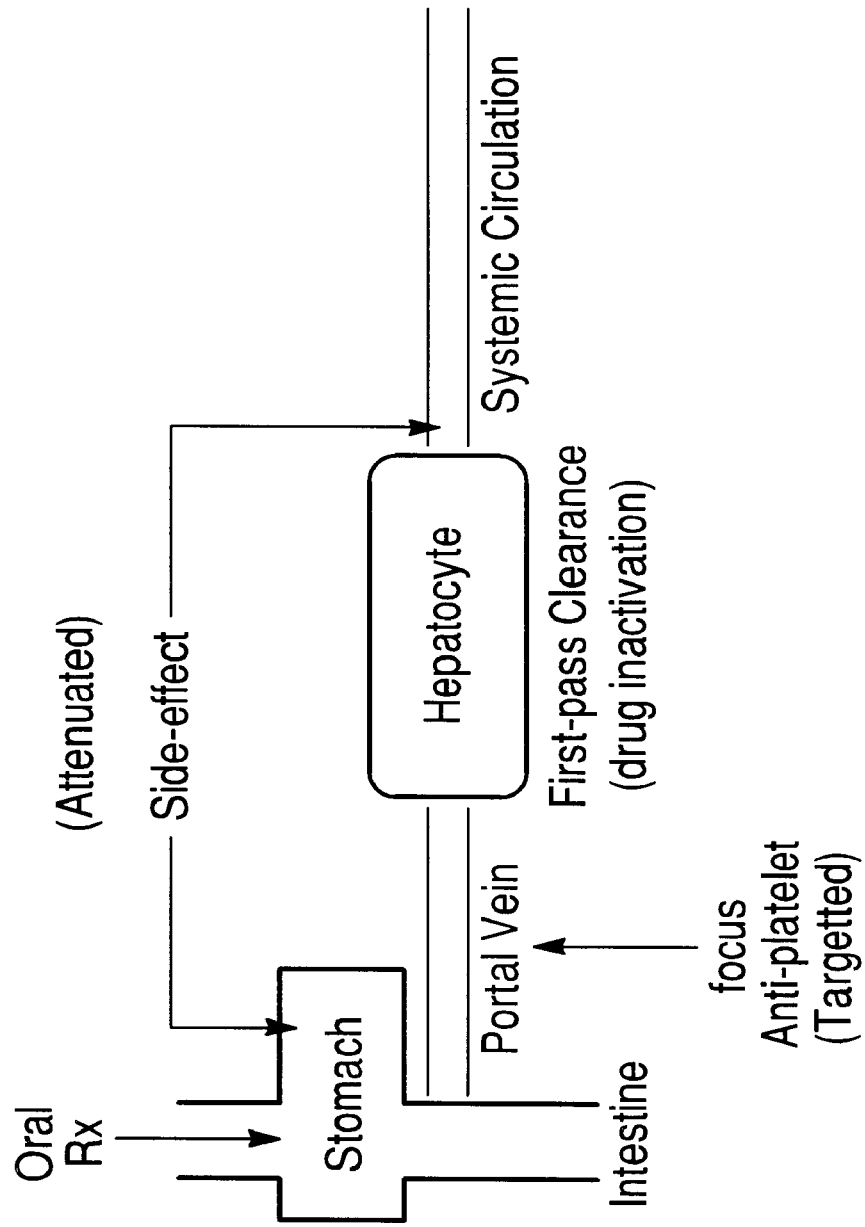
FIG. 10 represents a schematic of a topographic overview which shows that focussing anti-platelet activity to the portal circulation depends on extensive hepatic de-acylation of the compounds, forming platelet-inactive salicylate.

It is concluded that this series of aspirin homologues, namely O-acyl derivatives of salicylic acid or diflunisal, caused less short-term gastric injury in diseased-stressed rats compared to aspirin, but still exhibited a capacity to inhibit platelet aggregation. The systemic availability of these agents after first-pass clearance by the liver decreased with increasing lipophilicity. Such agents might therefore be expected to have a less deleterious effect on prostacyclin production in the post-hepatic blood vessels than aspirin. Accordingly, increasing the hepatic elimination in this way would diminish unwanted effects in the systemic circulation (FIG. 10) and enhances their potential as platelet targeted anti-thrombotic agents. Furthermore, because of their rapid hepatic transformation to minimally toxic metabolites (salicylate, diflunisal and simple fatty acids), these O-acyl derivatives of diflunisal and salicylic acid may be more acceptable as alternatives to aspirin for platelet regulation than specifically designed anti-thromboxane xenobiotics.

EXAMPLE 3

Studies Relating To Hepatic Disposition Of O-acyl Derivatives of Diflunisal

Materials and Methods

Analytical Apparatus:

High-performance liquid chromatography (HPLC) was as described for Example 2.

HPLC analytical method:

The HPLC method employed for the determination of the O-acyl diflunisal derivatives was a modification of the method for assaying aspirin described by Mellick et al. (1996, submitted for publication). The mobile phase used in these HPLC studies consisting of 64:35:1 (acetonitrile: 0.03% (v/v) phosphoric acid:triethylamine) at pH 2.0 (flow rate 1 mL/min) and 0.004% w/v salicylic acid in acetonitrile as internal standard. The effluent was monitored at 237 nm. In this solvent system diflunisal was also assayed, with good separation from the other solute peaks.

HPLC Assay Validation:

Standard solutions of the derivatives were prepared in 2% BSA Krebs-Henseleit buffer (pH 7.4) at concentrations ranging from 1–100 $\mu$g/mL. The maximum solubility of these compounds was previously determined for Example 1. The standards and buffer samples (100 $\mu$L aliquots) were then prepared for HPLC analysis by addition of 20 $\mu$L of 35% perchloric acid and 200 $\mu$L of acetonitrile containing the internal standard. The solutions were thoroughly mixed (vortex mixer) and centrifuged (5 minutes at 9000 g), and then 20 $\mu$L of supernatant was injected onto the column. The peaks from the HPLC chromatogram were integrated and the peak area of the compound divided by the peak area of the internal standard to give the HPLC response. The within day coefficients of variation (CV) for the different derivatives were determined by establishing and running 3 separate standard curves on the same day. Identical unknown samples were also run and the exact concentration determined using the separated standard curves. The CV was determined by dividing the standard deviation of the determined unknown solute concentration by the mean of these concentrations. All samples and solutions were kept on ice prior to analysis to minimize the chance of spontaneous hydrolysis.

In-situ rat liver perfusions:

Mature female Sprague-Dawley rats were obtained from the University of Queensland Animal Breeding Facility and weighed between 180–270 grams. The animals were given access to a standard laboratory diet prior to experiment. Rats were anaesthetised by interperitoneal injection of pentobarbital sodium (60 mg/kg, Boehringer Ingelhein). Following laparotomy animals were heparinized (heparin sodium, David Bull Laboratories Australia, 200 units) via the inferior vena cava. The bile duct was cannulated with PE10 (Clay Adams, New Jersey). 0.025 gm/L taurocholic acid (Sigma Co., USA.) was dissolved in perfusate to stimulate bile production. The portal vein was then cannulated using a 16 G intravenous catheter and the liver was perfused via this cannula with 2% BSA Krebs-Henseleit bicarbonate buffer (pH 7.4) and oxygenated using a silastic tubing lung ventilated with carbogen (95% $O_2$/5% $CO_2$). The perfusion system used was non-recirculating and employed a peristaltic pump (Cole-Parmer, Illinois).

After perfusion was effected the animals were sacrificed by thoracotomy and the thoracic inferior vena cava was cannulated with PE 240 (Clay Adams, New Jersey). The animal was placed in a temperature controlled perfusion cabinet at 37° C. Liver viability was assessed by oxygen consumption, bile flow, diflunisal esters' extraction and macroscopic appearance. TABLE 9 shows the perfusion conditions and viability parameters.

Bolus studies:

Perfusions were made at 30 mL/min in each liver. After a 10 minute perfusion stabilization period, injectate (50 µL) containing Evans Blue (3 mg/mL) and [$^3$H]-water in a saturated solution of the particular O-acyl diflunisal ester or pregenerated diflunisal (which was injected as parent compound) in 2% BSA Krebs-Henseleit buffer, was injected into the liver with outlet samples collected via a fraction collector over one minute.

Aliquots (100 µL) of pooled perfusate samples were taken for Evans Blue spectrophotometric analysis and [$^3$H]-water scintillation counting before adjusting pH. These pooled samples were then acidified to pH 2.0 by addition of 1 M HCl and extracted into 2.5 volumes of ether. The extraction mixture was soon afterward cooled to −20° C. in the freezer, which resulted in the solidification of the aqueous phase. The ether fraction was then removed and reduced to approximately 100 µL by evaporation under air and prepared as before for HPLC analysis. A known concentration of each buffer solution of ester was concurrently extracted and assayed with the perfusate samples to assess the degree of spontaneous hydrolysis occurring over the duration of the extraction procedure. This non-enzymatic hydrolysis was converted for in the analysis. The total recovery of diflunisal esters extracted using this technique was >90%.

Moments analysis:

The F, MTT and CV$^2$ for the diflunisal esters (or pregenerated DF) and the reference solutes (EB and [$^3$H]-water) were determined from the outflow concentration versus time profile using equation (1)–(4), with the assistance of the Moments Calculator 2.2 program for Macintosh computer developed by Robert Purves (Purves RD, 1994, *J. Pharm. Sci.* 83 202–205).

$$F = \frac{Q \cdot AUC}{D} \tag{1}$$

$$MTT = \frac{AUMC}{AUC} \tag{2}$$

where Q is the perfusate flow rate, D is the dose of diflunisal esters administered. The area under the concentration-time curve (AUC) and the first moment curve (AUMC) were estimated by the trapezoidal rule integration with appropriate modification for tail (Mellick et al., 1996, submitted for publication).

$$CV^2 = \frac{\sigma^2}{MTT^2} \tag{3}$$

where $$\sigma^2 = \frac{\int_0^\infty t^2 C(t)\, dt}{\int_0^\infty C(t)\, dt} - MTT^2 \tag{4}$$

All data is presented as mean ± standard error unless otherwise stated. A P<0.05 was taken as significant.

Dispersion model analysis:

The moment data was further examined using the dispersion model of hepatic elimination which defines F of an extracted solute by the equation (Roberts et al., 1990, *J. Pharmacokin. Biopharm.* 18 209–234):

$$F = \exp\left[\frac{1-a}{2D_N}\right] \tag{5}$$

where $$a = \sqrt{1 + 4R_N D_N} \tag{6}$$

$D_N$ is the dispersion number which describes the spread of solute residence times in the liver following bolus input and equal half the normalized variance for a non-extracted reference indicator $$\left(\frac{CV^2}{2}\right)$$

(Roberts et al., 1990).

$R_N$ is the efficiency number which characterises the elimination of solute by the liver and is defined by the equation:

$$R_N = \frac{f_{ub} P CL_{int}}{Q(P + CL_{int})} \tag{7}$$

where $f_{ub}$ is the unbound fraction of solute in the blood, P is the hepatocyte's permeability to the solute, $CL_{int}$ is the intrinsic clearance of the liver (defined as $$CL_{int} = \sum_{i=1}^{n} \frac{V_{m,i}}{K_{m,i}}$$

(Gillette, 1971, *Ann. N. Acad. Sci.* 179 43–61)), and Q is the perfusate flow rate. If F for a solute and the CV$^2$ for a non-extracted reference solute (eg. EB) are known, we can solve for "a" using equation (5) and then for "$R_N$" using equation (6).

The dispersion model expressions (Roberts et al., 1990) for MTT and CV$^2$ are presented in equations (8) and (9).

$$MTT = \frac{V_b}{Q_a}\left[1 + \frac{f_{ub} V_C P^2}{f_{uc} V_B (P + CL_{int})^2}\right] \tag{8}$$

$$CV^2 = \frac{2D_N}{a} + 2a \frac{V_c^2 P^2 f_{ub} Q(P + CL_{int})}{(V_B f_{uc}(P + CL_{int})^2 + V_c f_{ub} P^2)^2} \tag{9}$$

where $V_B$ and $V_C$ are the volume of the blood and the hepatocytes respectively, and $f_{uc}$ is the fraction of unbound solute in the cells.

Data fitting:

The normalized outflow concentration versus time profiles for each ester or pregenerated DF was analysed using an identical method to that outlined in our previous paper (Mellick et al., 1996, supra) which utilized the two-compartment dispersion model (Yano et al., 1990, *J. Pharm. Pharmacol.* 42 632–636; Evans et al., 1993, *J. Pharm. Sci.* 82 421–428; Hussein et al., 1994, *Pharm. Res.* 11 1337–1345).

According to this model, the normalized outflow concentration versus time profile, C(t) from the liver can be depicted by the following equation:

$$C(t) = I(t) * f(t)_{catheters} * f(t)_{liver} \quad (10)$$

where the symbol * denotes the convolution integral, I (t) is the input function for solute into the liver and $f(t)_{catheters}$ and $f(t)_{liver}$ are the transfer functions which describe the spread of transit times through the catheters and the liver respectively.

In the Laplace domain equation (10) is simplified with the convolution integral becoming multiplication and I(t) equalling 1 for a bolus input:

$$C(s)_{total} = f(s)_{catheters} * f(s)_{liver} \quad (11)$$

The transfer function $f(s)_{liver}$ for a non-eliminated extracellular reference solute such as EB in the liver can be described using the one-compartment dispersion model (mixed boundary conditions) such that (Roberts & Rowland, 1986, *J. Pharm. Pharmacol.* 38 177–181):

$$f(s)_{liver} = \exp\left[\frac{1 - \sqrt{1 + \frac{4D_N V_E s}{Q}}}{2D_N}\right] \quad (12)$$

where $V_E$ (or $V_B$) is the extracellular volume exhibited by the reference solute.

According to the two-compartment dispersion model (Yano et al., 1990, supra; Evans et al., 1993, supra) the Laplace expression describing the outflow profile of an exchanging solute in the liver is given by the following equation:

$$f(s)_{liver} = \exp\left[\frac{1 - \sqrt{1 + \frac{4D_N V_E \left[k_1 + s - \frac{k_1 k_2}{s + k_2 + k_{el}}\right]}{Q}}}{2D_N}\right] \quad (13)$$

where $k_1$ and $k_2$ represent the first order influx and efflux rate constants across the hepatocyte membrane and $k_{el}$ represents the hepatocyte's first order elimination rate constant (all with units of time$^{-1}$). These rate constants are further defined as:

$$k_1 = \frac{P f_{ub}}{V_B} \quad (14)$$

$$k_2 = \frac{P f_{uc}}{V_c} \quad (15)$$

$$k_{el} = \frac{CL_{int} f_{uc}}{V_c} \quad (16)$$

In this study, the various O-acyl esters' outflow profiles in the time domain were fitted to the appropriate transfer functions by numerical inversion of the Laplace equations using the Minim 3.0.8 non-linear parameter estimation program developed by Robert Purves (Purves 1995, *J. Pharm. Sci.* 84 71–74). A Gauss Newton minimization algorithm was utilized without weighting for all data points. The dispersion number and volume for the catheters was determined from fitting of a catheter outflow profile to equation (12). These values were subsequently used for convolution of the catheter function for all other profiles. For the various solutes, the [$^3$H]-water reference profile was first fitted to the one-compartment dispersion equation to determine the $D_N$ and MTT values (equation 12). Given the value of "Y" (the ratio of $V_C$ to $V_E$) obtained from the moments analysis equals to 0.59, we can then estimate $V_E$ for the particular injection using following equations:

$$MTT_W = \frac{V_C + V_E}{Q} \quad (17)$$

$$MTT_E = \frac{V_E}{Q} \quad (18)$$

$$\gamma = \frac{V_C}{V_E} \quad (19)$$

$$MTT_E = \frac{MTT_W}{r+1} \quad (20)$$

$$V_E = Q MTT_E \quad (21)$$

where $MTT_W$ and $MTT_E$ are the mean transit time of the whole liver and blood respectively. Then the solute profile was fitted using the two-compartment dispersion equation (equation 13) regulating the previously determined $D_N$ and $V_E$ values and estimating k , $k_1$ and k . . . . Consequently, equations (8) & (9) can be expressed as following:

$$MTT = \frac{MTT_E}{\sqrt{1 + 4R_N D_N}}\left(1 + \frac{k_1 k_2}{k_2^2 + 2k_2 k_e + k_e^2}\right) \quad (22)$$

$$CV^2 = \frac{2D_N}{a} + \frac{2a V_C k_2^2 f_{ub} f_{uc} Q(k_2 + k_e)}{[f_{uc} V_B (k_2 + k_e)^2 + f_{ub} k_2^2 V_C]^2} \quad (23)$$

Given the value of "a" derived from the experimentally obtained F using equation (5), and values of $D_N$ and $V_B$ which can be derived from the $CV^2$ and MTT of the non-extracted reference, respectively; we can use equations (22) and (23) to predict the values of MTT and $CV^2$ for a particular solute.

Results

Figure 11:
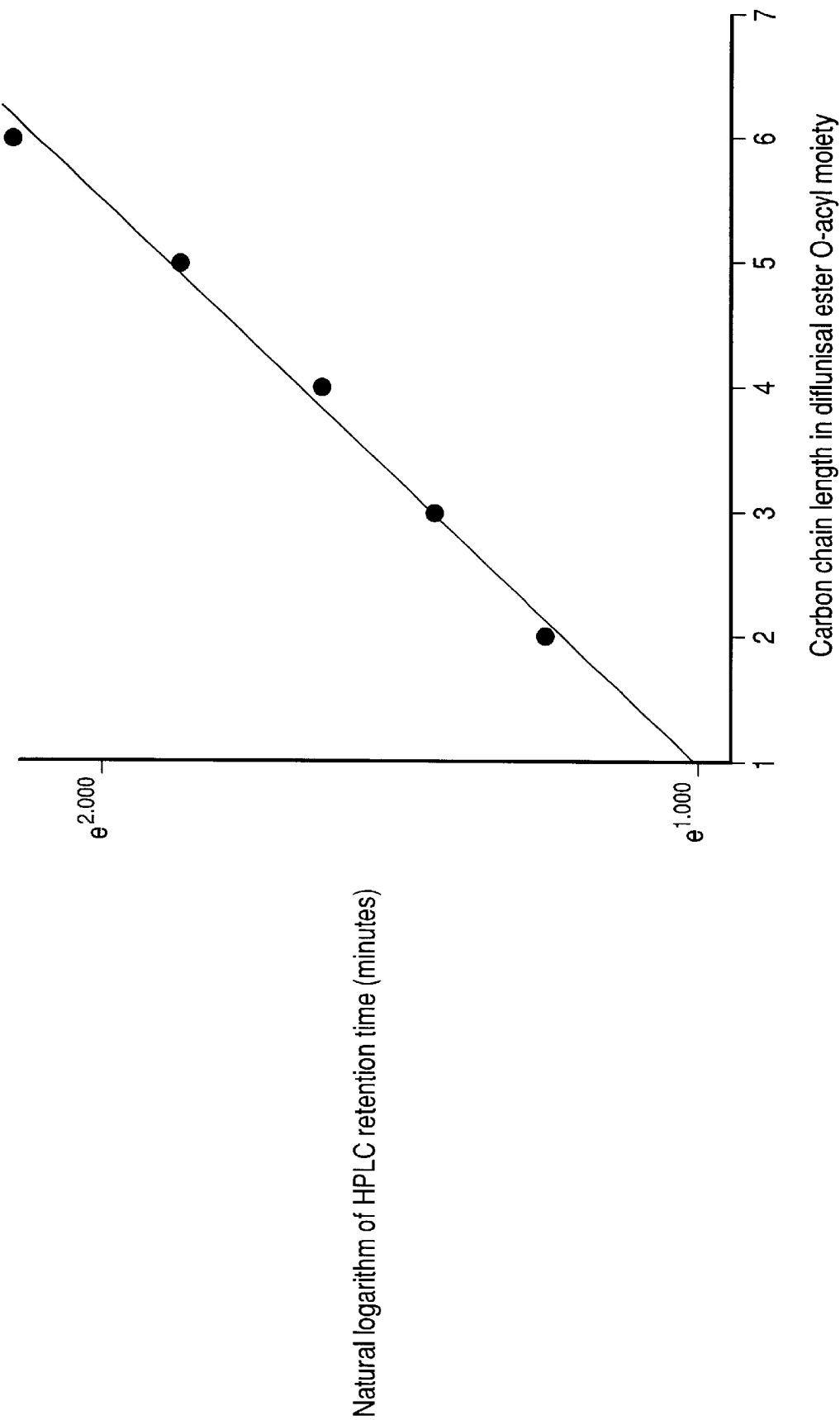
FIG. 11 shows the relationship between HPLC retention time and carbon chain length in the diflunisal O-acyl moiety.
Figure 12A:
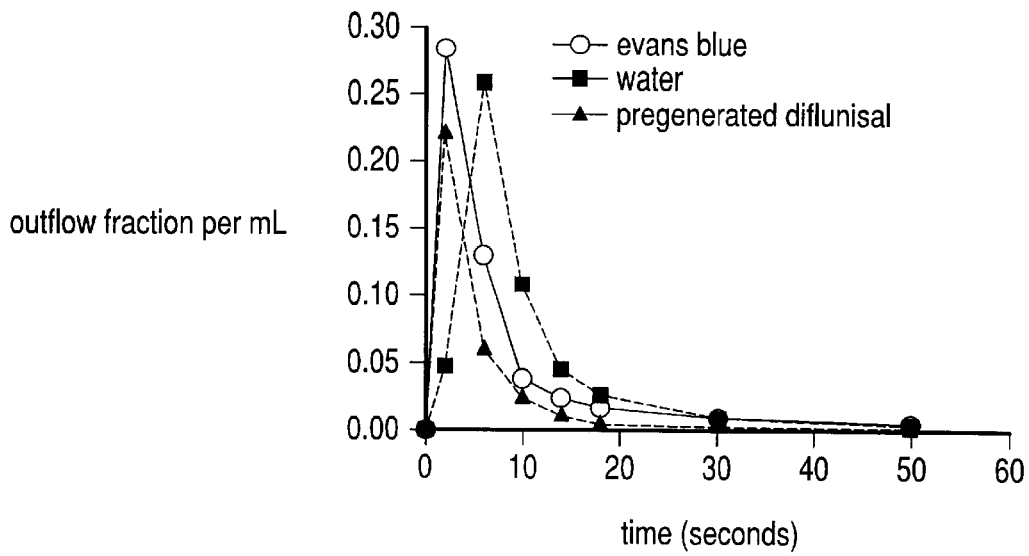
FIGS. 12a–12e illustrate normalized outflow concentration versus time profiles for the pregenerated DF and its O-acyl esters injected into the liver together with EB and $^3$H - water as reference markers.
Figure 12B:
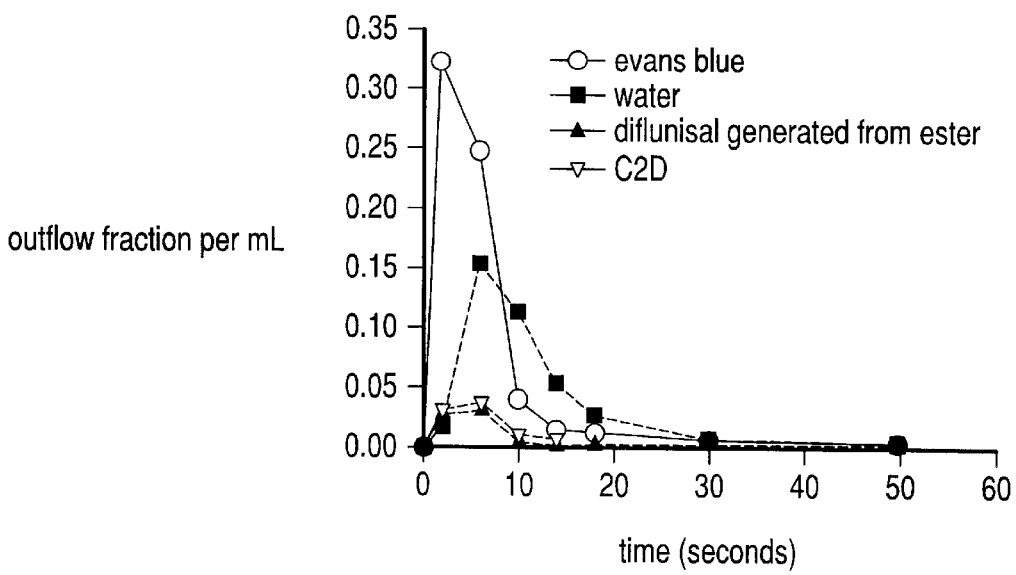
Figure 12C:
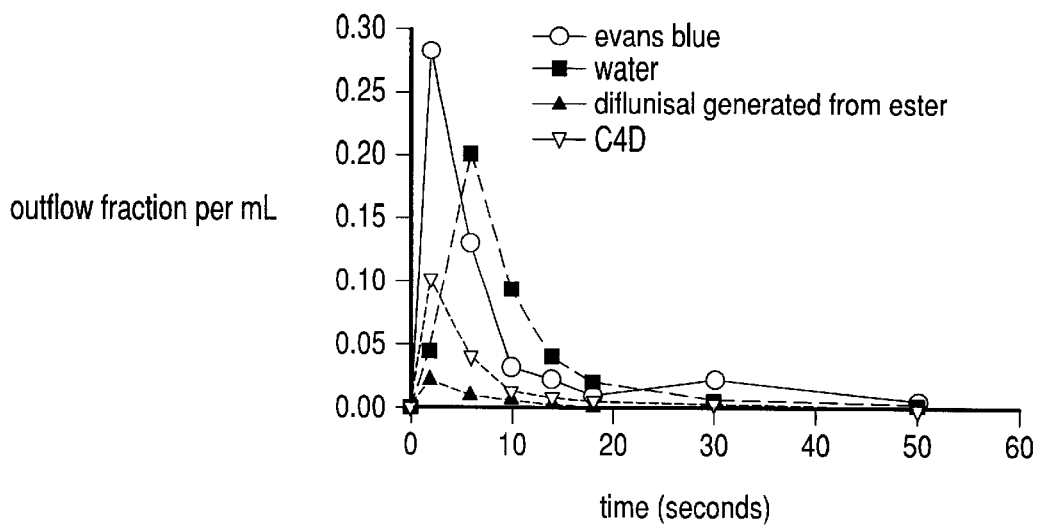
Figure 12D:
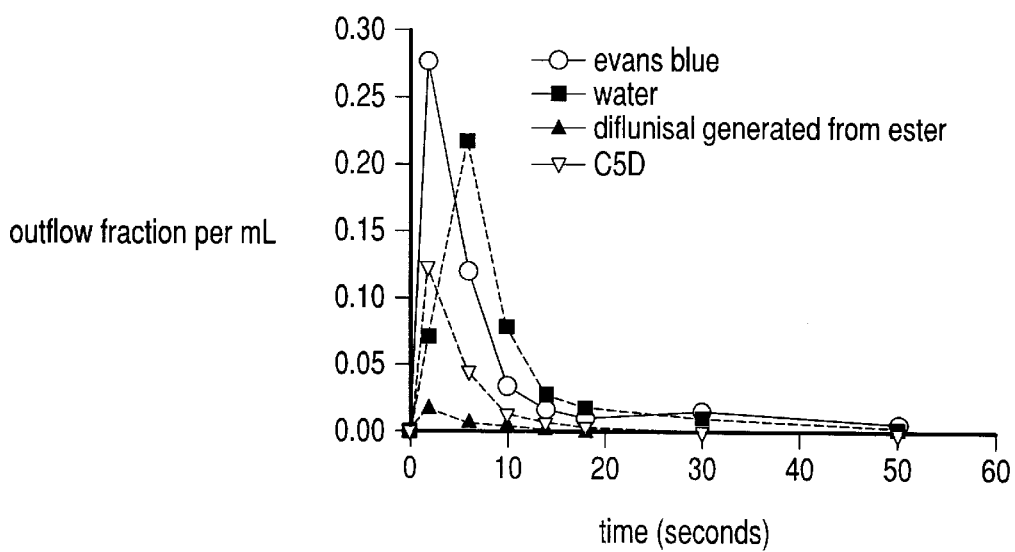
Figure 12E:
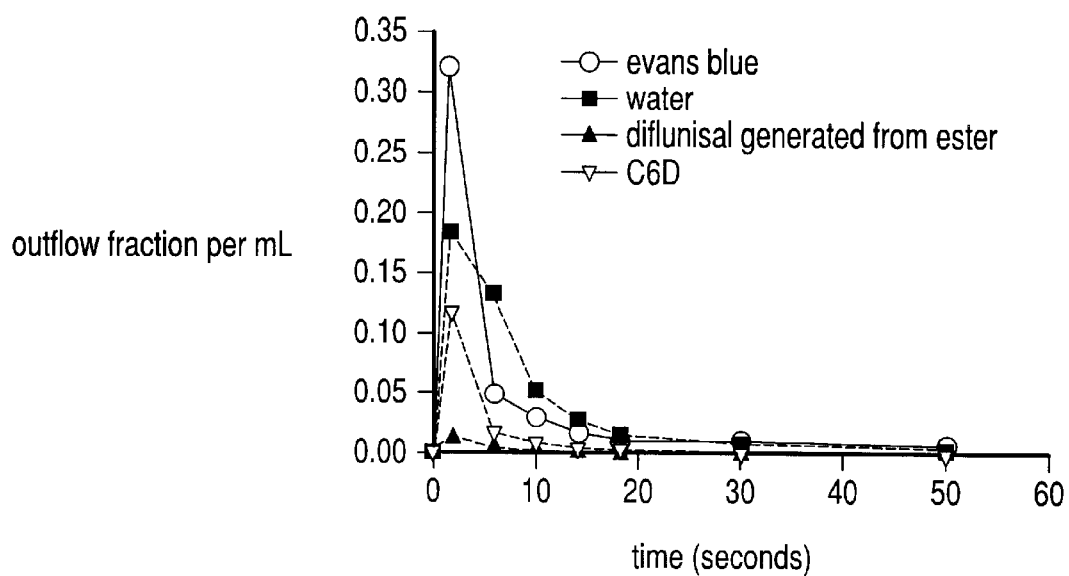
Figure 13A:
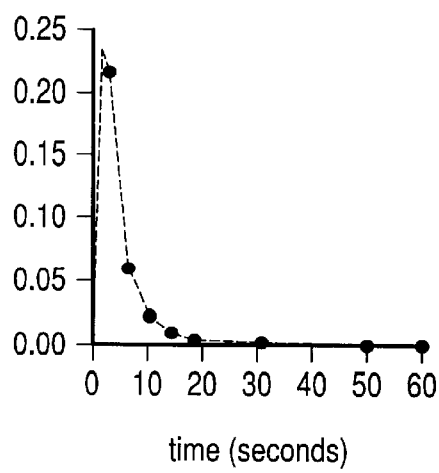
FIGS. 13a–13e show a dispersion model fitting of the normalized outflow concentration versus time profiles for the pregenerated DF and its O-acyl esters.
Figure 13B:
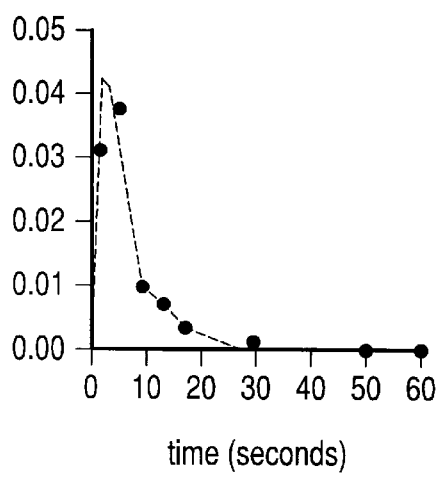
Figure 13C:
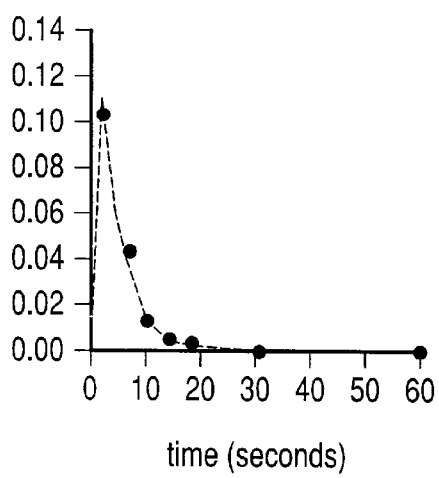
Figure 13D:
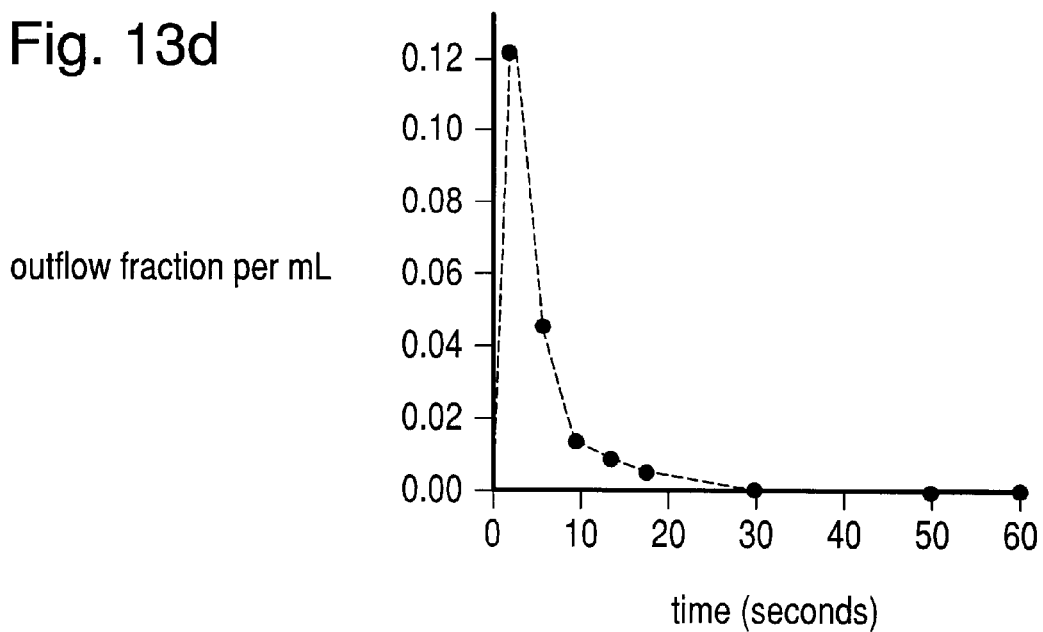
Figure 13E:
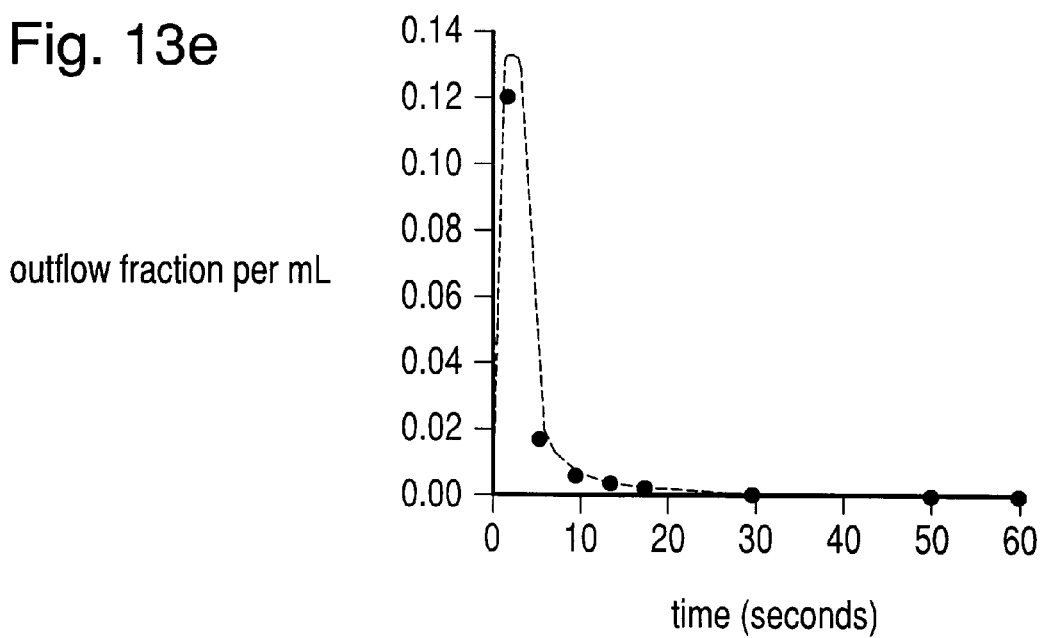

FIG. 11 shows the relationship between HPLC retention time and carbon chain length in the O-acyl moiety. A linear relationship was found between the logarithm of the HPLC retention time and the carbon atoms in the ester side chain reflecting the increase in lipophilicity as methylene groups on the side chain are added. For all compounds in this work, HPLC standard curves were linear within the range of concentrations studied (1 to 100 $\mu$g/mL) with linear regression analysis yielding $r^2$ values>0.999 for all solutes. The within day coefficients of variation for all the compounds were within the range of 2.1 to 6.4% (n=3).

FIGS. 12a–12e show the normalized outflow concentration versus time profiles for the pregenerated DF and its O-acyl esters injected into the liver together with EB and

[$^3$H]-water as reference markers. The DF generated from the ester within the liver and presented in the outflowing perfusate was assayed by HPLC. The outflow curves for the reference solutes, [$^3$H]-water and EB, remained relatively constant for the various injections. Statistical moments analysis yielded an F of 0.87±0.02, MTT of 14.42±0.79 seconds and $CV^2$=0.71±0.08 (n=12) for [$^3$H]-water and an F of 0.95±0.04, MTT of 9.04±0.65 seconds and $CV^2$= 1.15±0.11 (n=12) for EB.

FIGS. 13a–13e present the two-compartment dispersion model fittings for the pregenerated diflunisal and its O-acyl esters. The fitting of the [$^3$H]-water data yielded an average $D_N$ of 0.29±0.03 and an average $MTT_W$ of 11.70±1.39 seconds and $MTT_E$ of 7.36±0.87 (TABLE 10). These values are less than the corresponding values derived from the moments analysis. TABLE 11 shows the best fit coefficients for pregenerated DF and its O-acyl esters which were derived from the two-compartment dispersion model. The influx rate coefficient ($k_1$), efflux rate coefficient ($k_2$) and elimination rate coefficient ($k_{el}$) for the esters did not significantly change with carbon number except for C2D which exhibited significantly higher $k_1$ and $k_2$ values (p<0.05). This is consistent with the results for efficiency number ($R_N$) which showed a similar trend (TABLE 13).

TABLE 12 lists the statistical moments analysis results for pregenerated DF and its O-acyl esters. With the exception of C2D which showed a significantly lower availability to the others (P<0.05 ANOVA repeated measures), no significant difference between ester availabilities was observed. When pregenerated DF was injected into the liver as parent compound an availability of 0.62±0.04 was determined.

Figure 14:
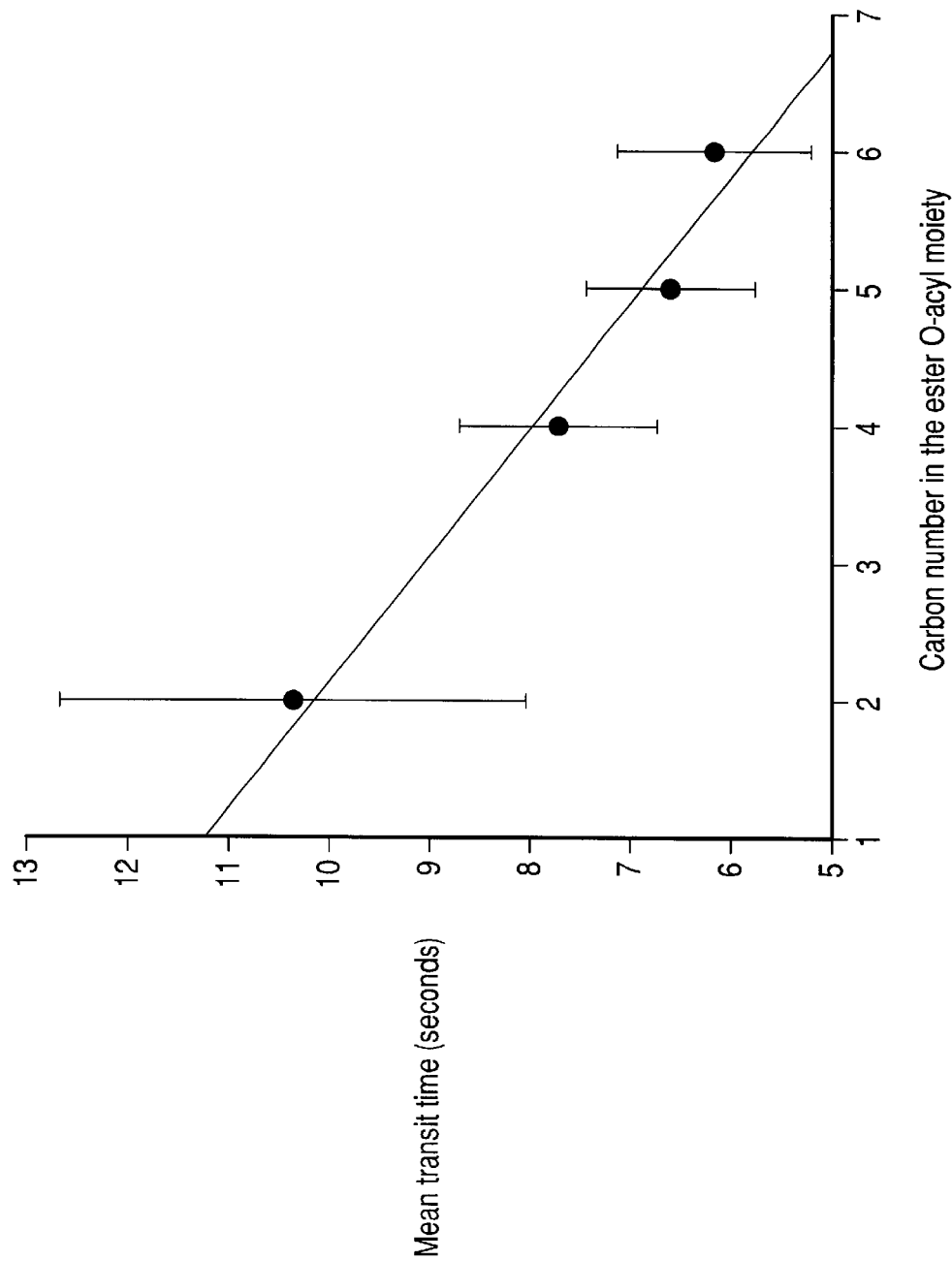
FIG. 14 depicts the relationship between hepatic mean transit time (MTT) and carbon number in the O-acyl moiety for the diflunisal esters.
Figure 15A:
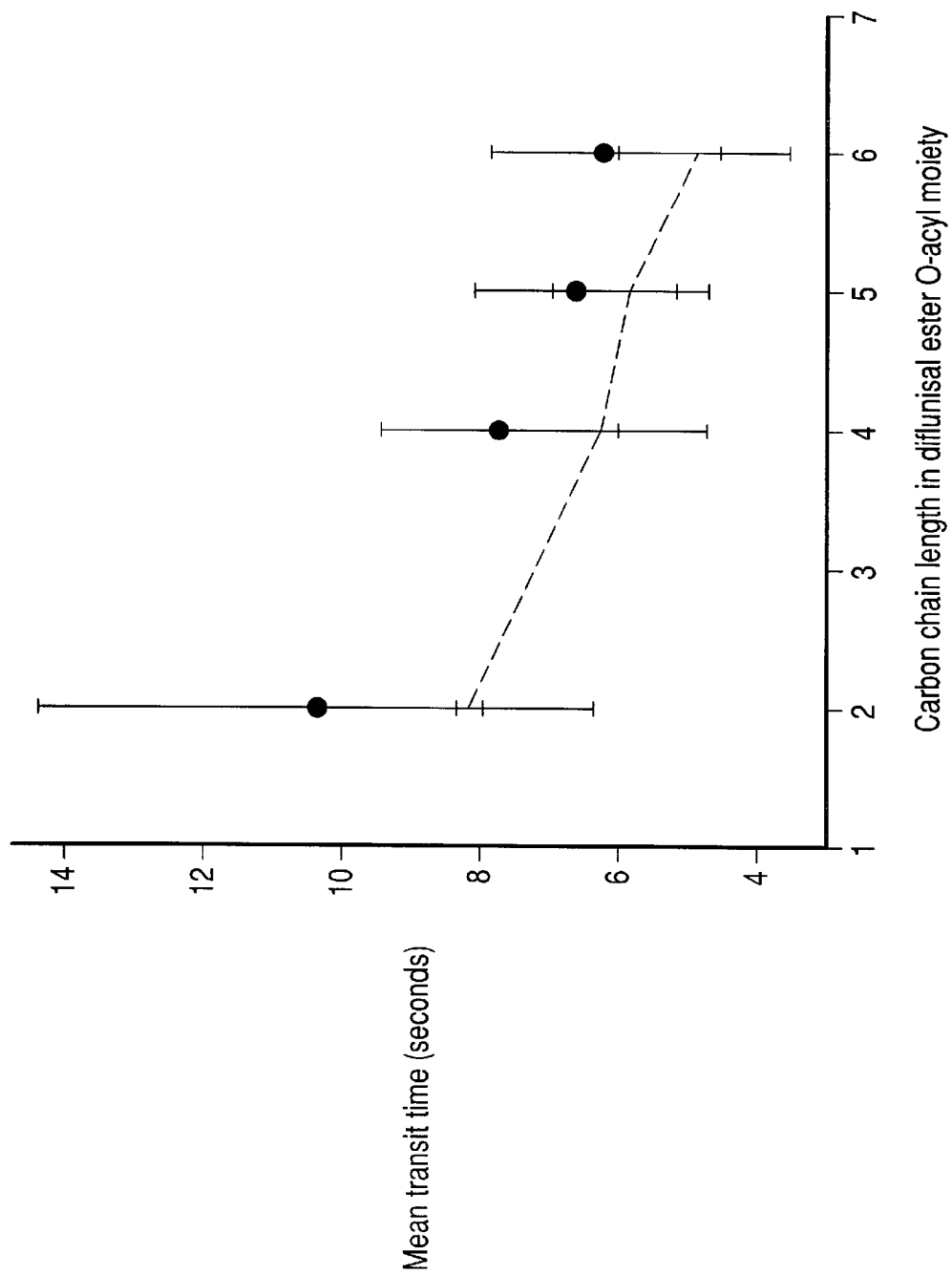
FIGS. 15a and 15b show a comparison of predicted and experimentally observed MTT (a) and $CV^2$ values (b) for the diflunisal esters.
Figure 15B:
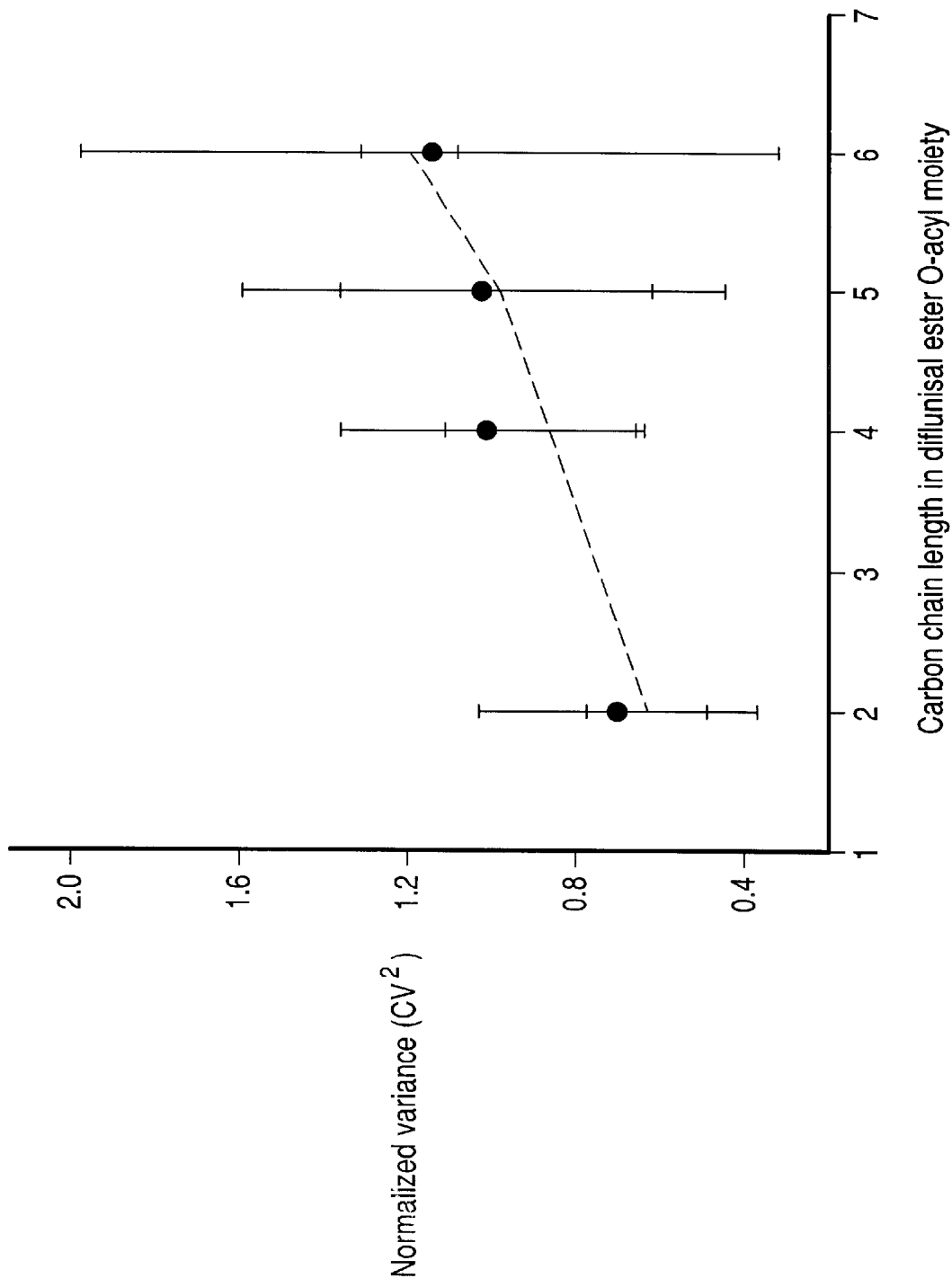

The diflunisal esters show an inverse relationship between MTT and carbon chain length (FIG. 14). FIGS. 15a and 15b present the comparison of predicted and experimentally observed MTT and $CV^2$ values for the diflunisal esters. Equations (22) and (23) were used to predict the MTT and $CV^2$ of the esters. The predicted values are similar to the experimental values observed and show a trend to shorter MTT and larger $CV^2$ values as the carbon number in the O-acyl group of the ester is increased.

Discussion

Chou et al., 1993 used a RBC-free, protein-free perfusate in a single-pass, in-situ perfused rat liver preparation to examine the relationship between lipophilicity and the disposition and distribution of a homologous series of barbiturates. These experiments revealed that for all but the n-pentyl 5-ethyl barbituric acid (the most lipophilic of the series) the extraction of the barbiturates by the liver was negligible (Chou et al., 1993, *Drug Metab. Disp.* 21 933–938). Mellick et al. (1996, supra) used a similar method to investigate the hepatic distribution and metabolite kinetics for a homologous series of O-acyl esters of salicylic acid. These experiments showed that the F of the salicylic acid esters decreased with increasing carbon chain length in the O-acyl moiety. However, the MTT and $CV^2$ for the esters did not significantly change with increasing carbon chain length (Mellick et al., 1996, supra). In this investigation, we compare the hepatic disposition of a homologous series of diflunisal esters using a similar method.

Figure 16:
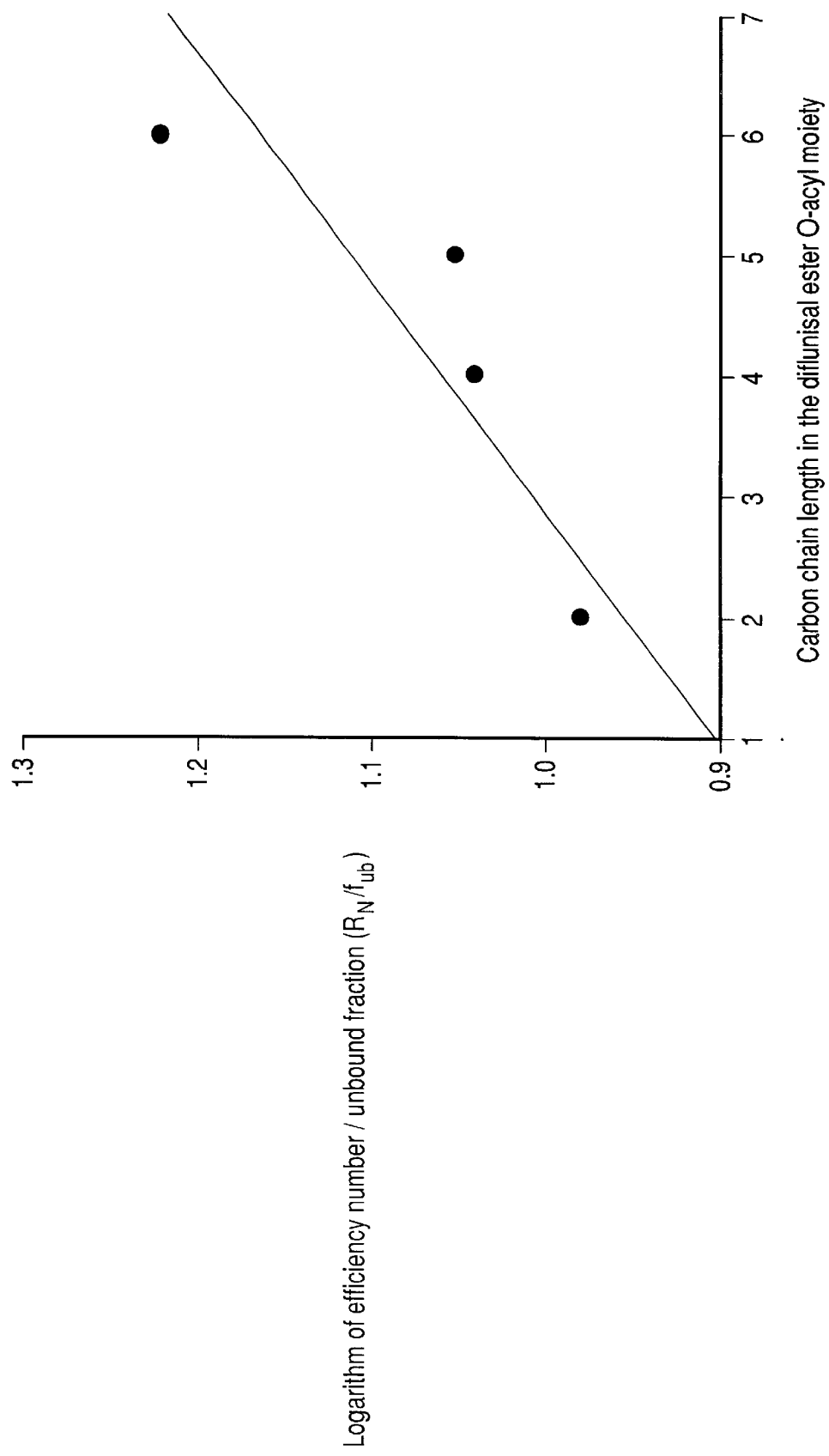
FIG. 16 illustrates the relationship between $R_N/f_{ub}$ and carbon chain length in the diflunisal ester O-acyl moiety.

The relationship between hepatic disposition and carbon number in the diflunisal esters is more complex, compared with the studies of barbiturate and salicylic acid derivatives. Both these previous experiments used a protein-free perfusate in a single-pass perfused rat liver preparation. In our experiments, the need to include 2% BSA in the perfusate to ensure adequate solubility of these diflunisal esters introduced a confounding factor. The F for the diflunisal esters does not significantly change with the carbon chain length except for C2D which has a significantly lower F. This is in contrast to the results of our previous work with the O-acyl salicylates (Mellick et al., 1996, supra) which showed that the F of the salicylic acid derivatives decreased linearly with increasing carbon chain length. Since 2% BSA was involved in our experiments, we should consider the influence of protein binding on F. For homologous series, it has been previously found that protein binding is directly related to the lipophilicity of the solute (Toon & Rowland, 1979, *J. Pharm. Pharmacol.* 31 (Suppl.) 43P). For the O-acyl esters of diflunisal, we have shown $f_{ub}$ to decrease with increasing carbon chain length (see Example 2). According to equation (7), $R_N$ depends on the unbound fraction as well as "$PCL_{int}/(P+CL_{int})$". Dividing $R_N$ by $f_{ub}$ for each diflunisal ester, we can examine how "$PCL_{int}/(P+CL_{int})$" changes as carbon chain length is increased. TABLE 13 lists the $R_N$, "a", and $R_N/f_{ub}$ results of these compounds. FIG. 16 shows that the removal of unbound diflunisal ester ($R_N/f_{ub}$) increased in a log-linear fashion with increasing carbon chain length ($r^2$= 0.75). This trend agrees with our previous salicylic acid ester results (Mellick et al., 1996). However, the study of Chou et al (1993, supra) showed that for all but the n-pentyl 5-ethyl barbituric acid (the most lipophilic of this series) the extraction of the barbiturates by the liver was negligible.

In the present study, C2D had a lower F compared to the other esters. This reflects the lower protein binding capacity of this ester compared to the longer chain analogues. The influx and efflux coefficients for C2D also reflect this as they are higher than those obtained for the longer chain esters.

The MTT for the diflunisal esters decreased with increasing lipophilicity (carbon chain length). This relationship can be explained by an increase in protein binding (decrease in $f_{ub}$) with increasing lipophilicity. We have previously demonstrated that $f_{ub}$ decreased with increasing carbon chain length in the O-acyl moiety for this group of diflunisal esters (Example 2). Equation (8) shows that for the case when $P<<CL_{int}$ a decrease in $f_{ub}$ leads to a reduction in MTT. Since removal of the free ester also increases with lipophilicity, MTT is expected to decrease with increasing carbon number. This is in contrast to the results of Chou et al. (1993, supra) who showed that the MTT for the barbiturates increased with lipophilicity and the results of Mellick et al. (1996, supra) who showed that the MTT for the salicylic acid derivatives did not change with lipophilicity. MTT is known to depend on the volume of distribution of the solute and its elimination (equation 8). If there is no extraction (ie. $Cl_{int}$=0, and a=1), equation (8) reduces to:

$$MTT = \left[\frac{f_{uc}V_B + f_{ub}V_c}{Q}\right] \quad (24)$$

and the MTT is solely dependent upon the volumes. This is the case for the barbiturates which showed increased volume of distribution in the liver with increasing lipophilicity. However, for the salicylic acid derivatives, an increase in volume of distribution with increasing lipophilicity was counteracted by an increase in efficiency of removal which has the effect of reducing MTT. As a result the MTT for all salicylic acid derivatives remained relatively constant. For the case of diflunisal esters, equation (8) shows that a decrease in $f_{ub}$ together with an increase in P and $CL_{int}$ leads to a reduction in MTT. This is consistent with the predicted MTT values which yield decreased values as extraction of the solute increase (FIG. 15a).

The observed normalized variance ($CV^2$) for the diflunisal esters showed no significant difference across the range of analogues with the exception of C2D. However, there was a trend to higher $CV^2$ values with increasing lipophilicity (FIG. 15b). This is consistent with the predicted $CV^2$ values which yield increased values as the lipophilicity of the solutes increase. A lower $CV^2$ value of C2D in the series of diflunisal esters can be explained by equation (23). From this equation, a lower $CV^2$ value can be expected as acetyidiflunisal has the highest values of $f_{ub}$ and $f_{uc}$ (lowest lipophilicity) in this series of diflunisal esters.

In this work the dispersion number of the liver ($D_N$) was calculated from the [$^3$H]-water data using two methods. The dispersion number largely reflects the heterogeneity of the hepatic microvasculature and similar values have been obtained for reference solutes such as erythrocytes, chromium labelled RBC, labelled albumin, and a number of solutes of varying physicochemical characteristics (Roberts et al., 1988, *J Pharmacokinet. Biopharm.* 16 41–83; Roberts et al., 1990, *J Pharmacokinet. Biopharm.* 18 209–234). According to the moments analysis, $CV^2=0.71\pm0.08$ which yields a $D_N$ of $0.36\pm0.04$ $$\left(D_N = \frac{CV^2}{2}\right).$$

Fitting of the [$^3$H]-water data to the one-compartment dispersion model (equation 12) yields an average $D_N$ value of 0.29—0.03 (TABLE 10). It has been previously shown that statistical moments methods yield $D_N$ values somewhat higher than those determined from dispersion model fitting method (Mellick et al., 1996, supra). This may reflect the fact that the inverse-Gaussian distribution described by the dispersion model equation (the Laplace inversion of equation 12) underestimates solute concentrations at long times. Weiss et al. (1996, unpublished) has suggested that two double inverse-Gaussian distribution better fit the outflow profile for reference solutes (Weiss et al., 1996, supra).

Conclusions

Although no significant difference was observed between the hepatic availabilities of the various esters, the removal of unbound ester increased with increasing carbon number ($R_N/f_{ub}$ increased from 9.57 for acetyl and 16.50 for hexanoyl) when the dispersion model was used to calculate the removal efficiency number ($R_N$) from the availability and protein binding data. Hence, the more lipophilic diflunisal esters might be expected to have a less deleterious effect on prostacyclin production in the post-hepatic vessels than aspirin due to their extensive hepatic elimination.

EXAMPLE 4

Hydroxyl Radical Scavenging Potency of O-Acyl Derivatives of Diflunisal and Salicylic Acid in the Ischaemic/Reperfusion Rat Liver Oxygen-derived free radicals have been implicated in cell injury observed during ischaemia (Kontos and Hess, 1983, *Adv Exp Med Biol* 15 269–278) and reperfusion (Ambrosio et al., 1987, *Circulation* 76 906–915). The mechanism of reactive oxygen species generation through superoxide formation as proposed by McCord (McCord J M, 1985, *N Eng J Med* 312 159–163) involves the enhanced degradation of adenosine to hypoxanthine during ischaemia as well as the conversion of the cytosolic xanthine dehydrogenase to xanthine oxidase (Roy R S, 1983, Superoxide and Ischaemia: Conversion of Xanthine Dehydrogenase to Xanthine Oxidase, In *Oxy Radicals and Their Scavenger Systems. II. Cellular and Medical Aspects*, Eds. R. A. Greenwald and G. Cohen, pp.145–153, Elsevier Science/North-Holland, New York) which uses oxygen instead of NAD$^+$as an electron acceptor. Since the oxygen concentration in tissue is extremely low during the ischaemic period, the metabolism of hypoxanthine by xanthine oxidase is inhibited due to the lack of the second substrate of this reaction. Upon reflow, oxygen is available and formation of reactive oxygen species such as superoxide anion can occur, causing reperfusion injury.

Reactive oxygen species can also be generated from the metabolism of polyunsaturated fatty acids. Previous studies have shown that the hydroxyl radical may be produced during activation of the lipoxygenase pathway (Singh et al., 1981, *Am J Haematol* 11 233–240; Cheung et al., 1984 *Aus J Exp Biol Med Sci* 62 403–419) and under ischaemic conditions, a significant amount of free fatty acids, particularly arachidonic acid, is accumulated at the same time (Slater T F, 1984, *Biochem J* 222 1–15; Girotti A, 1985, *Free Radical Biology and Medicine* 1 87–95). These fatty acids cannot be reacylated into the membrane phospholipids because the reacylation system becomes defective during ischaemia primarily as a result of the inactivation of lysophosphatidylcholine acyltransferation (Das et al., 1986, *Am J Physiol* 251 471–479). They may be metabolised through the lipoxygenase and cyclooxygenase pathways to generate free radicals.

The only defence against the free radicals is the naturally occurring antioxidative enzymes such as superoxide dismutase (SOD) and catalase. The activities of these enzymes are known to be depressed during ischaemia, limiting the ability of the cell to inactivate the free radical moiety (Guarneri et al., 1979, *Biochem Biophys Res Comm* 89 678–684; Guameri et al., 1980, *J Mol Cell Cardiol* 12 797–808).

To meet the free radical challenge during reperfusion of ischaemic liver, scavengers of free radicals can be introduced prior to reperfusion. A number of studies have been undertaken in recent years where beneficial effects of free radical scavengers (e.g. SOD, Vitamin E, catalase, etc.) were observed during reperfusion of ischaemic liver and heart (Oshino et al., 1973, *Arch Biochem Biophys* 154 117–131; Tyler D D, 1975, *Biochem J* 147 493–504; Fridovich I, 1983, *Annu Rev Pharmacol Toxicol* 23 239–257; Kappus H, 1985, Lipid peroxidation: mechanisms, analysis, enzymology and biological relevance, In *Oxidative Stress* (Ed. Sies H), pp.273–310, Academic Press, New York). However, the substrate for free radical formation, polyunsaturated fatty acids such as arachidonic acid, once formed in the ischaemic liver, cannot be combatted with any such interventions. Besides, these free fatty acids tend to disrupt the membranes by their detergent effect. Thus, as soon as reperfusion occurs with a burst of free radicals, the hepatocytes become defenceless.

Some previous studies have shown that reperfusion after ischaemia induced rapid endothelial cell injury and Kupffer cell activation (Sankary et al., 1995, *Hepatology* 22 1236–1242; Rao et al., 1995, *J Aller Clin Immunol* 95 1276–1281; Brass and Roberts, 1995, *Gastroenterology* 108 1317–1320). A number of mediators such as tumour necrosis factor-alpha (TNF-α), prostaglandins, oxygen radicals and nitric oxide are released by these cells in the hepatic sinusoid after reperfusion (Harbrecht et al., 1995, *J Surg Res* 58 625–629). Such mediators cause necrosis and marked microcirculatory disturbances in the liver characterised by elevated lactate dehydrogenase (LDH) activity, reduced blood flow and increased leucocyte and platelet adhesion (Lemasters et al., 1995, *J Gastroenterol Hepatol* 10 Suppl 1 584–587; Zhong et al., 1995, *J Pharmacol Exp Ther* 275 1512–1517).

In the present investigation we attempted to develop compounds which could scavenge oxygen radicals, especially the hydroxyl radical (OH•) and reduce the damage caused by prostaglandins in ischaemic/reperfusion injury. It is hypothesised that phenolic O-acyl esters can react rapidly with OH by aromatic hydroxylation and inhibit cyclooxygenase by acylation, thus adequately fulfilling the role of minimising free radical and fatty acid-mediated ischaemic/reperfusion injury.

A homologous series of phenolic NSAID, salicylic acid (SA) and diflunisal (DF) derivatives, aspirin analogues and diflunisal esters were examined. Their in-vitro effects on OH. and superoxide scavenging were assessed using luminol-dependent chemiluminescence (CL) measurements. The relationship between lipophilicity and hepatic extraction of these compounds in the liver were determined using the in-situ perfused rat liver preparation. LDH release and bile production (bile flow rate) were used as indices of liver function during ischaemic/reperfusion experiments. The quantitative structure-activity relationship (QSAR) studies for this homologous series were established using Hansch analysis.

Materials and Methods

Synthesis

O-acyl derivatives of SA and DF (TABLE 15) were prepared by esterification of SA (Sigma Chemical Co., St. Louis, Mo.), and DF (Sigma) with either the appropriate acyl-anhydride or acid chloride as described previously.

Effects of aspirin analogues and diflunisal esters on luminol-dependent CL

Measurements:

CL was measured with a luminometer (Model 1250; LKB Wallac, Finland) and recorded in millivolts (Cheung et al., 1984, supra).

In vitro hydroxyl radical production:

Fenton's reagent ($FeSO_4$ and $H_2O_2$) was used as a standard reaction mixture for the generation of OH. (Lai and Piette, 1979, Tetrahedron Lett. 775–778):

$$Fe^{++} + H_2O_2 \rightarrow Fe^{+++} + OH \cdot + OH \quad (1)$$

The initial reaction mixture consisted of 20 μL of 3.8 mM $FeSO_4 \cdot 7H_2O$, 20 μL of 5 mg/mL luminol (Sigma), and 2 mL of 1 mM phosphate buffer in a 3 mL polystyrene cuvette. Twenty microlitres of 320 mM $H_2O_2$ was added to initiate the Fenton's reaction.

Inhibition of CL by aspirin analogues and diflunisal esters:

A known concentration of the ethanolic (≤1%) aspirin analogue or diflunisal ester's stock solution was added to the 1 mM phosphate buffer to prepare solutions with a final concentration of 50 μM, 250 μM or 500 μM. Twenty microlitres of these test samples was added onto the cuvette which contained the initial reaction mixture. $H_2O_2$ was added to induce CL reaction. The luminol-dependent CL response was recorded in mV by a potentiometric recorder.

Effects of aspirin analogues and diflunisal esters on xanthine oxidase plus xanthine -induced CL:

To clarify the role of aspirin analogues and diflunisal esters in free radicals scavenging, the Fenton's reagent was replaced by an artificial superoxide generating system in the CL inhibition studies. This cell-free system consisted of 100 μg/mL of xanthine oxidase (Sigma) plus 0.5 μM xanthine (Sigma) (Rosen and Klebanoff, 1976, J Clin Invest 58 50–60; Cheson et al., 1976, J Clin Invest 58 789–796).

For statistical analysis of CL measurements, light production was quantitated as the area under the CL-time curve and compared to control studies whose CL response was set at 100%. CL measurements were always done in triplicate and Student's t-test used to assess the statistical significance of the difference between measurements.

In-situ rat liver perfusions

The hepatic availability (F) for the O-acyl esters of SA and DF was determined using a once through in-situ perfused rat liver preparation (Mellick and Roberts, 1996, J Pharm Pharmacol 48:738–743). Liver was perfused with protein-free Krebs-Henseleit buffer at 30 mL/min for aspirin analogues and with Krebs-Henseleit buffer containing 2% BSA for diflunisal esters studies. Since the solubilities of the diflunisal esters in protein-free media were very low, 2% BSA were used to help to solubilize these compounds. Briefly, 50 μL of a saturated solution of the particular O-acyl SA or DF in Krebs-Henseleit buffer was injected as a bolus into the portal vein cannula. Perfusate outflow samples have collected via a fraction collector over 3 min. 100 μL of these samples was assayed by HPLC to determine the residual concentration of presented ester and the quantity of phenolic metabolite (SA or DF) collected from the perfused liver. The HPLC assay was a modification of the method used by Owen et al. (1987, J Chrom B Biomed Appl 416 293–302) and Rumble et al. (1981, J Chrom 225 252–260).

The hepatic availability (F) was calculated from the ratio of the area under the first moment curve, i.e., outflow concentration time-time profile to the area under the curve for the salicylate phenolic esters, with the assistance of the Moments Calculator 2.2 program for Macintosh computer developed by Robert Purves (1994, J Pharm Sci 83:202–205).

Effects of aspirin analogues and diflunisal esters on ischaemic/reperfusion injury in rat livers Female Sprague-Dawley rats (220–250 g) were anaesthetised by interperitoneal injection of pentobarbital sodium (60 mg/kg, Boehringer Ingelhein). Following laparotomy animals were heparinized (Heparin sodium, David Bull Laboratories Australia, 200 units) via the inferior vena cava. The bile duct was cannulated with a polyethylene tubing (PE-10, I.D. 0.28 mm; Clay Adams, New Jersey) and bile was collected into pre-weighed microcentrifuge tubes at 70 min intervals (in the middle of experiment and the end of experiment). The portal vein was then cannulated using a 16 G intravenous catheter and the liver was perfused via this cannula with 2% BSA Krebs-Henseleit bicarbonate buffer (pH 7.4) and oxygenated using a membrane oxygenator comprising of silastic tubing and ventilated with carbogen (95% $O_2$/5% $CO_2$). The perfusion system used was recirculating and employed a peristaltic pump (Cole-Parmer, Illinois). After perfusion was effected, the animal was sacrificed by thoracotomy and the thoracic inferior vena cava was cannulated with another polyethylene tubing (PE-240, I.D. 1.67 mm; Clay Adams, New Jersey) and the liver was perfused at a constant flow rate (0.15 mL/min/g body weight).

Following a 10 min pre-ischaemia perfusion, the perfusion flow was stopped for 30 min at 37° C. with the liver being kept moist. At the end of this ischaemic phase, a known concentration of the aspirin analogue or diflunisal ester's solution (in 2% BSA Krebs-Henseleit buffer) was added into the perfusate prior to the perfusion being resumed for another 100 min. Outflow fractions were collected up to 140 min. A biochemistry autoanalyzer (Hitachi, model 747; Tokyo, Japan) was employed to determine the level of enzyme (LDH) release.

The degree of ischaemic/reperfusion injury was measured by calculating the area under the LDH release (mL/min/g liver) versus time curve (AUC). The AUC of control (no drug treatment) was assigned to be 100% injury. The efficacy of each compound is expressed in terms of $ED_{50}$ which represents the molar dose for 50% reduction of LDH release compared to the control. The comparison of bile production between the first stage of experiment (the first 70 min) and the second stage of experiment (the last 70 min) is also used as index of liver function during an experiment.

Estimation of lipophilicity (1-octanol/water partition coefficient)

The 1-octanol/water partition coefficient of these compounds were estimated using following equation (Leo et al., 1975, *J Med. Chem* 18:865–868; Yalkowsky S H, 1981, Techniques of solubilization of-drugs, Marcel Dekker, New York, Chapter 1):

$$\log P = \sum_{all\ groups} f_{groups} \quad (2)$$

where f is the substituent constants for some common atoms and groups (Nys and Rekker "f" values) (Yalkowsky S H, 1981, supra), P is the estimated 1-octanol/water partition coefficient. We can calculate the log P value for any compound in this homologous series by adding the "f" values for all of its constituents' groups.

Results

TABLE 15 shows the % inhibition of CL caused by different compounds under varying concentrations. The results indicated that all the compounds studied (including SA and DF) reacted with OH. generated from Fenton's reaction. The percentage inhibition increased with the dose of the compounds used. No observable reaction of these compounds with superoxide generated from xanthine oxidase plus xanthine reaction was detected. The selectivity of the Fenton's reaction implies that these compounds are specific OH. scavengers. The inhibition strength of this homologous series at medium and high concentrations (2.5 $\mu$M & 5 $\mu$M) was found only to be slightly different. However, diflunisal esters have stronger inhibition ability at low concentration (0.5 $\mu$M) than aspirin analogues. SA and DF have similar strength in OH. scavenging as their parent esters at three different concentrations.

TABLE 16 lists the moments analysis results for each injection in this study. It shows that the hepatic extraction of aspirin analogues increased with the increase in carbon number in the O-acyl group. However, the relationship between hepatic extraction and carbon number in the diflunisal esters is more complex in contrast to the aspirin analogues. There is no significant difference in hepatic extraction for the longer chain diflunisal esters, i.e., O-butanoyl DF (C4D) to O-hexanoyl DF (C6D).

TABLE 17 lists the observed biological activities and estimated lipophilicity of aspirin analogues and diflunisal esters in the ischaemic/reperfusion rat livers. The results show that the more lipophilic esters (longer carbon chain length in O-acyl group) exhibited higher biological activities. By contrast, SA and DF showed less biological activities than those of O-acetyl SA (C2SA) and O-acetyl DF (C2D) despite their higher lipophilicity. Diflunisal esters have stronger activities than aspirin analogues. This is consistent with the results of in-vitro CL inhibition studies. Although the lipophilicity (log P) of C5D is less than those of C6D and O-heptanoyl DF (C7D), it has the highest biological activity (log 1/C) and hence being the cut-off point in this homologous series.

Figure 17:
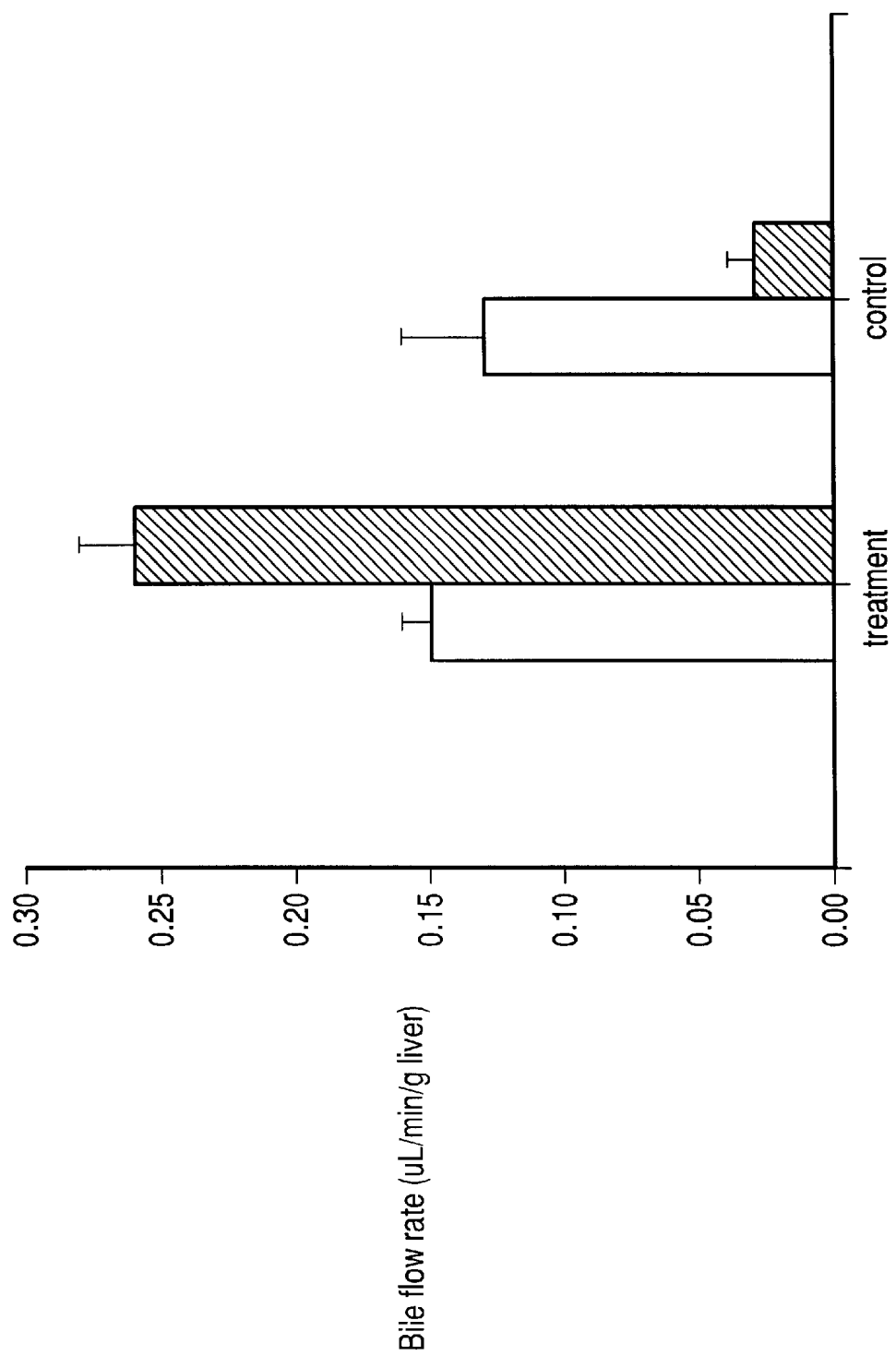
FIG. 17 shows the effects of aspirin analogues and diflunisal esters on bile production.

FIG. 17 illustrates the effects of aspirin analogues and diflunisal esters on bile production. The bile flow rate in the first stage of experiment was measured significantly lower (p<0.05) than that in the second stage of experiment for all treatment groups (0.15±0.01 $\mu$L/min/g liver and 0.26±0.02 $\mu$L/min/g liver, respectively). By contrast, we obtained opposite results in the control group which showed a significantly higher (p<0.02) bile production in the first stage of experiment than that in the second stage of experiment (0.13±0.03 $\mu$L/min/g liver and 0.03±0.01 $\mu$L/min/g liver, respectively). This indicates that the liver function is improved after treatment, whereas it is deteriorated in the non-treatment control group due to the ischaemic/reperfusion injury.

Discussion

Theoretically, most NSAIDs possess the ability to scavenge OH.. This is expected from their chemical structure, since aromatic compounds are known to react very rapidly with OH. by aromatic hydroxylation (Aruoma et al., 1987, *Biochem Pharmacol* 36 3739). The mechanism of reaction can be elucidated by the example of salicylate (Whitehouse M W, 1995, *Inflammopharmacology* 3 373–377). The salicylate anion can be oxygenated to form 2,3-dihydroxybenzoate and its 2,5 isomer, gentisate, by polymorphonuclear leucocytes (PMNs) by at least 2 mechanisms: (a) non-enzymatically involving hydrogen peroxide and superoxide ions interacting, with Fe as catalyst, to produce OH., or (b) involving the enzyme myeloperoxidase (MPO) acting either intracellularly or when extruded from PMN granules, which can directly transform salicylate to these dihydroxybenzoates. These are reactive diphenols, act as antioxidants and are transformed to reactive benzoquinones (Whitehouse M W, 1995, supra). This double quenching sequence can be represented as:

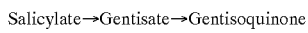

Salicylate→Gentisate→Gentisoquinone

Hence, in terms of OH. scavenging, any anti-inflammatory drug with aromatic structure present at a site of inflammation would remove OH. if the drug concentration is high enough (at least 1 mM) (Kaplan H B, 1984, *Biochem Pharmacol* 33 371; Brooks et al., 1986, The Clinical Pharmacology of Anti-inflammatory Drugs, Taylor and Francis, London; Vane and Botting, 1987, *FASEB Journal* 1 89). However, they have limited usage in the treatment of hepatic ischaemic/reperfusion injury due to their low hepatic extractions. Since SA and DF have similar strength in OH. scavenging as their parent esters, they can maintain this pharmacological activity after the parent esters are metabolised within the hepatocytes. In the sense of prodrug, the esterification of these two NSAIDs may increase their potency of scavenging OH. in the liver. Since the double aromatic ring structure of diflunisal may provide more locations for OH. addition, we can expect a stronger CL inhibition ability of diflunisal esters than aspirin analogues. This superiority was found at low concentration (0.5 $\mu$M) but no significant difference was found at medium and high concentrations (2.5 $\mu$M & 5 $\mu$M).

No significant difference in hepatic extraction for the longer chain diflunisal esters (C4D to C6D) was found. A confounding factor arises from the need to include of 2% BSA in the perfusate to ensure adequate solubility of these diflunisal esters. To circumvent this complication and compare with aspirin analogues, it is necessary to analyse these hepatic extraction results more extensively. Since 2% BSA was involved in our experiments, we should consider the influence of protein binding on hepatic extraction. For homologous series, it has been shown previously that protein binding is directly related to the lipophilicity of the solute (Toon and Rowland, 1979, *J Pharm Pharmacol* 31 Suppl 43P). For the O-acyl esters of diflunisal, we have previously demonstrated that the unbound fraction of solute ($f_{ub}$) to decrease with increasing carbon chain length. The efficiency of hepatic elimination is defined by a dependent variable, the efficiency number $R_N$, in a range of hepatic elimination models (Roberts et al., 1990, *J Pharmacokin Biopharm* 18 209–234):

$$R_N = \frac{f_{ub} P C L_{int}}{Q(P + CL_{int})} \quad (3)$$

where P is the hepatocyte's permeability to the solute, $CL_{int}$ is the intrinsic clearance of the liver (defined as $$CL_{int} = \sum_{i=1}^{n} \frac{V_{MJ}}{K_{MJ}}$$

(Gillette J R, 1971, *Ann N Acad Sci* 179 43–61), Q is the perfusate flow rate. The efficiency number ($R_N$) may appear to be constant when the decrease of unbound fraction ($f_{ub}$) associated with the increasing lipophilicity of solutes is counterbalanced by the increase of P or $CL_{int}$ for the more lipophilic solutes. As a result, the hepatic extraction for longer chain diflunisal esters appear to remain relatively constant. With this assumption considered, it can be concluded that the hepatic extraction of diflunisal esters increased with increasing lipophilicity then reached a plateau after C5D.

Figure 18:
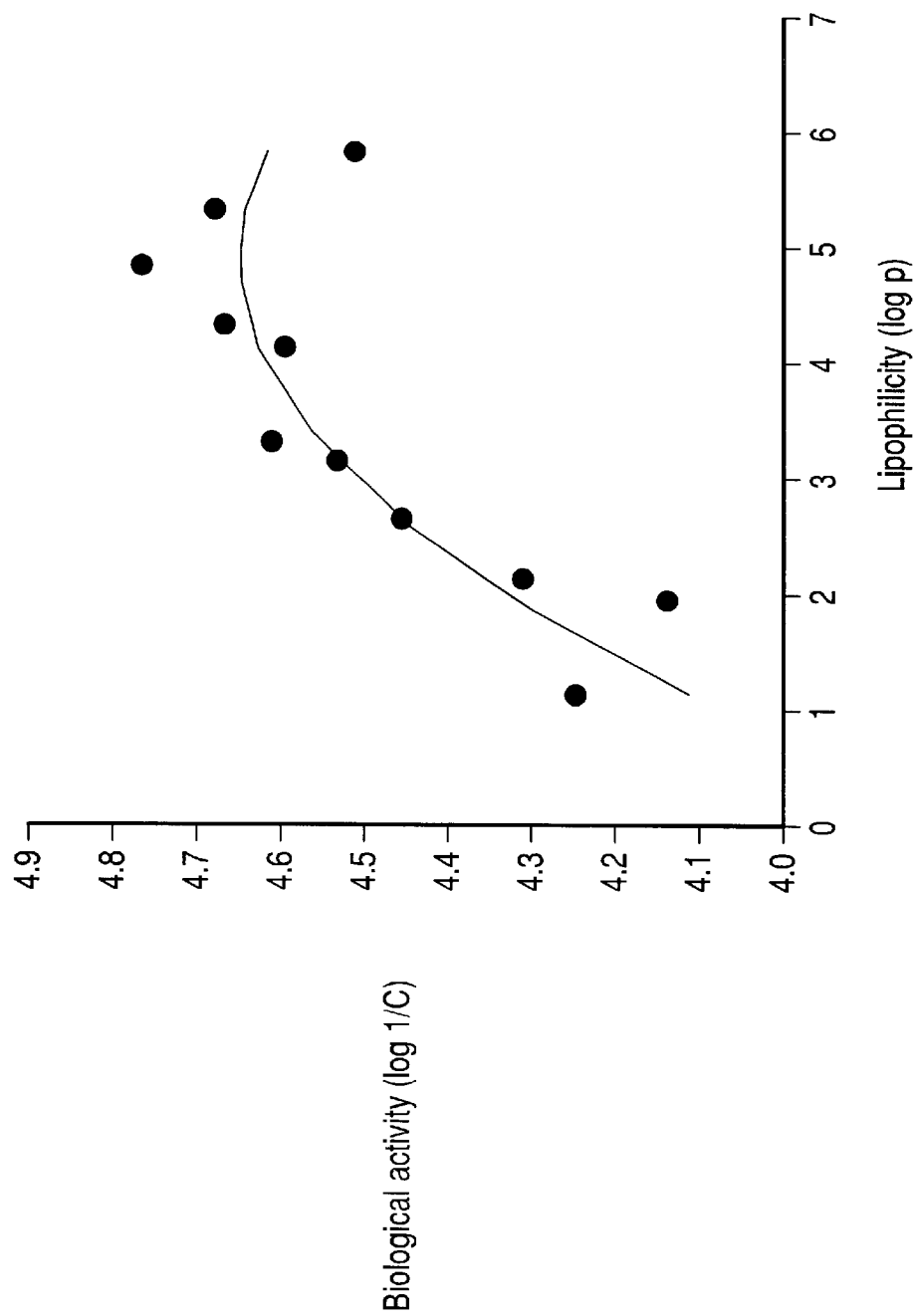
FIG. 18 shows the relationship between biological activity (log 1/C) and lipophilicity (log P) for aspirin analogues and diflunisal esters by using nonlinear regression analysis.

Hansch postulated a "random walk" concept to explain the cut-off point noted in certain homologous series (Smith J H, 1988, Introduction to the principles of drug design (2nd ed.). Wright, Kent. Chapter 8). He suggested that (/) a random walk involves passage across hydrophilic barriers and lipophilic barriers; thereby (ii) some where between the two extremes, there will be an optimum balance between hydrophilic and lipophilic properties so that a plot of hydrophilic-lipophilic nature against the likelihood of the molecule completing the random walk would be expected as a parabolic form. He formulated a parabolic model for the mathematical description of the cut-off point noted in certain homologous series (Smith J H, 1988, supra). The general equation is:

$$\log 1/C = k_1 + k_2 \log P + k_3 (\log P)^2 \quad (4)$$

where $k_1$, $k_2$ and $k_3$ represent the relevant coefficients, C is the $ED_{50}$ molar dose and P is the 1-octanol/water partition coefficient. In this work, we found that the more lipophilic esters (longer carbon chain length in O-acyl group) exhibited significantly higher biological activities but a fall off in biological activity as the lipophilicity of this homologous series were higher than C5D. Hence, nonlinear regression analysis was performed using equations (2) and (4) to compute the best correlation between biological activity (log 1/C) and lipophilicity (log P) for this homologous series in determining their optimum QSAR. FIG. 18 shows a parabolic relationship existed between log 1/C and log P for this homologous series. The best correlation obtained is:

$$\log 1/C = 3.7369 + 0.3558(\pm 0.1112) \log P - 0.0345(\pm 0.0147)(\log P)^2 \quad (5)$$

($n=11, r=0.988, s=0.0884$, optimum $\log P=4.6542$)

which indicates that the partitioning effects of the substituents have significant role in determining the biological activities of this homologous series. Such an approach can be used to modify the structure of a drug which is designed to target and alleviate the ischaemic/reperfusion injury in the liver.

SA and DF showed less biological activities than their parent esters, C2SA and C2D despite their higher lipophilicity than those of C2SA and C2D. It is suggested that the O-acyl group in the parent ester not only enhances hepatic extraction but inhibits cyclooxygenase by acylation. Thus, the acylation capability of these O-acyl NSAID derivatives cooperated with their aromatic hydroxylation disposition to minimise the free radical and fatty acid-mediated ischaemic/reperfusion injury.

TABLE 1

Variant combination of mobile phase, internal standard, and flow rate used for detecting salicylic acid and diflunisal derivatives in HPLC assay.

| Composition of mobile phase | Internal standard | Flow rate | Compounds detectable |
|---|---|---|---|
| 19:80:1 (acetonitrile: 0.03% (v/v) phosphoric acid: triethylamine) at pH 2.0 | 0.004% w/v p-toluic acid in acetonitrile | 1.5 mL/min | C2SA and C3SA |
| 49:50:1 (acetonitrile: 0.03% (v/v) phosphoric acid: triethylamine) at pH 2.0 | 0.004% w/v diflunisal in acetonitrile | 1 mL/min | C4SA to C8SA |
| 64:35:1 (acetonitrile: 0.03% (v/v) phosphoric acid: triethylamine) at pH 2.0 | 0.004% w/v salicylic acid in acetonitrile | 1 mL/min | C2D to C7D (except C3D) |
| 34:65:1 (acetonitrile: 0.03% (v/v) phosphoric acid: triethylamine) at pH 2.0 | 0.004% w/v salicylic acid in acetonitrile | 1.5 mL/min | C3D |

TABLE 2

Maximum solubility of aspirin analogues and diflunisal esters at 25 1° C. in water at pH 1.5

| Compound | MW | Solubility g/mL[a] | mM |
|---|---|---|---|
| C2SA | 180 | 3300[b] | 18.5 |
| C3SA | 194 | 1200 ± 120 | 6.3 |
| C4SA | 208 | 570 ± 80 | 2.7 |
| C5SA | 222 | 74 ± 31 | 0.33 |
| C6SA | 236 | 19 ± 4 | 0.08 |
| C8SA | 264 | 2 ± 0.2 | 0.008 |
| C2D | 292 | 9 ± 0.1 | 0.03 |
| C3D | 306 | 3 ± 0.2 | 0.01 |
| C4D | 320 | U[c] | U |
| C5D | 334 | U | U |
| C6D | 348 | U | U |

TABLE 3

Maximum solubility of diflunisal esters in 2% BSA Krebs-Henseleit buffer (pH 7.4) at 25 1° C.

| Compound | MW | Solubility mg/mL[a] | mM |
|---|---|---|---|
| C2D | 292 | 2.2 ± 0.07 | 7.57 |
| C3D | 306 | 3.15 ± 0.02 | 10.29 |
| C4D | 320 | 3.96 ± 0.08 | 12.38 |
| C5D | 334 | 6.98 ± 0.15 | 20.90 |
| C6D | 348 | 15.58 ± 0.3 | 44.77 |

TABLE 4

The hydrolysis rate constant (k) and half life ($t_{1/2}$) of aspirin analogues and diflunisal esters in Krebs-Henseleit buffer containing 0 or 2% BSA.

| Compound | Hydrolysis rate constant (hour[1]) Krebs-Henseleit buffer 0% BSA | Krebs-Henseleit buffer 2% BSA | Half life (hour)[b] Krebs-Henseleit buffer 0% BSA | Krebs-Henseleit |
|---|---|---|---|---|
| C2SA | 0.0171 ± 0.0035[a] | 0.0114 ± 0.0025 | 40.53 | 60.80 |
| C3SA | 0.0147 ± 0.0025 | 0.0102 ± 0.0031 | 47.14 | 67.94 |
| C4SA | 0.0049 ± 0.0037 | 0.0031 ± 0.0015 | 141.43 | 223.55 |
| C5SA | 0.0061 ± 0.0027 | 0.0028 ± 0.0013 | 113.61 | 247.50 |
| C6SA | 0.0059 ± 0.0023 | 0.0021 ± 0.0017 | 117.46 | 330.00 |
| C7SA | 0.0052 ± 0.0032 | 0.0013 ± 0.0005 | 133.27 | 533.08 |
| C8SA | 0.0051 ± 0.0031 | 0.0010 ± 0.0004 | 135.88 | 693.00 |
| C2D | 0.0378 ± 0.0105 | 0.0238 ± 0.0095 | 18.33 | 29.12 |
| C4D | U[c] | 0.0138 ± 0.0058 | U | 50.22 |
| C5D | U | 0.0113 ± 0.0037 | U | 61.33 |
| C6D | U | 0.0056 ± 0.0042 | U | 123.75 |

TABLE 5

Protetn binding constant (k) of aspirin analogues and diflunisal esters.

| Compound | Binding constant (liter/mole) | Compound | Binding constant (liter/mole) |
|---|---|---|---|
| C2SA | 192 | C2D | 2077 |
| C5SA | 1525 | C4D | 2365 |
| C6SA | 2071 | C5D | 2707 |
| C8SA | 13978 | C6D | 2995 |

TABLE 6

The O-acyl derivatives of salicylic acid (SA) and diflunisal (DF) used in relation to Example 2.

| Salicylic acid derivatives (SA) | Derivative abbreviation | Diflunisal derivatives (DF) | Derivative abbreviation |
|---|---|---|---|
| O-acetyl SA | C2S | O-acetyl DF | C2D |
| O-propionyl SA | C3S | O-propionyl DF | C3D |
| O-butanoyl SA | C4S | O-butanoyl DF | C4D |
| O-pentanoyl SA | C5S | O-pentanoyl DF | C5D |
| O-hexanoyl SA | C6S | O-hexanoyl DF | C6D |
| O-Octanoyl SA | C8S | O-heptanoyl DF | C7D |

TABLE 7

Effect of various aspirin and diflunisal derivatives on the platelet aggregation induced by arachidonic acid.

Platelet Aggregation (% of control)[b]
Preincubation Time (Minutes)

| Drug | 3 | 5 | 8 | 10 | 12 | 15 | 20 | 25 | 45 |
|---|---|---|---|---|---|---|---|---|---|
| Control[c] | 97.3 ± 0.1 | 97.3 ± 0.1 | 97.3 ± 0.1 | 97.3 ± 0.1 | 97.3 ± 0.1 | 97.3 ± 0.1 | 97.3 ± 0.1 | 97.3 ± 0.1 | 97.3 ± 0.1 |
| C2S | 0 | 0 | 0 | 0 | 0 | 0 | 0 | 0 | 0 |
| C3S | 0 | 0 | 0 | 0 | 0 | 0 | 0 | 0 | 0 |
| C4S | 29.5 ± 1.5[d] | 0 | 0 | 0 | 0 | 0 | 0 | 0 | 0 |
| C5S | 63.5 ± 1.5 | 41.3 ± 1.1 | 0 | 0 | 0 | 0 | 0 | 0 | 0 |
| C6S | 90.1 ± 2.2 | 70.5 ± 3.1 | 39.9 ± 1.1 | 0 | 0 | 0 | 0 | 0 | 0 |
| C8S | 95.4 ± 2.1 | 92.4 ± 0.1 | 87.3 ± 3.3 | 67.5 ± 2.7 | 27.3 ± 0.2 | 0 | 0 | 0 | 0 |
| C2D | 92.3 ± 0.5 | 67.3 ± 2.9 | 27.9 ± 1.1 | 0 | 0 | 0 | 0 | 0 | 0 |
| C3D | 96.5 ± 3.1 | 89.3 ± 0.4 | 67.3 ± 0.1 | 49.7 ± 1.1 | 19.3 ± 0.5 | 0 | 0 | 0 | 0 |
| C4D | 96.1 ± 0.3 | 90.3 ± 2.1 | 73.9 ± 0.7 | 57.3 ± 0.1 | 31.8 ± 0.4 | 0 | 0 | 0 | 0 |
| C5D | 97.1 ± 0.1 | 95.3 ± 0.7 | 90.6 ± 0.9 | 87.3 ± 3.1 | 75.9 ± 0.1 | 57.5 ± 1.7 | 0 | 0 | 0 |
| C6D | 97.2 ± 0.2 | 94.7 ± 0.3 | 93.3 ± 0.2 | 90.1 ± 2.1 | 89.3 ± 0.1 | 71.7 ± 1.9 | 45.6 ± 0.5 | 0 | 0 |
| C7D | 97.5 ± 0.9 | 96.3 ± 1.1 | 91.4 ± 0.1 | 91.1 ± 2.1 | 90.8 ± 0.8 | 89.7 ± 2.1 | 77.3 ± 3.1 | 57.3 ± 0.1 | 0 |

TABLE 8

Hepatic availability (F) results for salicylic acid derivatives and diflunisal esters bolus studies.

| Drug | Hepatic availability (F)[a] | Drug | Hepatic availability (F)[b] |
|---|---|---|---|
| C23 | 0.85 | C2D | 0.21 |
| C4S | 0.40 | C4D | 0.34 |
| C5S | 0.26 | C5D | 0.38 |
| C6S | 0.02 | C6D | 0.38 |

TABLE 9

Isolated rat liver perfusion conditions and viability parameters in this study.

| Experiment | Rat Weight[a] (gm) | Liver Weight (gm) | O$_2$ Consumption[b] (mol/min/gm liver) | Bile Production (g/min/gm liver) |
|---|---|---|---|---|
| 1 | 258 | 7.07 | 1.00 | 1.55 |
| 2 | 254 | 8.39 | 1.15 | 0.72 |
| 3 | 220 | 5.81 | 1.60 | 1.98 |

TABLE 10

Fitting results for $^3$H-water data to one-compartment dispersion model (n = 12).

| Curve | $D_N$ | $MTT_W$ (sec) | $MTT_E$ (sec) |
|---|---|---|---|
| 1 | 0.24 | 10.16 | 6.39 |
| 2 | 0.26 | 10.07 | 6.33 |
| 3 | 0.24 | 8.78 | 5.52 |
| 4 | 0.29 | 9.66 | 6.08 |
| 5 | 0.33 | 16.05 | 10.09 |
| 6 | 0.23 | 15.15 | 9.52 |
| 7 | 0.27 | 18.56 | 11.67 |
| 8 | 0.36 | 21.31 | 13.40 |
| 9 | 0.23 | 8.12 | 5.11 |
| 10 | 0.23 | 7.94 | 4.99 |
| 11 | 0.22 | 6.73 | 4.23 |
| 12 | 0.58 | 7.87 | 4.95 |
| Mean S.E. | 0.29 0.03 | 11.70 1.39 | 7.36 0.87 |

TABLE 11

Parameters derived from two-compartment dispersion model fitting for pregenerated diflunisal and its O-acyl esters (n = 3).

| Compound | Influx rate coefficient ($k_1$) (sec$^{-1}$) | Efflux rate coefficient ($k_2$) (sec$^{-1}$) | Elimination rate coefficient ($k_{el}$) (sec$^{-1}$) |
|---|---|---|---|
| DF[a] | 0.18 ± 0.03[b] | 0.02 ± 0.01 | 0.06 ± 0.01 |
| C2D | 1.20 ± 0.11 | 0.25 ± 0.03 | 0.18 ± 0.02 |
| C4D | 0.41 ± 0.12 | 0.08 ± 0.04 | 0.16 ± 0.07 |
| C5D | 0.51 ± 0.16 | 0.14 ± 0.07 | 0.18 ± 0.06 |
| C6D | 0.63 ± 0.24 | 0.06 ± 0.03 | 0.15 ± 0.03 |

TABLE 12

Moments calculator results for pregenerated diflunisal and diflunisal esters' bolus studies (n = 3).

| Compound | F | MTT (sec) | CV$^2$ |
|---|---|---|---|
| DF | 0.62 ± 0.04[a] | 6.80 ± 0.94 | 0.99 ± 0.27 |
| C2D | 0.21 ± 0.03 | 10.36 ± 2.31 | 0.70 ± 0.19 |
| C4D | 0.34 ± 0.01 | 7.73 ± 0.99 | 1.01 ± 0.18 |
| C5D | 0.38 ± 0.02 | 6.62 ± 0.84 | 1.02 ± 0.33 |
| C6D | 0.38 ± 0.04 | 6.19 ± 0.95 | 1.15 ± 0.48 |

TABLE 13

"a", $R_N$, $f_{ub}$, and $R_N/f_{ub}$ results for pregenerated diflunisal and diflunisal esters' bolus studies (n = 3).

| Compound | a[a] | $R_N$[a] | $f_{ub}$[b] | $R_N/f_{ub}$ |
|---|---|---|---|---|
| DF | 1.33 ± 0.01 | 0.76 ± 0.05 | 0.08 ± 0.01 | 9.51 ± 0.18 |
| C2D | 2.26 ± 0.02[c] | 2.58 ± 0.02 | 0.27 ± 0.02 | 9.57 ± 0.37 |
| C4D | 1.87 ± 0.01 | 1.56 ± 0.02 | 0.14 ± 0.01 | 11.17 ± 0.38 |
| C5D | 1.77 ± 0.02 | 1.32 ± 0.03 | 0.12 ± 0.01 | 11.04 ± 0.39 |
| C6D | 1.77 ± 0.03 | 1.32 ± 0.03 | 0.08 ± 0.00 | 16.50 ± 0.22 |

TABLE 14

The O-acyl derivatives of salicylic acid (SA) and diflunisal (DF) synthesised in work carried out in relation to Example 4.

| Derivative | Abbreviation | Derivative | Abbreviation |
|---|---|---|---|
| O-acetyl SA | C2SA | O-acetyl DF | C2D |
| O-butanoyl SA | C4SA | O-butanoyl DF | C4D |
| O-pentanoyl SA | C5SA | O-pentanoyl DF | C5D |
| O-hexanoyl SA | C6SA | O-hexanoyl DF | C6D |
| | | O-heptanoyl DF | C7D |

TABLE 15

CL inhibition (%) caused by different compound under variant concentrations.

| | CL inhibition (%)[a] | | | | | |
|---|---|---|---|---|---|---|
| | Concentration of compound | | | | | |
| | 0.5M | | 2.5M | | 5M | |
| Compound | F[b] | X[c] | F | X | F | X |
| SA | U[d] | U | 52.9 ± 2.1 | U | 99.0 ± 1.0 | 0.2 ± 0.0 |
| C2SA | U | U | 43.3 ± 5.0 | U | 97.6 ± 0.5 | 0.4 ± 0.1 |
| C4SA | U | U | 41.3 ± 7.5 | U | 84.2 ± 1.4 | 0.3 ± 0.1 |
| C5SA | 0.4 ± 0.1[e] | U | 45.9 ± 5.0 | U | 95.6 ± 0.4 | 0.3 ± 0.0 |
| C6SA | 0.2 ± 0.1 | U | 56.0 ± 3.7 | U | 96.0 ± 2.1 | 0.2 ± 0.0 |
| DF | 19.2 ± 6.9 | U | 50.6 ± 2.8 | U | 92.1 ± 0.6 | 0.4 ± 0.1 |
| C2D | 21.3 ± 5.0 | U | 49.8 ± 3.9 | U | 91.2 ± 0.6 | 0.5 ± 0.0 |
| C4D | 16.9 ± 4.9 | U | 65.1 ± 2.1 | U | 93.7 ± 0.5 | 0.6 ± 0.1 |
| C5D | 22.2 ± 7.1 | U | 58.2 ± 2.5 | U | 88.8 ± 0.9 | 0.8 ± 0.0 |
| C6D | 20.5 ± 4.6 | U | 54.8 ± 2.4 | U | 92.7 ± 3.1 | 0.7 ± 0.1 |
| C7D | 21.3 ± 3.7 | U | 57.3 ± 1.9 | U | 87.4 ± 3.4 | 0.9 ± 0.1 |

TABLE 16

Hepatic extraction of aspirin analogues and diflunisal esters.

| Compound | Hepatic extraction[a] | Compound | Hepatic extraction[b] |
|---|---|---|---|
| SA | 0.05[c] | DF | 0.38 |
| C2SA | 0.15 | C2D | 0.49 |
| C4SA | 0.60 | C4D | 0.66 |
| C5SA | 0.74 | C5D | 0.62 |
| C6SA | 0.98 | C6D | 0.62 |

TABLE 17

Observed biological activities and estimated lipophilicity of aspirin analogues and diflunisal esters in the ischaemic/reperfusion rat livers.

| Compound | log P[a] | $ED_{50}$ | log 1/C[b] |
|---|---|---|---|
| SA | 2.06[c] | 7.26 × 10$^{-5}$M | 4.14 |
| C2SA | 1.19 | 5.65 × 10$^{-5}$M | 4.25 |
| C4SA | 2.25 | 4.88 × 10$^{-5}$M | 4.31 |
| C5SA | 2.78 | 3.46 × 10$^{-5}$M | 4.46 |
| C6SA | 3.31 | 2.91 × 10$^{-5}$M | 4.54 |
| DF | 4.32 | 2.52 × 10$^{-5}$M | 4.60 |
| C2D | 3.49 | 2.44 × 10$^{-5}$M | 4.61 |
| C4D | 4.55 | 2.13 × 10$^{-5}$M | 4.67 |
| C5D | 5.08 | 1.70 × 10$^{-5}$M | 4.77 |
| C6D | 5.61 | 2.07 × 10$^{-5}$M | 4.68 |
| C7D | 6.14 | 3.04 × 10$^{-5}$M | 4.52 |

TABLE LEGENDS
TABLE 2
  a Data expressed as mean standard deviation (n=16).
  b Literature value from The Merck Index 1983.
  c Undetectable.
TABLE 3
  Data expressed as mean standard deviation (n=3).
TABLE 4
  a n=5, p 0.05.
  b First half life.
  c U=Undetectable
TABLE 7
  a Platelets were preincubated with aspirin analogues and diflunisal esters (600 M) at 37° C. for 3 to 45 minutes.
  b Platelet aggregation were induced by arachidonic acid (200 M).
  c Solvent (4% BSA in normal saline) used as control.
  d Significantly different compared with control (n=3, p 0.05)
TABLE 8
  a Protein-free Krebs-Henseleit buffer used as perfusate.
  b 2% BSA in Krebs-Henseleit buffer used as perfusate.
TABLE 9
  a Animals: Mature female Sprague-Dawley Rats.
  b Perfusion Rate: 30 mL/min. Pressure: 13 3 cm $H_2O$.
TABLE 10
  $MTT_E = MTT_W/(+1)$, =0.59 (from the moments analysis)
  where $MTT_W$ and $MTT_E$ are the mean transit time of the whole liver and blood, respectively.
TABLE 11
  a Diflunisal injected as parent.
  b Mean S.E.
TABLE 12
  a Mean S.E.
TABLE 13
  a Determined using equation 5 & 6.
  b Hung et al., 1996.
  c Mean S.E.
TABLE 15
  a The treatment group (compound+phosphate buffer+1% ethanol ) whose Chemiluminescence (CL) response was quantitated as the area under the CL-time curve and compared to the control group (phosphate buffer+1% ethanol) whose CL response was set at 100%.
  b CL was induced by Fenton's reagent.
  c CL was induced by xanthine oxidase plus xanthine reaction.
  d undetectable.
  e Significantly different compared with control (n=3, p 0.05).
TABLE 16
  a protein-free Krebs-Henseleit buffer used as perfusate.
  b 2% BSA in Krebs-Henseleit buffer used as perfusate.
  c hepatic extraction=1- hepatic availability (F).
TABLE 17
  a p is the 1-octanol/water partition coefficient.
  b C is the $ED_{50}$ molar dose.
  c Nys and Rekker f values for some common atoms and groups (Yalkowsky 1981).

FIGURE LEGENDS

FIGS. 1a & 1b.
  The relationship between HPLC retention time and carbon chain length of the ester O-acyl moiety for (a) aspirin analogues (y =0.3095+0.3519x, r²=0.999) (b) diflunisal esters (y=1.4124+0.2661x, r²=0.99).

FIG. 2.

The relationship between melting point and the carbon chain length of the ester O-acyl moiety. The figure shows that the melting points of diflunisal esters (□) followed the same trend as that observed by Yalkowsky et al. (1974, supra) for the melting points of the alkyl p-aminobenzoates. They fall as the side chain was increased from methyl to pentyl then rose as the length of the side chain was increased from the pentyl to the heptyl derivative. For the aspirin analogues (○), there are two exceptions to this trend. The melting point of C5SA is higher than for C4SA and the melting point of C7SA is lower than for C6SA. Diflunisal esters have much higher melting points than those of aspirin analogues.

FIG. 3.

The relationships between solubility (○), melting point (□) and carbon chain length for the aspirin analogues. Melting point data has previously been used to adequately predict drug solubilities for solutes belonging to the p-hydroxybenzoate homologous series (Forster et al., 1991, supra). The figure shows that the melting points and solubilities of aspirin analogues followed a similar trend.

FIG. 4.

The relationship between spontaneous hydrolysis rate constant and carbon chain length of the salicylate O-acyl moiety in Krebs buffer (○) or 2% BSA Krebs buffer (□). The greatly diminished hydrolysis rate constant for C4SA compared to its shorter chain counterparts suggests a steric hindrance exists when four or more carbon atoms are present in the side chain. In the present of albumin, the spontaneous hydrolysis rate of the aspirin analogues was decreased.

FIGS. 5a & 5b.

The unbound fraction ($f_u$) of the aspirin analogues (a) and diflunisal esters (b) versus carbon chain length at various concentrations (125 M □, 250 M ○, 500 M )). It is apparent that the most lipophilic compounds have the lowest $f_u$ values. Thus, the strength of protein binding increases in proportion to lipophilicity.

FIGS. 6a & 6b.

The relationship between lesion index and carbon chain length in the ester O-acyl moiety. The figures show that when orally administered, the more lipophilic (longer O-acyl carbon side chain) salicylic acid or diflunisal phenolic esters caused considerably less damage than their shorter chain analogues (r²=0.74 for salicylic acid derivatives; r²0.97 for diflunisal derivatives) to the gastric mucous. (a): salicylic acid derivatives, (b): diflunisal esters.

FIG. 7.

The comparison of gastric lesion indices for various salicylates in disease-stressed rats. The figure shows that when orally administered, aspirin caused far more gastric mucosal injury than any other compounds included in this study. Histological evaluation confirmed the almost total absence of lesions in stomachs taken from rats treated with 50 mg/Kg of C7D which is equivalent to 100 mg/Kg of aspirin.

FIG. 8.

The relationship between the length of the carbon chain in the O-acyl moiety and the preincubation time required for anti-aggregating activity. The longer chain derivatives required longer preincubation time, consistent with increased lipophilicity. (○) represents salicylic acid derivative and (□) represents diflunisal derivative.

FIG. 9.

The prediction of in-vivo hepatic extraction versus carbon chain length in the O-acyl moiety. The figure shows that the systemic availability after first-pass clearance by the liver of these O-acyl derivatives are significantly less than aspirin. (○) represents salicylic acid derivative and (□) represents diflunisal derivative.

FIG. 10.

Topographic Overview:

Focussing anti-platelet activity to the portal circulation depends on extensive hepatic de-acylation of the compounds, forming platelet-inactive salicylate. This report demonstrates the possibility of increasing the hepatic elimination of an aspirin or diflunisal analogue by increasing the carbon chain length of the phenolic ester moiety. Increasing the hepatic elimination in this way may diminish unwanted effect in the systemic circulation.

FIG. 11.

Relationship between HPLC retention time and carbon chain length in the diflunisal O-acyl moiety (y=0.7872+0.2211x, r²=0.99).

FIGS. 12a–12e.

Normalized outflow concentration versus time profiles for the pregenerated DF and its O-acyl esters injected into the liver together with EB and $^3$H -water as reference markers. a: DF, b: C2D, c: C4D, d: C5D, e: C6D.

FIGS. 13a–13e.

Dispersion model fitting of the normalized outflow concentration versus time profiles for the pregenerated DF and its O-acyl esters. The dotted line represents the predictions using dispersion model derived parameters. The filled circles represent the experimentally observed data. a: DF, b: C2D, c: C4D, d: C5D, e: C6D.

FIG. 14.

The relationship between hepatic mean transit time (MTT) and carbon number in the O-acyl moiety for the diflunisal esters. The figure shows an inverse relationship between MTT and carbon chain length (y=12.3064−1.0782x, r²=0.97).

FIGS. 15a and 15b.

The comparison of predicted and experimentally observed MTT (a) and CV2 values (b) for the diflunisal esters. The filled circle represents observed value. The dotted line represents predicted value using dispersion model fitting.

FIG. 16.

The relationship between $R_N/f_{ub}$ and carbon chain length in the diflunisal ester O-acyl moiety. The removal of unbound diflunisal ester ($R_N/f_{ub}$) increased in a log-linear fashion with increasing carbon chain length (y=0.8531+0.0512x, r²=0.75).

FIG. 17.

The effects of aspirin analogues and diflunisal esters on bile production. The unfilled bar represents the first stage of experiment (0–70 min) . The filled bar represents the second stage of experiment (70–140 min).

FIG. 18.

The relationship between biological activity (log 1/C) and lipophilicity (log P) for aspirin analogues and diflunisal esters by using nonlinear regression analysis. The best correlation is log 1/C=4.065+0.282 ( 0.05) log P=0.033 ( 0.009) (log P)² (n=11, r=0.983, s=0.065, optimum log P=4.46). The solid line represents this parabolic relationship. The filled circle represents each compound.

What is claimed is:

1. A method for treating and/or controlling thrombosis in a mammal, comprising administering to a mammal in need thereof an effective dosage of a compound having the formula:

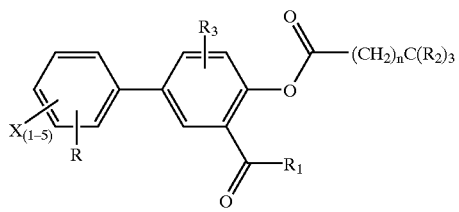

(I)

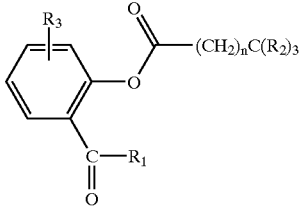

(III)

wherein n is 3 to 13

X is each independently a halogen, X being on one or more of the phenyl carbon atoms;

R is selected from the group consisting of hydrogen, halogen, lower alkyl, and lower alkoxy;

$R_1$ is selected from the group consisting of hydroxy, amino, lower alkoxy, lower alkylamino, di(lower alkyl) amino, diloweralkylaminoloweralkylamino, diloweralkylaminoloweralkoxy, hydroxyloweralkoxy, polyhydroxyloweralkoxy, loweralkoxyloweralkoxy, phenyl-loweralkoxy, phenoxy, substituted phenoxy, carboxy, carbloweralkoxy, loweralkanoylamino-loweralkoxy, hydrazino, hydroxylamino, N-morpholino, N-(4-loweralkylpiperidino), N-[4-(hydroxyloweralkyl)-piperidino], (hydroxyloweralkyl) amino, and a naturally occurring amino acid radical with attachment at the a-amino nitrogen;

$R_2$ is each independently hydrogen or a halogen; and $R_3$ is selected from the group consisting of hydrogen, 3- and 4-lower alkyl, lower alkoxy, benzyl and halo;

or a pharmaceutically acceptable salt thereof.

2. A method of treating and/or controlling thrombosis in a mammal, comprising administering to a mammal in need thereof a composition comprising an effective dosage of a compound having the formula:

wherein:

n is 3 to 13;

$R_1$ is selected from the group consisting of hydroxy, amino, lower alkoxy, lower alkylamino, di(lower alkyl) amino, diloweralkylaminoloweralkylamino, diloweralkylaminoloweralkoxy, hydroxyloweralkoxy, polyhydroxyloweralkoxy, loweralkoxyloweralkoxy, phenyl-loweralkoxy, phenoxy, substituted phenoxy, carboxy, carbloweralkoxy, loweralkanoylamino-loweralkoxy, hydrazino, hydroxylamino, N-morpholino, N-(4-loweralkylpiperidino), N-[4-(hydroxyloweralkyl)-piperidino], (hydroxyloweralkyl) amino, and a naturally occurring amino acid radical with attachment at the α-amino nitrogen;

$R_2$ is each independently hydrogen or a halogen; and $R_3$ is selected from the group consisting of hydrogen, 3- and 4-lower alkyl, lower alkoxy, benzyl and halo;

or a pharmaceutically acceptable salt thereof.

3. The method of claim 1, wherein the compound is diflunisal or alkanoyl derivatives of diflunisal selected from the group consisting of acetyl, propionyl, butyryl, pentanoyl, hexanoyl and heptanoyl derivatives of diflunisal, or a pharmaceutically acceptable salt thereof.

4. The method of claim 2, wherein the compound is selected from the group consisting of propionyl, butyryl, pentanoyl, hexanoyl and heptanoyl derivatives of salicyclic acid or a pharmaceutically acceptable salt thereof.

* * * * *